United States Patent
Pawlowski et al.

(10) Patent No.: US 12,391,988 B2
(45) Date of Patent: Aug. 19, 2025

(54) SEQUENCING A TARGET SEQUENCE IN A CELL

(71) Applicant: Singular Genomics Systems, Inc., San Diego, CA (US)

(72) Inventors: Andrew Pawlowski, San Diego, CA (US); Yeoan Youn, San Diego, CA (US); Michael Lawson, Pasadena, CA (US); Martin Maria Fabani, Encinitas, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 18/958,854

(22) Filed: Nov. 25, 2024

(65) Prior Publication Data

US 2025/0115958 A1    Apr. 10, 2025

Related U.S. Application Data

(63) Continuation of application No. PCT/US2024/032152, filed on May 31, 2024.

(60) Provisional application No. 63/505,585, filed on Jun. 1, 2023.

(51) Int. Cl.
| | | |
|---|---|---|
| C12P 19/34 | (2006.01) | |
| C12Q 1/25 | (2006.01) | |
| C12Q 1/6841 | (2018.01) | |
| C12Q 1/6862 | (2018.01) | |
| C12Q 1/6874 | (2018.01) | |

(52) U.S. Cl.
CPC ............ *C12Q 1/6874* (2013.01); *C12Q 1/25* (2013.01); *C12Q 1/6841* (2013.01); *C12Q 1/6862* (2013.01); *G01N 2333/9015* (2013.01)

(58) Field of Classification Search
CPC ............................ C12Q 1/6844; C12Q 1/6869
See application file for complete search history.

(56) References Cited

U.S. PATENT DOCUMENTS

| | | |
|---|---|---|
| 4,792,520 A | 12/1988 | Stambrook et al. |
| 6,218,122 B1 | 4/2001 | Friend et al. |
| 6,365,367 B1 | 4/2002 | Friedman et al. |
| 7,271,952 B2 | 9/2007 | Suzuki et al. |
| 7,390,463 B2 | 6/2008 | He et al. |
| 8,551,710 B2 | 10/2013 | Bernitz et al. |
| 9,371,598 B2 | 6/2016 | Chee |
| 9,556,473 B2 | 1/2017 | Bernitz et al. |

(Continued)

FOREIGN PATENT DOCUMENTS

| | | |
|---|---|---|
| JP | 2005/265627 A | 9/2005 |
| JP | 5970959 B2 | 8/2016 |

(Continued)

OTHER PUBLICATIONS

Agrawal, S. et al. (Nov. 15, 2016). "Nivolumab dose selection: challenges, opportunities, and lessons learned for cancer immunotherapy," *Journal of Immunotherapy Cancer* 4: 72.

(Continued)

*Primary Examiner* — Kenneth R Horlick
(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are methods for sequencing a target sequence in a cell by forming a circular oligonucleotide that incorporates a complement of the target sequence.

20 Claims, 6 Drawing Sheets

Specification includes a Sequence Listing.

(56) References Cited

U.S. PATENT DOCUMENTS

| | | |
|---|---|---|
| 9,593,365 B2 | 3/2017 | Frisen et al. |
| 9,598,723 B2 | 3/2017 | Ammann et al. |
| 10,059,990 B2 | 8/2018 | Boyden et al. |
| 10,114,015 B2 | 10/2018 | Glezer et al. |
| 10,138,509 B2 | 11/2018 | Church et al. |
| 10,266,888 B2 | 4/2019 | Daugharthy et al. |
| 10,323,272 B1 | 6/2019 | Rabbani et al. |
| 10,495,554 B2 | 12/2019 | Deisseroth et al. |
| 10,774,374 B2 | 9/2020 | Frisen et al. |
| 10,841,507 B2 | 11/2020 | Schürf et al. |
| 11,155,858 B2 | 10/2021 | Glezer et al. |
| 11,434,525 B2 | 9/2022 | Glezer |
| 11,459,603 B2 | 10/2022 | Tyagi et al. |
| 11,486,004 B2 | 11/2022 | Witters et al. |
| 11,492,662 B2 | 11/2022 | Glezer et al. |
| 11,597,965 B2 | 3/2023 | Nilsson et al. |
| 11,643,679 B2 | 5/2023 | Glezer et al. |
| 11,680,288 B2 | 6/2023 | Glezer |
| 11,753,678 B2 | 9/2023 | Glezer |
| 11,891,656 B2 | 2/2024 | Glezer et al. |
| 12,006,534 B2 | 6/2024 | Glezer |
| 12,071,667 B2 | 8/2024 | Bava et al. |
| 2001/0053519 A1 | 12/2001 | Fodor et al. |
| 2002/0064779 A1 | 5/2002 | Landegren et al. |
| 2003/0032024 A1 | 2/2003 | Lizardi et al. |
| 2003/0049862 A1 | 3/2003 | He et al. |
| 2003/0082556 A1 | 5/2003 | Kaufman et al. |
| 2003/0143536 A1 | 7/2003 | Lizardi |
| 2004/0137484 A1 | 7/2004 | Zhang et al. |
| 2005/0089860 A1 | 4/2005 | Arita |
| 2005/0130173 A1 | 6/2005 | Leamon et al. |
| 2005/0142556 A1 | 6/2005 | Hoon et al. |
| 2005/0208644 A1 | 9/2005 | Takiguchi et al. |
| 2005/0287526 A1 | 12/2005 | Landegren et al. |
| 2006/0050376 A1 | 3/2006 | Houston et al. |
| 2006/0166245 A1 | 7/2006 | Potter et al. |
| 2006/0292559 A1 | 12/2006 | Reddy et al. |
| 2009/0048119 A1 | 2/2009 | Krjutskov et al. |
| 2009/0263872 A1 | 10/2009 | Shannon et al. |
| 2009/0298718 A1 | 12/2009 | Denman et al. |
| 2011/0223585 A1 | 9/2011 | Gullberg et al. |
| 2012/0009629 A1 | 1/2012 | Becker et al. |
| 2012/0301886 A1 | 11/2012 | Farrell et al. |
| 2013/0296535 A1 | 11/2013 | Church et al. |
| 2014/0056811 A1 | 2/2014 | Jacob et al. |
| 2014/0057799 A1 | 2/2014 | Johnson et al. |
| 2014/0120534 A1 | 5/2014 | Bernitz et al. |
| 2014/0170654 A1 | 6/2014 | Landegren et al. |
| 2014/0256588 A1 | 9/2014 | Glezer et al. |
| 2015/0167092 A1 | 6/2015 | Kartalov et al. |
| 2015/0225778 A1 | 8/2015 | Hindson et al. |
| 2016/0108392 A1 | 4/2016 | Stelling |
| 2016/0116384 A1 | 4/2016 | Chen et al. |
| 2016/0145696 A1 | 5/2016 | Brandon et al. |
| 2016/0257993 A1 | 9/2016 | Fu et al. |
| 2016/0304952 A1 | 10/2016 | Boyden et al. |
| 2016/0369329 A1 | 12/2016 | Cai et al. |
| 2017/0067096 A1 | 3/2017 | Wassie et al. |
| 2017/0067925 A1 | 3/2017 | Spence et al. |
| 2017/0107563 A1 | 4/2017 | Samusik et al. |
| 2017/0343539 A1 | 11/2017 | Epstein et al. |
| 2018/0037943 A1 | 2/2018 | Rothwell et al. |
| 2018/0187242 A1 | 7/2018 | Makrigiorgos et al. |
| 2018/0223349 A1 | 8/2018 | Heller et al. |
| 2018/0246076 A1 | 8/2018 | Qian et al. |
| 2019/0017106 A1 | 1/2019 | Frisen et al. |
| 2019/0032121 A1 | 1/2019 | Daugharthy et al. |
| 2019/0055594 A1 | 2/2019 | Samusik et al. |
| 2019/0064109 A1 | 2/2019 | Brown et al. |
| 2019/0071668 A1 | 3/2019 | Schmidt et al. |
| 2019/0113423 A1 | 4/2019 | Goodman et al. |
| 2019/0119735 A1 | 4/2019 | Deisseroth et al. |
| 2019/0145982 A1 | 5/2019 | Chee et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0241950 A1 | 8/2019 | Daugharthy et al. |
| 2019/0258777 A1 | 8/2019 | Bo et al. |
| 2019/0264279 A1 | 8/2019 | Kain et al. |
| 2019/0376123 A1 | 12/2019 | Bobrow et al. |
| 2019/0391140 A1 | 12/2019 | Aghvanyan et al. |
| 2020/0032334 A1 | 1/2020 | Hubbell |
| 2020/0071751 A1 | 3/2020 | Daugharthy et al. |
| 2020/0087707 A1 | 3/2020 | Engreitz |
| 2020/0103639 A1 | 4/2020 | Skinner et al. |
| 2020/0124601 A1 | 4/2020 | Fan et al. |
| 2020/0140944 A1 | 5/2020 | Belgrader et al. |
| 2020/0224244 A1 | 7/2020 | Nilsson et al. |
| 2020/0224544 A1 | 7/2020 | Barker et al. |
| 2020/0271556 A1 | 8/2020 | Sarkar et al. |
| 2020/0277663 A1 | 9/2020 | Iyer et al. |
| 2020/0277664 A1 | 9/2020 | Frenz |
| 2020/0290043 A1 | 9/2020 | Williamson et al. |
| 2020/0294439 A1 | 9/2020 | Mandle et al. |
| 2020/0362334 A1 | 11/2020 | Regev et al. |
| 2020/0393477 A1 | 12/2020 | Davey et al. |
| 2021/0039062 A1 | 2/2021 | Mirkin et al. |
| 2021/0108195 A1 | 4/2021 | Bernate et al. |
| 2021/0164029 A1 | 6/2021 | Sekedat et al. |
| 2021/0164039 A1 | 6/2021 | Wang et al. |
| 2021/0189481 A1 | 6/2021 | Glezer et al. |
| 2021/0198727 A1 | 7/2021 | Kühnemund et al. |
| 2021/0222262 A1 | 7/2021 | Bakaher et al. |
| 2021/0238662 A1 | 8/2021 | Bava et al. |
| 2021/0238674 A1* | 8/2021 | Bava .................. C12Q 1/6844 |
| 2021/0262018 A1 | 8/2021 | Bava et al. |
| 2021/0292834 A1 | 9/2021 | Daugharthy et al. |
| 2021/0318530 A1 | 10/2021 | Deissler |
| 2021/0333211 A1 | 10/2021 | Chen et al. |
| 2021/0363579 A1 | 11/2021 | Daugharthy |
| 2021/0382033 A1 | 12/2021 | Mir |
| 2021/0388424 A1 | 12/2021 | Bava |
| 2022/0042084 A1 | 2/2022 | Glezer |
| 2022/0112486 A1 | 4/2022 | Ramachandran Iyer et al. |
| 2022/0229044 A1 | 7/2022 | Feldman et al. |
| 2022/0333174 A1 | 10/2022 | Glezer et al. |
| 2022/0372570 A1 | 11/2022 | Costa |
| 2022/0403456 A1 | 12/2022 | Glezer et al. |
| 2022/0403457 A1 | 12/2022 | Glezer et al. |
| 2023/0027467 A1 | 1/2023 | Fredriksson |
| 2023/0031996 A1 | 2/2023 | Hernandez et al. |
| 2023/0037182 A1* | 2/2023 | Bava .................. C12Q 1/6853 |
| 2023/0088043 A1 | 3/2023 | Kovacs et al. |
| 2023/0097368 A1 | 3/2023 | Glezer |
| 2023/0100215 A1 | 3/2023 | Glezer et al. |
| 2023/0203570 A1 | 6/2023 | Kovacs et al. |
| 2023/0279480 A1* | 9/2023 | Kühnemund ........ C12Q 1/6844 435/6.12 |
| 2023/0357828 A1 | 11/2023 | Lezer |
| 2023/0366013 A1 | 11/2023 | Glezer |
| 2023/0374572 A1 | 11/2023 | Glezer |
| 2024/0026428 A1 | 1/2024 | Glezer et al. |
| 2024/0182956 A1 | 6/2024 | Glezer et al. |
| 2024/0287590 A1 | 8/2024 | Glezer |
| 2024/0360496 A1 | 10/2024 | Glezer |

FOREIGN PATENT DOCUMENTS

| | | |
|---|---|---|
| WO | WO-2005/039389 A2 | 5/2005 |
| WO | WO-2008/042067 A2 | 4/2008 |
| WO | WO-2013/090360 A2 | 6/2013 |
| WO | WO-2013/090360 A3 | 8/2013 |
| WO | WO-2014/030066 A2 | 2/2014 |
| WO | WO-2014/030066 A3 | 5/2014 |
| WO | WO-2017/079382 A1 | 5/2017 |
| WO | WO-2017/143317 A1 | 8/2017 |
| WO | WO-2018/091676 A1 | 5/2018 |
| WO | WO-2019/068880 A1 | 4/2019 |
| WO | WO-2019/084062 A1 | 5/2019 |
| WO | WO-2019/195346 A1 | 10/2019 |
| WO | WO-2019/199579 A1 | 10/2019 |
| WO | WO-2019/222284 A1 | 11/2019 |
| WO | WO-2020/028194 A1 | 2/2020 |

(56) References Cited

FOREIGN PATENT DOCUMENTS

| | | |
|---|---|---|
| WO | WO-2020/076976 A1 | 4/2020 |
| WO | WO-2020/076979 A1 | 4/2020 |
| WO | WO-2020/096687 A1 | 5/2020 |
| WO | WO-2020/099640 A1 | 5/2020 |
| WO | WO-2020/102766 A2 | 5/2020 |
| WO | WO-2020/123309 A1 | 6/2020 |
| WO | WO-2020/160044 A1 | 8/2020 |
| WO | WO-2022/032194 A1 | 2/2022 |
| WO | WO-2022/032195 A2 | 2/2022 |
| WO | WO-2022/032195 A3 | 3/2022 |
| WO | WO-2022/235764 A1 | 11/2022 |
| WO | WO-2023-283090 A1 | 1/2023 |
| WO | WO-2023/076832 A1 | 5/2023 |
| WO | WO-2023/077109 A1 | 5/2023 |
| WO | WO-2024/182295 A2 | 9/2024 |
| WO | WO-2024/220013 A1 | 10/2024 |
| WO | WO-2024/249961 A1 | 12/2024 |

OTHER PUBLICATIONS

Ahern, H. (1995). "Biochemical, reagent kits offer scientists good return on investment," *Scientist* 9(15): 20.

Alon, S. et al. (Jan. 19, 2021). "Expansion Sequencing: Spatially Precise In Situ Transcriptomics in Intact Biological Systems," *Science* 371(6528): eaax2656.

Ambardar, S. et al. (Dec. 2016, e-published Jul. 9, 2016). "High throughput sequencing: an overview of sequencing chemistry," *Indian journal of microbiology* 56: 394-404.

Arce, S. H. et al. (Jul. 24, 2013). "Fast and accurate automated cell boundary determination for fluorescence microscopy," *Sci Rep* 3: 2266.

Banér, J. et al. (Apr. 1, 2005). "Analysis of T-cell receptor vβ gene repertoires after immune stimulation and in malignancy by use of padlock probes and microarrays," *Clinical chemistry* 51(4): 768-775.

Borkamo, E. D. et al. (Dec. 1, 2009, e-published Nov. 19, 2009). "cDNA microarray analysis of serially sampled cervical cancer specimens from patients treated with thermochemoradiotherapy," *International Journal of Radiation Oncology\*Biology\*Physics* 75(5): 1562-1569.

Bullinger, L. et al. (Apr. 15, 2004). "Use of gene-expression profiling to identify prognostic subclasses in adult acute myeloid leukemia," *New England Journal of Medicine* 350(16): 1605-1616.

Carow, B. et al. (Apr. 23, 2019). "Spatial and temporal localization of immune transcripts defines hallmarks and diversity in the tuberculosis granuloma," *Nature Communications* 10(1): 1823.

Carpenter, A. E. et al (Oct. 31, 2016). "CellProfiler: image analysis software for identifying and quantifying cell phenotypes," *Genome Biology* 7(10): R100.

Catuogno, S. et al. (Apr. 8, 2011). "Recent advance in biosensors for microRNAs detection in cancer," *Cancers* 3(2): 1877-1898.

Chen, F. et al. (Jan. 30, 2015, e-published Jan. 15, 2015). "Optical imaging. Expansion microscopy," *Science* 347(6221): 543-548.

Chen, K. H. et al. (Apr. 24, 2015, e-published Apr. 9, 2015). "RNA imaging. Spatially resolved, highly multiplexed RNA profiling in single cells," *Science* 348(6233): aaa6090.

Chen, X. et al. (Feb. 28, 2018, e-published Nov. 28, 2017). "Efficient in situ barcode sequencing using padlock probe-based BaristaSeq," *Nucleic acids research* 46(4): Article e22, pp. 1-10.

Chen, X. et al. (Oct. 17, 2019). "High-throughput mapping of long-range neuronal projection using in situ sequencing," *Cell* 179(3): 772-786.

Christian, A. T. et al. (Dec. 4, 2001, e-published Nov. 27, 2001). "Detection of DNA point mutations and mRNA expression levels by rolling circle amplification in individual cells," *PNAS USA* 98(25): 14238-14243.

Conze, T et al. (Jul. 2009, e-published Feb. 19, 2009). "Analysis of genes, transcripts, and proteins via DNA ligation," *Annual review of analytical chemistry* 2(1): 215-239.

Costea, P. I. et al. (Mar. 4, 2013). "TagGD: fast and accurate software for DNA Tag generation and demultiplexing," *PLoS One* 8(3): e57521.

Daigeler, A. et al. (Jul. 6, 2006). "Clinicopathological findings in a case series of extrathoracic solitary fibrous tumors of soft tissues," *BMC surgery* 6: 1-8.

Denkert, C. et al. (Nov. 1, 2015, e-published Aug. 14, 2015). "Strategies for developing Ki67 as a useful biomarker in breast cancer," *The Breast* 24: S67-S72.

Edelman, M. J. et al. (May 1997, e-published Feb. 28, 2002). "The utility of follow-up testing after curative cancer therapy: a critical review and economic analysis," *Journal of general internal medicine* 12(5): 318-331.

El-Sagheer, A. H. et al. (Aug. 21, 2012, e-published Mar. 22, 2012)." Click nucleic acid ligation: applications in biology and nanotechnology," *Accounts of chemical research* 45(8):1258-1267.

Extended European Search Report mailed Mar. 18, 2024, for EP Application No. 21852670.5, 13 pages.

Extended European Search Report mailed Mar. 28, 2024, for EP Application No. 21853956.7, 8 pages.

Fijnvandraat, A. C. et al. (Sep. 1, 2002, e-published Sep. 10, 2002). "Nonradioactive in situ detection of mRNA in ES cell-derived cardiomyocytes and in the developing heart," *Microscopy research and technique* 58(5): 387-394.

Frances-Soriano, L. et al. (Jan. 26, 2021, e-published Dec. 28, 2020). "In Situ rolling circle amplification Forster resonance energy transfer (RCA-FRET) for washing-free real-time single-protein imaging," *Analytical Chemistry* 93(3): 1842-1850.

Frank, D. N. (Oct. 29, 2009). "BARCRAWL and BARTAB: software tools for the design and implementation of barcoded primers for highly multiplexed DNA sequencing," *BMC bioinformatics* 10(1): 1-13.

Fredriksson, S. et al. (Apr. 2007, e-published Mar. 18, 2007). "Multiplexed protein detection by proximity ligation for cancer biomarker validation," *Nature methods* 4(4): 327-329.

Fredriksson, S. et al. (May 1, 2002). "Protein detection using proximity-dependent DNA ligation assays," *Nature biotechnology* 20(5): 473-477.

Gao, H. et al. (Dec. 2019, e-published Oct. 17, 2019). "Rolling circle amplification for single cell analysis and in situ sequencing," *TrAC Trends in Analytical Chemistry* 121: 115700.

Garmendia, C. et al. (Feb. 1992, e-published Feb. 5, 1992). "The bacteriophage phi 29 DNA polymerase, a proofreading enzyme," *Journal of Biological Chemistry* 267(4): 2594-2599.

Gelali, E. et al. (Apr. 9, 2019). "iFISH is a publically available resource enabling versatile DNA FISH to study genome architecture," *Nat Commun* 10(1): 1636.

Gore, A. et al. (Mar. 3, 2011, e-published Mar. 2, 2011). "Somatic coding mutations in human induced pluripotent stem cells," *Nature* 471 (7336): 63-67.

Gullberg, M. et al. (May 21, 2004). "Cytokine detection by antibody-based proximity ligation," *PNAS* 101(22): 8420-8424.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27): 9145-9150.

Gyllborg, D. et al. (Nov. 4, 2020). "Hybridization-based in situ sequencing (HybISS) for spatially resolved transcriptomics in human and mouse brain tissue," *Nucleic Acids Research* 48(19): e112.

Hagai, T. et al. (Nov. 2018, e-published Oct. 24, 2018). "Gene expression variability across cells and species shapes innate immunity," *Nature* 563(7730): 197-202.

Hamaday, M. et al. (Mar. 2008, e-published Feb. 10, 2008). "Error-correcting barcoded primers for pyrosequencing hundreds of samples in multiplex," *Nature Methods* 5(3): 235.

Hamilton, N. (Feb. 10, 2008) "Quantification and its applications in fluorescent microscopy imaging." *Traffic* 10(8): 951-961.

Hardenbol, P. et al. (Jun. 1, 2003, e-published May 5, 2003) "Multiplexed genotyping with sequence-tagged molecular inversion probes." *Nature biotechnology* 21(6): 673-678.

Heintzmann, R. et al. (Dec. 13, 2017, e-published Nov. 10, 2017). "Super-Resolution Structured Illumination Microscopy," *Chem. Rev.* 117(23): 13890-13908.

(56) References Cited

OTHER PUBLICATIONS

Hu, Y. et al. (Sep. 3, 2014) "Sensitive quantification of messenger RNA with a real-time ligase chain reaction by using a ribonucleotide-modified DNA probe." *Chemical Communications* 50(86): 13093-13095.
International Search Report and Written Opinion mailed on Nov. 23, 2021, for PCT Application No. PCT/US2021/045104, filed Aug. 6, 2021, 15 pages.
International Search Report & Written Opinion mailed on Jan. 31, 2022, for PCT Application No. PCT/US2021/045105, filed Aug. 6, 2022, 18 pages.
International Search Report & Written Opinion mailed on Sep. 19, 2022, for PCT Application No. PCT/US2022/027630, filed May 4, 2022, 14 pages.
International Search Report and Written Opinion mailed on May 26, 2023 for PCT Application No. PCT/US2022/078941, filed Oct. 28, 2022, 16 pages.
International Search Report and Written Opinion mailed on Oct. 28, 2024 for PCT Application No. PCT/US2024/032152, filed May 31, 2024, 28 pages.
Jeong, S. et al. (Apr. 2020, e-published Jan. 30, 2020). "Current immunoassay methods and their applications to clinically used biomarkers of breast cancer," *Clinical biochemistry* 78: 43-57.
Kappler, K. et al. (Aug. 2020, e-published Aug. 5, 2020). "Emergence and significance of carbohydrate-specific antibodies," *Genes Immun* 21(4): 224-239.
Ke, R. et al. (Sep. 2013, e-published Jul. 14, 2013) "In situ sequencing for RNA analysis in preserved tissue and cells," *Nature methods* 10(9): 857-860.
Klein A. M., et al. (Jul. 25, 2017). "InDrops and Drop-seq technologies for single-cell sequencing," *Lab Chip* 17(15): 2540-2541.
Kobori, T. et al. (Jan. 2014) "Expanding possibilities of rolling circle amplification as a biosensing platform," *Analytical Sciences* 30(1): 59-64.
Kohman, R. E. et al. (Apr. 28, 2020). "Fluorescent in situ sequencing of DNA barcoded antibodies," *bioRxiv* Apr. 2020.
Krzywkowski, T. et al. (Oct. 2018). "Chimeric padlock and iLock probes for increased efficiency of targeted RNA detection," *RNA* 25(1): 82-89.
Lareau, C. A., et al. (Feb. 13, 2020). "Inference and effects of barcode multiplets in droplet-based single-cell assays," *Nature Communications* 11(1): 866.
Larimore, K. et al. (Sep. 15, 2012). "Shaping of human germline IgH repertoires revealed by deep sequencing," *The Journal of Immunology* 189(6): 3221-3230.
Larsson, C. et al., (May 2010, e-published Apr. 11, 2010). "In situ detection and genotyping of individual mRNA molecules," *Nature Methods* 7(5): 395-397.
Lee, J. H. et al. (Feb. 12, 2015). "Fluorescent in situ sequencing (FISSEQ) of RNA for gene expression profiling in intact cells and tissues," *Nature protocols* 10(3): 442-458.
Lee, J. H. et al. (Feb. 27, 2014, e-published Feb. 20, 2014). "Highly multiplexed subcellular RNA sequencing in situ," Science 343(6177): 1360-1363.
Li, J. B. et al. (Sep. 2009, e-published Jun. 12, 2009). Multiplex padlock targeted sequencing reveals human hypermutable CpG variations, *GenomeRes* 19(9): 1606-1615.
Li, J. B. et al. (May 29, 2009). "Genome-wide identification of human RNA editing sites by parallel DNA capturing and sequencing," *Science* 324(5931): 1210-1213.
Li, N. et al. (May 21, 2009). "Stand-alone rolling circle amplification combined with capillary electrophoresis for specific detection of small RNA." *Analytical chemistry* 81(12): 4906-4913.
Lubeck, E. et al. (Jul. 2012, e-published Jun. 3, 2012). "Single-cell systems biology by super-resolution imaging and combinatorial labeling," *Nature methods* 9(7): 743-748.
Lubeck, E. et al. (Apr. 2014, e-published Mar. 28, 2014). "Single-cell in situ RNA profiling by sequential hybridization," *Nature methods* 11(4): 360-361.

Manuguerra I. et al. (May 1, 2018). "Gene assembly via one-pot chemical ligation of DNA promoted by DNA nanostructures," *Chem Commun(Camb)* 54(36): 4529-4532.
Mignardi, M. et al. (Apr. 28, 2014). "Fourth-generation sequencing in the cell and the clinic," *Genome medicine* 6: 1-4.
Mitra, R.D. et al. (Sep. 1, 2003, e-published Jul. 15, 2003). "Fluorescent in situ sequencing on polymerase colonies." *Analytical biochemistry* 320(1): 55-65.
Mohammadi-Kambs, M. et al. (Apr. 30, 2017, e-published Apr. 5, 2017). "Hamming distance as a concept in DNA molecular recognition." *ACS omega* 2(4): 1302-1308.
Nilsson, M. et al. (Sep. 30, 1994). "Padlock probes: circularizing oligonucleotides for localized DNA detection," *Science* 265(5181) :2085-2088.
Nitta, H. et al. (Aug. 2013, e-published Nov. 15, 2015). "New methods for ALK status diagnosis in non-small-Cell lung Cancer: an improved ALK immunohistochemical assay and a new, Brightfield, dual ALK IHC—In situ hybridization assay," *Journal of Thoracic Oncology* 8(8): 1019-1031.
Odeh, F. et al. (Dec. 18, 2019). "Aptamers Chemistry: Chemical Modifications and Conjugation Strategies," *Molecules* (Basel, Switzerland) 25(1): 3.
Ouladan, S. et al. (Jun. 2015, e-published Apr. 20, 2015). "Differential diagnosis of solitary fibrous tumors: A study of 454 soft tissue tumors indicating the diagnostic value of nuclear STAT6 relocation and ALDH1 expression combined with in situ proximity ligation assay," *International journal of oncology* 46(6): 2595-2605.
Park, M. S. et al. (May 11, 2013). "The role of chemotherapy in advanced solitary fibrous tumors: a retrospective analysis," *Clinical sarcoma research* 3(1): 1-7.
Patel, A. P. et al. (Jun. 20, 2014, e-published Jun. 12, 2014). "Single-cell RNA-seq highlights intratumoral heterogeneity in primary glioblastoma," *Science* 344(6190): 1396-1401.
Pearson, A. et al. (Aug. 2016, e-published May 13, 2016). "High-Level Clonal FGFR Amplification and Response to FGFR Inhibition in a Translational Clinical Trial," *CancerDiscov* 6(8): 838-851.
Peerzade, S. A. et al. (May 8, 2020). "Ultrabright Fluorescent Silica Nanoparticles for Multiplexed Detection," *Nanomaterials* 10(5): 905.
Peters, J. M. et al. (Jan. 1, 2011). "Multiparameter flow cytometry in the diagnosis and management of acute leukemia," *ArchPathol Lab Med* 135(1): 44-54.
Porreca, G. J. et al. (Nov. 2007, e-published Oct. 14, 2007). "Multiplex amplification of large sets of human exons," *Nat Methods* 4(11): 931-936.
Rouhanifard, S. H., et al. (May 7, 2018) "Exponential fluorescent amplification of individual RNAs using clampFISH probes." *bioRxiv*, Article 222794.
Roussis, I. M. et al. (Mar. 3, 2017). "RNA whole-mount in situ hybridization proximity ligation assay (rISH-PLA), an assay for detecting RNA-protein complexes in intact cells," *Current protocols in cell biology* 74(1): 17-20.
Sansone, A. (Jun. 2019, e-published May 30, 2019). "Spatial transcriptomics levels up," *NatMethods* 16(6): 458.
Sapoznik, E. et al. (Nov. 12, 2020). "A versatile oblique plane microscope for large-scale and high-resolution imaging of subcellular dynamics," *eLife* 9: e57681.
Schallmeiner, E. et al. (Feb. 1, 2007, e-published Dec. 17, 2006). "Sensitive protein detection via triple-binder proximity ligation assays," *Nature methods* 4(2): 135-137.
Schlachter, S. et al. (Nov. 30, 2009). "A method to unmix multiple fluorophores in microscopy images with minimal a priori information," *OptExpress* 17(25): 22747-22760.
Shirakawa, H. et al. (Mar. 2004). "Blind spectral decomposition of single-cell fluorescence by parallel factor analysis," *Biophysical Journal* 86(3): 1739-1752.
Söderberg, O. et al. (Dec. 2006, e-published Oct. 29, 2006). "Direct observation of individual endogenous protein complexes in situ by proximity ligation," *Nature methods* 3(12): 995-1000.
Stratagene Catalog, The (1988). p. 39.
Strell, C. et al. (Apr. 2019, e-published Mar. 14, 2019). "Placing RNA in context and space-methods for spatially resolved transcriptomics," *The FEBS journal* 286(8): 1468-1481.

(56) References Cited

OTHER PUBLICATIONS

Suzuki, A. et al. (Dec. 20, 2019). "Characterization of cancer omics and drug perturbations in panels of lung cancer cells," *Sci. Rep* 9(1): 19529.

Takahashi, H. et al. (May 17, 2018). "RNase H-assisted RNA-primed rolling circle amplification for targeted RNA sequence detection." *Scientific reports* 8: 1-11.

Tang, S. et al. (Aug. 2, 2016). "Suppression of rolling circle amplification by nucleotide analogs in circular template for three DNA polymerases," *Bioscience, Biotechnology, and Biochemistry* 80(8): 1555-1561.

Turczyk, B. M. et al. (Jul. 2020). "Spatial sequencing: a perspective," *Journal of Biomolecular Technique* 31(2): 44.

Vickovic, S. et al. (Oct. 2019, e-published Sep. 9, 2019). "High-definition spatial transcriptomics for in situ tissue profiling," *Nat. Methods* 16(10): 987-990.

Wang, G. et al. (Mar. 19, 2018). "Multiplexed imaging of high-density libraries of RNAs with MERFISH and expansion microscopy," *SciRep* 8(1): 4847.

Wang X. et al. (Jul. 27, 2018, e-published Jun. 21, 2018). "Three-dimensional intact-tissue sequencing of single-cell transcriptional states," *Science* 361(6400): eaat5691.

Wassie, A. T. et al. (Dec. 20, 2018). "Expansion microscopy: principles and uses in biological research," *Nature methods* 16(1): 33-41.

Weibrecht, I. et al. (Jan. 24, 2013). "In situ detection of individual mRNA molecules and protein complexes or post-translational modifications using padlock probes combined with the in situ proximity ligation assay." *Nature protocols* 8(2): 355-372.

Wilson, C. S. et al. (Jul. 15, 2006, e-published Apr. 4, 2006). "Gene expression profiling of adult acute myeloid leukemia identifies novel biologic clusters for risk classification and outcome prediction," *Blood* 108(2): 685-696.

Xu, Q. et al. (Feb. 17, 2009). "Design of 240,000 orthogonal 25mer DNA barcode probes." *PNAS* 106(7): 2289-2294.

York, A. G. et al. (Nov. 2013, e-published Oct. 6, 2013). "Instant super-resolution imaging in live cells and embryos via analog image processing," *Nature Methods* 10(11): 1122-1126.

You, Y. et al. (Apr. 1, 2006, e-published Jan. 1, 2006). "Design of LNA probes that improve mismatch discrimination," *Nucleic acids research* 34(8): e60-e60.

Zhang, D. et al. (Jan. 2006, e-published Aug. 24, 2005). "Amplification of circularizable probes for the detection of target nucleic acids and proteins," *Clinica chimica acta* 363(1-2): 61-70.

Zhang, K. et al. (Aug. 2009, e-published Jul. 20, 2009). "Digital RNA allelotyping reveals tissue-specific and allele-specific gene expression in human," *Nature Methods* 6(8): 613-618.

Zheng, G. X. et al. (Jan. 16, 2017). "Massively parallel digital transcriptional profiling of single cells," *NatComm* 8: 14049.

Iyer, E. P. R et al. (Mar. 20, 2018). "Barcoded oligonucleotides ligated on RNA amplified for multiplex and parallel in-situ analyses," *BioRxiv.* 281121.

Ke, R et al. (Sep. 2013) "In situ sequencing for RNA analysis in preserved tissue and cells." *Nature methods* 10(9): 857-860.

Lundin, E. et al. (Jan. 14, 2020). "Spatiotemporal mapping of RNA editing in the developing mouse brain using in situ sequencing reveals regional and cell-type-specific regulation," *BMC biology* 18: 6, pp. 1-15.

\* cited by examiner

SEQUENCE LISTING

```
Sequence total quantity: 1
SEQ ID NO: 1           moltype = RNA   length = 13
FEATURE                Location/Qualifiers
source                 1..13
                       mol_type = mRNA
                       organism = Homo sapiens
SEQUENCE: 1
gtggtccctg gcc                                                              13
```

SEQUENCING A TARGET SEQUENCE IN A CELL

CROSS-REFERENCES TO RELATED APPLICATIONS

This application is a continuation of International Application No. PCT/US2024/032152, filed May 31, 2024, and which claims the benefit of U.S. Provisional Application No. 63/505,585, filed Jun. 1, 2023, each of which is incorporated herein by reference in their entirety and for all purposes.

SEQUENCE LISTING

The Sequence Listing written in file 601001WO_ST.26_Sequence_Listing.xml, created May 28, 2024, 2,007 bytes, machine format IBM-PC, MS Windows operating system, is hereby incorporated by reference.

BACKGROUND

Profiling the genome, epigenome, transcriptome, and proteome enables researchers to analyze heterogeneity and distributions of gene and protein co-expression patterns within cells and tissues. This level of information is pivotal for learning how cell co-localization influences microenvironments and ultimately the development of tissue and various diseases. As such, it can have wide-reaching implications for understanding and uncovering new therapies and treatments. Including spatial information while collecting and analyzing multiomics data enables a more comprehensive view than ever before, contributing powerful insights and knowledge that is often overlooked. Combining this data can reveal detailed information as to how diseases can spread and how cell to cell communication operates; it can also help in designing targeted treatment approaches. Thus, spatial information is invaluable when learning about multiomics and should not be excluded when fully exploring cell and tissue compositions. Disclosed herein, inter alia, are solutions to these and other problems in the art.

BRIEF SUMMARY

In an aspect is provided a method of forming a circular oligonucleotide, optionally in a cell or tissue (e.g., in situ). In embodiments, the method includes contacting a target polynucleotide complex (e.g., wherein the target polynucleotide complex is in a cell, on a cell, or in a tissue) with a probe oligonucleotide, thereby forming a probe polynucleotide complex, wherein the target polynucleotide complex includes a blocking oligonucleotide bound to a first sequence of a target polynucleotide, wherein the blocking oligonucleotide includes a probe hybridization sequence, and wherein the probe polynucleotide complex includes the probe oligonucleotide bound to a second sequence of the target polynucleotide and bound to the probe hybridization sequence, wherein the target sequence is between the first and second sequence; extending the probe oligonucleotide along the target sequence with a polymerase to generate an extension strand including a complementary sequence of the target sequence, and ligating the extension strand to the probe oligonucleotide hybridization sequence, thereby generating a circular oligonucleotide. In embodiments, the method includes amplifying and detecting the circular oligonucleotide. In embodiments, the method includes forming the circular oligonucleotide on a first device, isolating the circular oligonucleotide from the first device and sequencing the circular oligonucleotide (e.g., ex situ sequencing) on a different device.

In another aspect is provided a method of amplifying a target sequence, the method including: contacting a target polynucleotide complex with a probe oligonucleotide, thereby forming a probe polynucleotide complex, wherein the target polynucleotide complex includes a blocking oligonucleotide bound to a first sequence of a target polynucleotide, wherein the blocking oligonucleotide includes a probe hybridization sequence, and wherein the probe polynucleotide complex includes the probe oligonucleotide bound to a second sequence of the target polynucleotide and bound to the probe hybridization sequence, wherein the target sequence is between the first and second sequence; extending the probe oligonucleotide along the target sequence with a polymerase to generate an extension strand including a complement of the target sequence, and ligating the extension strand to the probe oligonucleotide hybridization sequence, thereby generating a circular oligonucleotide; and amplifying the circular oligonucleotide by extending an amplification primer hybridized to the circular oligonucleotide with a strand-displacing polymerase, thereby generating an amplification product including multiple copies of the target sequence.

In yet another aspect is provided a method of detecting a nucleic acid molecule in or on a cell, the method including amplifying the target sequence of the nucleic acid molecule as described herein, and sequencing the target sequence in or on the cell, thereby detecting the nucleic acid molecule.

In an aspect is provided a cell or tissue including a target polynucleotide complex as described herein. In embodiments, the target polynucleotide complex includes a first sequence of a blocking oligonucleotide bound to a first sequence of a target polynucleotide; a first sequence of a probe oligonucleotide bound to a second sequence of the target polynucleotide; wherein the first and second sequences of the target polynucleotide are separated by 1 or more nucleotides; and where a second sequence of the blocking oligonucleotide is bound to a second sequence of the probe oligonucleotide.

BRIEF DESCRIPTION OF THE DRAWINGS

FIG. 2B provides an illustration of an embodiment of the probe oligonucleotide, wherein the probe oligonucleotide is a linear, single-stranded oligonucleotide that includes a first sequence, C', which is complementary to the fourth sequence of the blocking oligonucleotide (i.e., C of FIG. 2A), and a second sequence, D', complementary to a third sequence of the target nucleic acid molecule. Though not included in the illustration, the probe oligonucleotide may further include one or more primer binding sites (e.g., sequences complementary to an amplification and/or sequencing primer).

DETAILED DESCRIPTION

Figure 1:
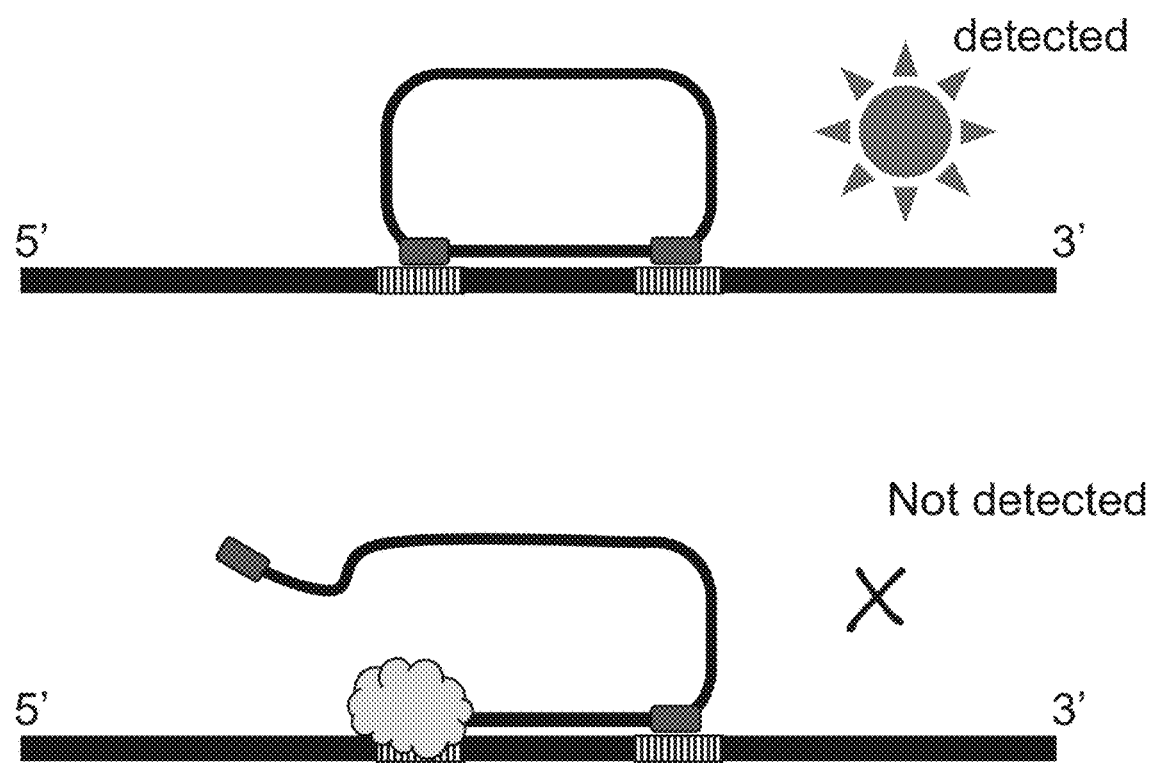
FIG. 1 illustrates one of the challenges with generating circular oligonucleotides including a complement of the target sequence. Ideally, the circularizable oligonucleotide hybridizes to two sequences flanking the sequence of interest (i.e., the target sequence) of a nucleic acid molecule. A polymerase extends the 3' end of the circularizable oligonucleotide, and a ligation reaction joins the 3' end of the extended oligonucleotide to the adjacent 5' end of the circularizable oligonucleotide, resulting in a circular oligonucleotide that incorporates a complement of the target sequence. The circular oligonucleotide may then be amplified via a rolling circle mechanism and detected (top of FIG. 1). Occasionally the target sequence of interest (e.g., mRNA) fold into complex secondary and tertiary structures, resulting in the formation of hairpin loops, pseudoknots, and other structures that can retard or stall the progression of a polymerase. Yet, while a strand-displacing polymerase can copy the target sequence despite having secondary structure elements, it will also unproductively displace the 5' end of the circularizable oligonucleotide; see the bottom of FIG. 1. When the 5' hybridization sequence of the circularizable oligonucleotide is displaced, the two ends cannot be ligated to form a circular oligonucleotide and thus cannot be amplified via a rolling circle mechanism, and thus minimizes the ability to detect the target sequence.

The aspects and embodiments described herein relate to detecting targets of a cell.

I. Definitions

All patents, patent applications, articles and publications mentioned herein, both supra and infra, are hereby expressly incorporated herein by reference in their entireties. The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "complement" is used in accordance with its plain and ordinary meaning and refers to a nucleotide (e.g., RNA nucleotide or DNA nucleotide) or a sequence of nucleotides capable of base pairing with a complementary nucleotide or sequence of nucleotides (e.g., Watson-Crick base pairing). As described herein and commonly known in the art the complementary (matching) nucleotide of adenosine is thymidine and the complementary (matching) nucleotide of guanosine is cytosine. Thus, a complement may include a sequence of nucleotides that base paired with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. Another example of complementary sequences are a template sequence and an amplicon sequence polymerized by a polymerase along the template sequence. "Duplex" means at least two oligonucleotides and/or polynucleotides that are fully or partially complementary undergo Watson-Crick type base pairing among all or most of their nucleotides so that a stable complex is formed. Complementary single stranded nucleic acids and/or substantially complementary single stranded nucleic acids can hybridize to each other under hybridization conditions, thereby forming a nucleic acid that is partially or fully double stranded. When referring to a double-stranded polynucleotide including a first strand hybridized to a second strand, it is understood that each of the first strand and the second strand are independently single-stranded polynucleotides. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often include nucleic acid sequences that are substantially complementary to each other.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g., chemical compounds including biomolecules, particles, solid supports, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme.

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may include natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

As used herein, the term "blocking oligonucleotide" refers to an oligonucleotide including a sequence complementary to a target polynucleotide and a sequence complementary to a probe oligonucleotide described herein. In embodiments, blocking oligonucleotide includes a first sequence complementary to a target polynucleotide and a second sequence complementary to a target polynucleotide in addition to a sequence complementary to a probe oligonucleotide described herein. Compositions and methods described herein are directed to detecting polynucleotide sequences in cells and tissues, and the use of the blocking oligonucleotide described herein reduce the unproductive displacement of the 5' end of the circularizable oligonucleotide and facilitates the formation of a circular oligonucleotide as depicted in FIG. 3C, which is then subjected to multiple rounds of amplification and detection.

Figure 2A:
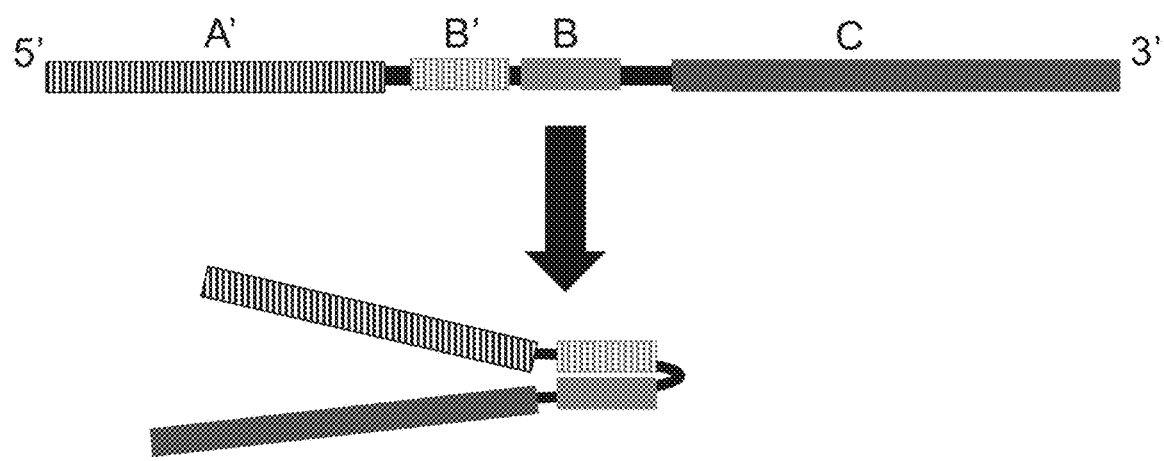
FIGS. 2A-2B illustrates two different oligonucleotides, a blocking oligonucleotide (FIG. 2A) and a probe oligonucleotide (FIG. 2B) useful for detection of target nucleic acid sequences. The blocking oligonucleotide includes a first sequence, A', complementary to a first sequence of a target nucleic acid molecule. The blocking oligonucleotide also includes a second complementary sequence, B', wherein B' is complementary to a second sequence of the target nucleic acid molecule. The second sequence of the blocking oligonucleotide, B' is also complementary to a third sequence of the blocking oligonucleotide, referred to as B in FIG. 2A. Thus, in embodiments, the third sequence (i.e., the B sequence) is substantially homologous or substantially identical to a sequence of the target polynucleotide. The B' and B sequences may also be referred to herein as "curl sequences." Under suitable hybridization conditions, the second and third sequences of the blocking oligonucleotide may hybridize together, as illustrated in the bottom of FIG. 2A. The blocking oligonucleotide further includes a fourth sequence, C, which is complementary to a portion of the probe oligonucleotide.

As used herein, the term "curl sequence" refers to a sequence in an oligonucleotide that is hybridizable with another sequence within the same oligonucleotide. As described herein, the blocking oligonucleotide includes a first sequence complementary to a target polynucleotide (e.g., A') and a second sequence complementary to the target polynucleotide (e.g., B'). It is understood that A' and B' may form part of the same sequence, wherein B' is the downstream region or portion of the sequence. The second sequence of the blocking oligonucleotide, B', is also complementary to a third sequence of the blocking oligonucleotide, referred to as B in FIG. 2A. Thus, in embodiments, the third sequence (i.e., the B sequence) is substantially homologous or substantially identical to a sequence of the target polynucleotide. The B' and B sequences may also be referred to herein as "curl sequences." Under suitable hybridization conditions, the second (i.e., B') and third sequences (i.e., B) of the blocking oligonucleotide may hybridize together, as illustrated in the bottom of FIG. 2A. The blocking oligonucleotide further includes a fourth sequence, C, which is complementary to a portion of the probe oligonucleotide.

Figure 2B:
Figure 3A:
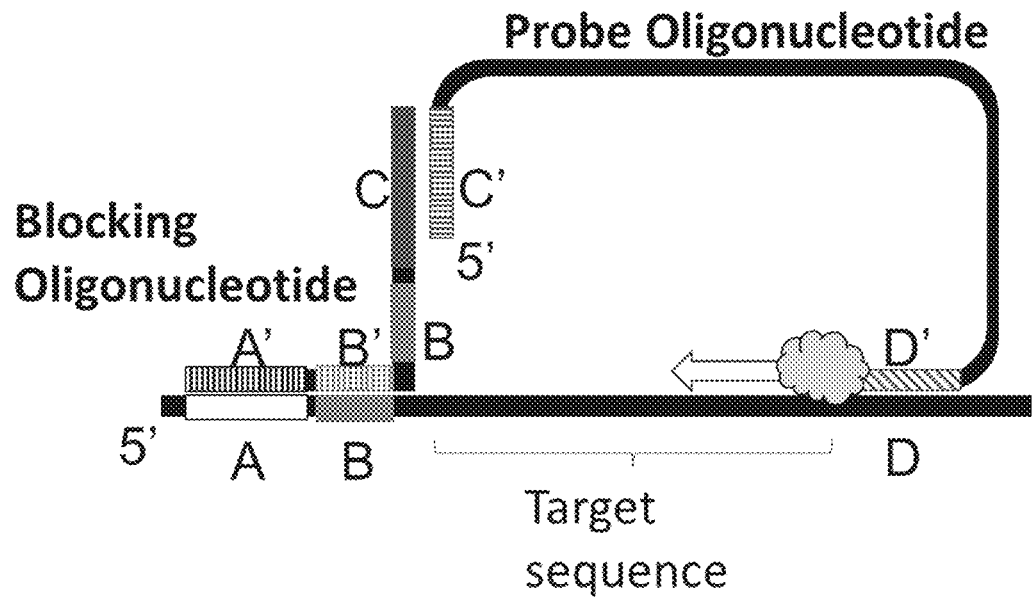
FIGS. 3A-3C provides an illustration of the two oligonucleotides when bound to a target nucleic acid molecule (FIG. 3A), the intermediate complex (FIG. 3B), and the resultant circular oligonucleotide (FIG. 3C). The target nucleic acid molecule may be within a cell or tissue that is attached to a substrate surface, wherein the cell or tissue is fixed (e.g., using a fixing agent) and permeabilized according to known methods. The cell may have been cultured on the surface, or the cell may have been initially cultured in suspension and then fixed to the surface. The nucleic acid molecule (e.g., mRNA, oncogene, or other nucleic acid sequence of interest) may present within the cell, or within the extracellular matrix. As described further herein, the first and second sequences of the blocking oligonucleotide (represented as A' and B') hybridize to the target nucleic acid molecule, wherein the A' and B' hybridize to complementary regions adjacent to a target sequence of interest. The first sequence of the probe oligonucleotide hybridizes to the fourth sequence of the blocking oligonucleotide. The second sequence of the probe oligonucleotide, D', also binds to a flanking sequence of the target nucleic acid molecule, and a polymerase (depicted as the cloud) extends the second sequence to generate a complement of the target sequence. Following extension, the probe oligonucleotide may anneal to the target polynucleotide (top of FIG. 3B) or it may anneal to the complementary sequence of the template switching oligonucleotide (bottom of FIG. 3B). Both intermediates exist under thermal equilibrium. A ligase (not shown) covalently attaches the extended complement to the first sequence, C', of the probe oligonucleotide, thereby forming a circular oligonucleotide depicted in FIG. 3C.
Figure 3B:
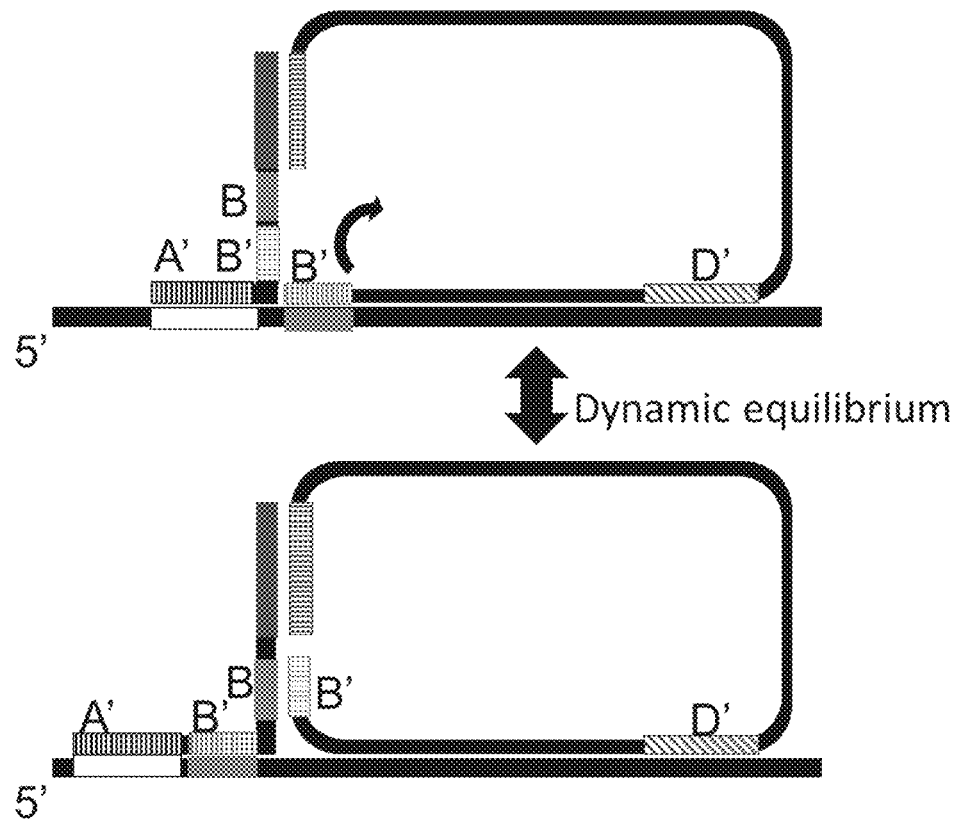
Figure 3C:
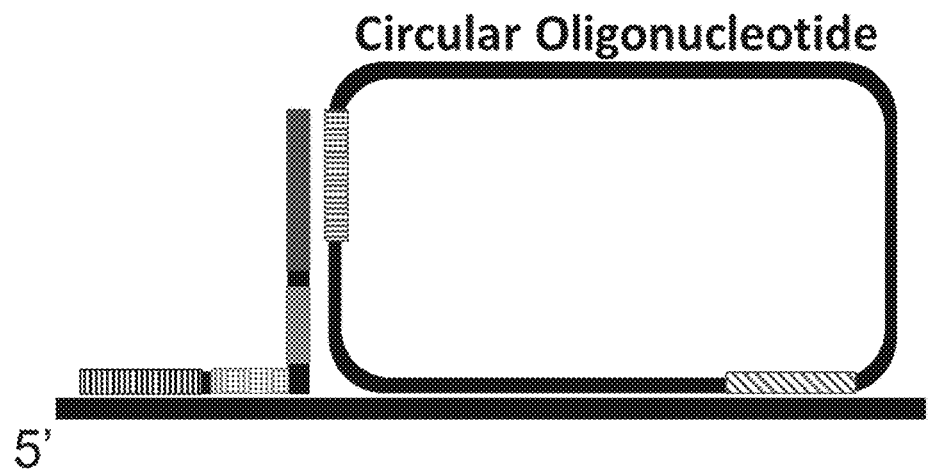
Figure 4:
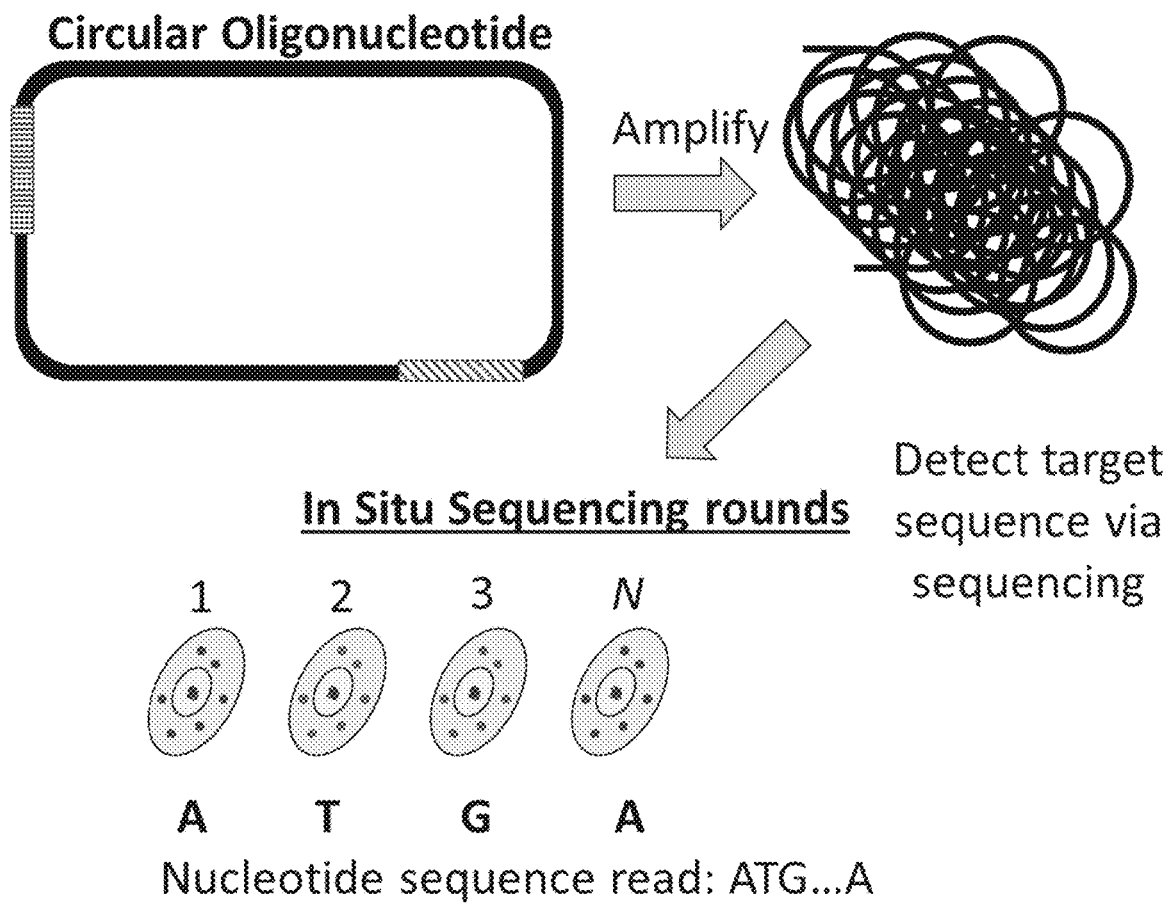
FIG. 4 illustrates an embodiment for detecting the circular oligonucleotide. The circular oligonucleotide may be amplified via rolling circle amplification (RCA) or exponential rolling circle amplification (eRCA). For example, the circular oligonucleotide may be primed with an amplification primer and extended with a strand-displacing polymerase to generate a concatemer containing multiple copies of the target nucleic acid sequence. The target nucleic acid sequence may then be subjected to multiple rounds of in situ sequencing, generated one or more sequencing reads and identifying the target nucleotide sequence.

As used herein, the term "probe oligonucleotide" refers to an oligonucleotide including a sequence complementary to a target polynucleotide and a sequence complementary to blocking oligonucleotide as depicted in FIGS. 2B and 3A. In embodiments, the sequence of the probe oligonucleotide that is complementary to a target polynucleotide includes an extendable 3' end, which may be extended by a polymerase to generate the complement of the target polynucleotide and ligated to the sequence of the probe oligonucleotide that is complementary to the blocking oligonucleotide, as shown in FIGS. 3A-3C, to generate a circular oligonucleotide. The resultant circular oligonucleotide including the sequence of the probe oligonucleotide that is complementary to a target polynucleotide, the complement of the target polynucleotide, and the sequence of the probe oligonucleotide that is complementary to the blocking oligonucleotide may be subjected to rounds of amplification and detection as shown in FIG. 4.

As used herein, the terms "polynucleotide primer" and "primer" refers to any polynucleotide molecule that may hybridize to a polynucleotide template, be bound by a polymerase, and be extended in a template-directed process for nucleic acid synthesis (e.g., amplification and/or sequencing). The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In certain embodiments, a primer has a length of 10 to 150 nucleotides, 15 to 150 nucleotides, 5 to 100 nucleotides, 5 to 50 nucleotides or 10 to 50 nucleotides. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the term "primer binding sequence" refers to a polynucleotide sequence that is complementary to at least a portion of a primer (e.g., a sequencing primer or an amplification primer). Primer binding sequences can be of any suitable length. In embodiments, a primer binding sequence is about or at least about 10, 15, 20, 25, 30, or more nucleotides in length. In embodiments, a primer binding sequence is 10-50, 15-30, or 20-25 nucleotides in length. The primer binding sequence may be selected such that the primer (e.g., sequencing primer) has the preferred characteristics to minimize secondary structure formation or minimize non-specific amplification, for example having a length of about 20-30 nucleotides; approximately 50% GC content, and a Tm of about 55° C. to about 65° C.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, a platform primer is a primer oligonucleotide immobilized or otherwise bound to a solid support (i.e. an immobilized oligonucleotide). Examples of platform primers include P7 and P5 primers (i.e., Illumina® platform sequences), or S1 and S2 primers (i.e., Singular Genomics® platform sequences), or the reverse complements thereof. A "platform primer binding sequence" refers to a sequence or portion of an oligonucleotide that is capable of binding to a platform primer (e.g., the platform primer binding sequence is complementary to the platform primer). In embodiments, a platform primer binding sequence may form part of an adapter. In embodiments, a platform primer binding sequence is complementary to a platform primer sequence. In embodiments, a platform primer binding sequence is complementary to a primer.

The order of elements within a nucleic acid molecule is typically described herein from 5' to 3'. In the case of a double-stranded molecule, the "top" strand is typically shown from 5' to 3', according to convention, and the order of elements is described herein with reference to the top strand.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "coated", "attached", or "immobilized" to one another or to a common solid or semisolid support (e.g. a receiving substrate). An association may refer to a relationship, or connection, between two entities. For example, a barcode sequence may be associated with a particular target by binding a probe including the barcode sequence to the target. In embodiments, detecting the associated barcode provides detection of the target. Associated may refer to the relationship between a sample and the DNA molecules, RNA molecules, or polynucleotides originating from or derived from that sample. These relationships may be encoded in oligonucleotide barcodes, as described herein. A polynucleotide is associated with a sample if it is an endogenous polynucleotide, i.e., it occurs in the sample at the time the sample is obtained, or is derived from an endogenous polynucleotide. For example, the RNAs endogenous to a cell are associated with that cell. cDNAs resulting from reverse transcription of these RNAs, and DNA amplicons resulting from PCR amplification of the cDNAs, contain the sequences of the RNAs and are also associated with the cell. The polynucleotides associated with a sample need not be located or synthesized in the sample, and are considered associated with the sample even after the sample has been destroyed (for example, after a cell has been lysed). Barcoding can be used to determine which polynucleotides in a mixture are associated with a particular sample. In embodiments, a proximity probe is associated with a particular barcode, such that identifying the barcode identifies the probe with which it is associated. Because the proximity probe specifically binds to a target, identifying the barcode thus identifies the target.

The term "adapter" as used herein refers to any oligonucleotide that can be ligated to a nucleic acid molecule, thereby generating nucleic acid products that can be sequenced on a sequencing platform (e.g., an Illumina™ or Singular Genomics G4™ sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In some embodiments, an adapter is hairpin adapter (also referred to herein as a hairpin). In some embodiments, a hairpin adapter includes a single nucleic acid strand including a stem-loop structure. In some embodiments, a hairpin adapter includes a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter includes a stem portion (i.e., stem) and a loop, wherein the stem portion is substantially double stranded thereby forming a duplex. In some embodiments, the loop of a hairpin adapter includes a nucleic acid strand that is not complementary (e.g., not substantially complementary) to itself or to any other portion of the hairpin adapter. In some embodiments, a method herein includes ligating a first adapter to a first end of a double stranded nucleic acid, and ligating a second adapter to a second end of a double stranded nucleic acid. In some embodiments, the first adapter and the second adapter are different. For example, in certain embodiments, the first adapter and the second adapter may include different nucleic acid sequences or different structures. In some embodiments, the first adapter is a Y-adapter and the second adapter is a hairpin adapter. In some embodiments, the first adapter is a hairpin adapter and a second adapter is a hairpin adapter. In certain embodiments, the first adapter and the second adapter may include different primer binding sites, different structures, and/or different capture sequences (e.g., a sequence complementary to a capture nucleic acid). In some embodiments, some, all or substantially all of the nucleic acid sequence of a first adapter and a second adapter are the same. In some embodiments, some, all or substantially all of the nucleic acid sequence of a first adapter and a second adapter are substantially different.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

As used herein, the term "retarding moiety" refers to an element attached to a modified nucleotide that stalls the progression of a polymerase. Examples of retarding moieties include, but are not limited to, modified nucleotide bases (e.g., locked nucleic acids), regions of high GC content (e.g., greater than 50%, 60%, 70%, 80%, or 90% GC content), and/or regions with secondary structure (e.g., stem-loop or hairpin, G-quadruplex, pseudoknot, or cruciform structures). Examples of sequences capable of forming DNA hairpins, pseudoknots, and cruciform are known in the art, and described in, e.g., Baker E et al. J. Phys. Chem. B. 2009; 113(6):1722-7, which is incorporated herein by reference in its entirety). As used herein, a "pseudoknot structure" refers to a structural motif found in RNA that includes two helical motifs connected by single-stranded regions or loops (see, e.g., Staple et al. PLoS Biol. 2005 June; 3(6): e213, which is incorporated herein by reference).

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate moiety of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —$NH_2$, —CN, —$CH_3$, $C_2$-$C_6$ allyl (e.g., —$CH_2$—CH=$CH_2$), methoxyalkyl (e.g., —$CH_2$—O—$CH_3$), or —$CH_2N_3$. In embodiments, the blocking moiety is attached to the 3' oxygen of the nucleotide and is independently

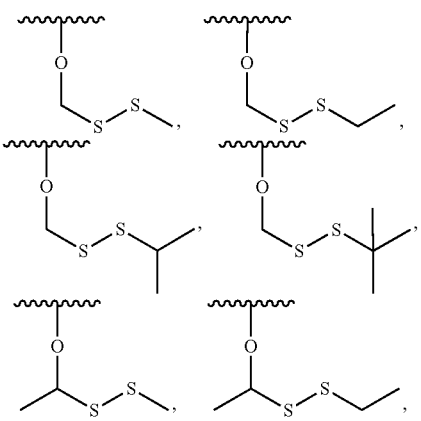

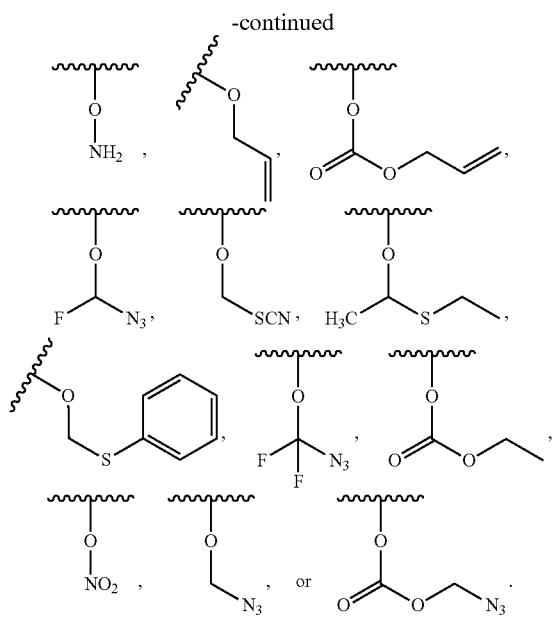

A label moiety of a modified nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes. Non-limiting examples of detectable labels include labels including fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF® dyes (Biotium, Inc.), Alexa Fluor® dyes (Thermo Fisher), DyLight® dyes (Thermo Fisher), Cy® dyes (GE Healthscience), IRDye® dyes (Li-Cor Biosciences, Inc.), and HiLyte™ dyes (Anaspec, Inc.). In embodiments, the label is a fluorophore.

In some embodiments, a nucleic acid includes a label. As used herein, the term "label," "detectable label," or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF® dyes (Biotium, Inc.), Alexa Fluor® dyes (Thermo Fisher), DyLight® dyes (Thermo Fisher), Cy® dyes (GE Healthscience), IRDyes (Li-Cor Biosciences, Inc.), and HiLyte™ dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide includes a label (such as a dye). In embodiments, the label is not associated with any particular nucleotide, but detection of the label identifies whether one or more nucleotides having a known identity were added during an extension step (such as in the case of pyrosequencing). Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa Fluor® dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy®3). In embodiments, the cyanine moiety has 5 methine structures (i.e., cyanine 5 or Cy®5). In embodiments, the cyanine moiety has 7 methine structures (i.e., cyanine 7 or Cy®7).

The term "photocrosslinkable nucleotide" refers, in the usual and customary sense, to a nucleotide including a light-responsive moiety that, upon exposure to a particular wavelength of light, induces the formation of a covalent bond between two nucleotides. Examples of photocrosslinkable nucleotides, include but are not limited to, nucleotides including a carbazole, anthracene moiety, and/or p-stilbazole (see, e.g., Fujimoto et al. Org Lett. 2018 May 18; 20(10):2802-2805).

The term "carbazole" refers, in the usual and customary sense, to a polycyclic aromatic hydrocarbon system including two benzene rings fused between a five-membered nitrogen-containing ring. Structurally, carbazole is family of structures including the following backbone:

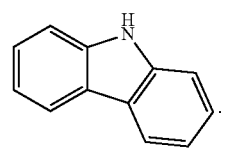 [SMILES: c1ccc2c(c1)[nH]c1ccccc12]

Examples of carbazole, include but are not limited to, 3-cyanovinylcarbazole phosphoramidite, carprofen, and carvediol.

The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "reversible blocking groups" and "reversible terminators" are used in accordance with their plain and ordinary meanings and refer to a blocking moiety located, for example, at the 3' position of a modified nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, WO 96/07669, U.S. Pat. Nos. 7,057,026, 7,541,444, 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethyl reversible terminator. In embodiments, the reversible terminator moiety is attached to the 3'-oxygen of the nucleotide, having the formula:

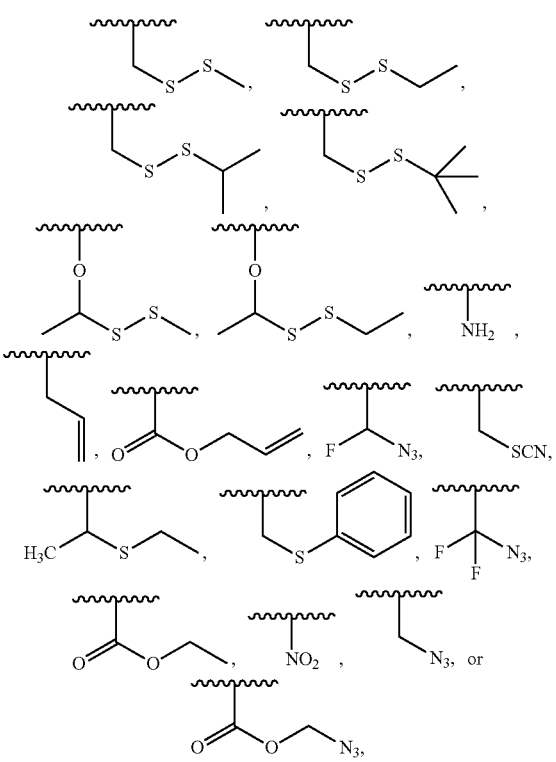

wherein the 3' oxygen of the nucleotide is not shown in the formulae above. The term "allyl" as described herein refers to an unsubstituted methylene attached to a vinyl group (i.e., —CH=$CH_2$). In embodiments, the reversible terminator moiety is

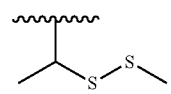

as described in U.S. Pat. No. 10,738,072, which is incorporated herein by reference for all purposes. For example, a nucleotide including a reversible terminator moiety may be represented by the formula:

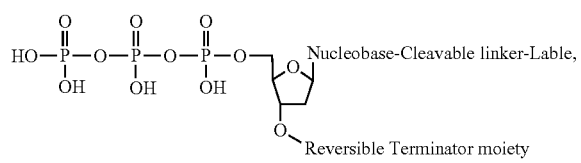

where the nucleobase is adenine or adenine analogue, thymine or thymine analogue, guanine or guanine analogue, or cytosine or cytosine analogue.

In some embodiments, a nucleic acid (e.g., a probe or a primer) includes a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads including the barcode can be identified as originating from a single sample polynucleotide molecule on the basis of the barcode alone. In other embodiments, individual barcode sequences may be used more than once, but adapters including the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined. In embodiments, the barcodes are selected to form a known set of barcodes, e.g., the set of barcodes may be distinguished by a particular Hamming distance. In embodiments, each barcode sequence is unique within the known set of barcodes. In embodiments, each barcode sequence is associated with a particular oligonucleotide.

In embodiments, a nucleic acid (e.g., an adapter or primer) includes a sample barcode. In general, a "sample barcode" is a nucleotide sequence that is sufficiently different from other sample barcode to allow the identification of the sample source based on sample barcode sequence(s) with which they are associated. In embodiments, a plurality of nucleotides (e.g., all nucleotides from a particular sample source, or sub-sample thereof) are joined to a first sample barcode, while a different plurality of nucleotides (e.g., all nucleotides from a different sample source, or different subsample) are joined to a second sample barcode, thereby associating each plurality of polynucleotides with a different sample barcode indicative of sample source. In embodiments, each sample barcode in a plurality of sample barcodes differs from every other sample barcode in the plurality by at least three nucleotide positions, such as at least 3, 4, 5, 6, 7, 8, 9, 10, or more nucleotide positions. In some embodiments, substantially degenerate sample barcodes may be known as random. In some embodiments, a sample barcode may include a nucleic acid sequence from within a pool of known sequences. In some embodiments, the sample barcodes may be pre-defined. In embodiments, the sample barcode includes about 1 to about 10 nucleotides. In embodiments, the sample barcode includes about 3, 4, 5, 6, 7, 8, 9, or about 10 nucleotides. In embodiments, the sample barcode includes about 3 nucleotides. In embodiments, the sample barcode includes about 5 nucleotides. In embodiments, the sample barcode includes about 7 nucleotides. In embodiments, the sample barcode includes about 10 nucleotides. In embodiments, the sample barcode includes about 6 to about 10 nucleotides.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, E. Coli DNA polymerase I, Bacteriophage T4 DNA polymerase, Sequenase™, Taq DNA polymerase, DNA polymerase from Bacillus stearothermophilus, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator™ II, Therminator™ III, or Therminator™ IX) In embodiments, the DNA polymerase is a modified archaeal DNA polymerase. In embodiments, the polymerase is a reverse transcriptase. In embodiments, the polymerase is a mutant P. abyssi polymerase (e.g., such as a mutant P. abyssi polymerase described in WO 2018/148723 or WO 2020/056044). In embodiments, the polymerase is an enzyme described in US 2021/0139884. For example, a polymerase catalyzes the addition of a next correct nucleotide to the 3'-OH group of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator™ II enzyme from New England Biolabs with D141A/E143A/Y409V/A485L mutations); 3'-amino-dNTPs, 3'-azido-dNTPs and other 3'-modified nucleotides (e.g., NEB Therminator™ III DNA Polymerase with D141A/E143A/L408S/Y409A/P410V mutations, NEB Therminator™ IX DNA polymerase), or γ-phosphate labeled nucleotides (e.g., Therminator™ γ: D141A/E143A/W355A/L408 W/R460A/Q461S/K464E/D480V/R484 W/A485L). Typically, these enzymes do not have 5'-3' exonuclease activity. Additional information about thermophilic nucleic acid polymerases may be found in (Southworth M W, et al. *PNAS*. 1996; 93(11):5281-5285; Bergen K, et al. *ChemBioChem*. 2013; 14(9):1058-1062; Kumar S, et al. *Scientific Reports*. 2012; 2:684; Fuller C W, et al. 2016; 113(19):5233-5238; Guo J, et al. *Proceedings of the National Academy of Sciences of the United States of America*. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by an enzyme (e.g. DNA polymerase, a lambda exonuclease, Exo I, Exo III, T5, Exo V, Exo VII or the like). For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, *PNAS Vol* 93, 8281-8285 (1996). In embodiments, 5'-3' exonuclease activity refers to the successive removal of nucleotides in double-stranded DNA in a 5'→3' direction. In embodiments, the 5'-3' exonuclease is lambda exonuclease. For example, lambda exonuclease catalyzes the removal of 5' mononucleotides from duplex DNA, with a preference for 5' phosphorylated double-stranded DNA. In other embodiments, the 5'-3' exonuclease is *E. coli* DNA Polymerase I.

As used herein, the term "ligase" refers to an enzyme that catalyzes the formation of a new phosphodiester bond as a result of joining the 5'-phosphoryl terminus of DNA or RNA to single-stranded 3'-hydroxyl terminus of DNA or RNA. Ligase enzymes can form circular DNA or RNA templates in a non-template driven reaction, and examples of ligase enzymes include, but are not limited to, as CircLigase™, Taq DNA Ligase, HiFi Taq DNA Ligase, T4 ligase, or Ampligase® DNA Ligase.

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "selective" or "selectivity" or the like of a compound refers to the compound's ability to discriminate between molecular targets. For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In embodiments, the template polynucleotide includes a target nucleic acid sequence and one or more barcode sequences. In embodiments, the template polynucleotide is a barcode sequence.

The term "polynucleotide fusion" is used in accordance with its plain and ordinary meaning and refers to a polynucleotide formed from the joining of two regions of a reference sequence (e.g., a reference genome) that are not so joined in the reference sequence, thereby creating a fusion junction between the two regions that does not exist in the reference sequence. Polynucleotide fusions can be formed by a number of processes, including interchromosomal translocation, intrachromosomal translocation, and other chromosomal rearrangements (e.g., inversion and duplication). A polynucleotide fusion can involve fusion between two gene sequences, referred to as a "gene fusion" and producing a "fusion gene." In some cases, a fusion gene is expressed as a fusion transcript (e.g., a fusion mRNA transcript) including sequences of the two genes, or portions thereof.

A "fusion gene" is used in accordance with its ordinary meaning in the art and refers to a hybrid gene, or portion thereof, formed from two previously independent genes, or portions thereof (e.g., in a cell). A "fusion junction" is the point in the fusion gene sequence between the two previously independent genes, or portions thereof. The hybrid gene can result from a translocation, interstitial deletion, and/or chromosomal inversion of a gene or portion of a gene. Chromosomal rearrangements leading to the fusion of coding regions of two genes can result in expression of hybrid proteins. An "exon junction" is the point or location in the fusion gene sequence between the two previously independent exon sequences, or portions thereof.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g., apoptosis or necrosis) or cell shedding, releasing polynucleotides into surrounding body fluids or into circulation. Accordingly, cell-free polynucleotides may be isolated from a non-cellular fraction of blood (e.g., serum or plasma), from other bodily fluids (e.g., urine), or from non-cellular fractions of other types of samples.

As used herein, the terms "specific", "specifically", "specificity", or the like of a compound refers to the compound's ability to cause a particular action, such as binding, to a particular molecular target with minimal or no action to other proteins in the cell.

The terms "attached," "bind," and "bound" as used herein are used in accordance with their plain and ordinary meanings and refer to an association between atoms or molecules. The association can be direct or indirect. For example, attached molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

"Specific binding" is where the binding is selective between two molecules. A particular example of specific binding is that which occurs between an antibody and an antigen. Typically, specific binding can be distinguished from non-specific when the dissociation constant (KD) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. In embodiments, the KD (equilibrium dissociation constant) between two specific binding molecules is less than $10^{-6}$ M, less than $10^{-7}$ M, less than $10^{-8}$ M, less than $10^{-9}$ M, less than $10^{-10}$ M, less than $10^{-11}$ M, or less than about 1012 M or less.

As used herein, the terms "sequencing", "sequence determination", "determining a nucleotide sequence", and the like include determination of a partial or complete sequence information (e.g., a sequence) of a polynucleotide being sequenced, and particularly physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein includes contacting a template and an annealed primer with a suitable polymerase under conditions suitable for polymerase extension and/or sequencing.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers.

As used herein, the term "substrate" refers to a solid support material. The substrate can be non-porous or porous. The substrate can be rigid or flexible. As used herein, the terms "solid support" and "solid surface" refers to discrete solid or semi-solid surface. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A nonporous substrate generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor®, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located within a flow cell. Solid surfaces can also be varied in their shape depending on the application in a method described herein. For example, a solid surface useful herein can be planar, or contain regions which are concave or convex. In embodiments, the geometry of the concave or convex regions (e.g., wells) of the solid surface conform to the size and shape of the particle to maximize the contact between as substantially circular particle. In embodiments, the wells of an array are randomly located such that nearest neighbor features have random spacing between each other. Alternatively, in embodiments the spacing between the wells can be ordered, for example, forming a regular pattern. The term solid substrate is encompassing of a substrate (e.g., a flow cell) having a surface including a polymer coating covalently attached thereto. In embodiments, the solid substrate is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate includes a surface (e.g., a surface of a flow cell, a surface of a tube, a surface of a chip), for example a metal surface (e.g., steel, gold, silver, aluminum, silicon and copper). In embodiments a substrate (e.g., a substrate surface) is coated and/or includes functional groups and/or inert materials. In certain embodiments a substrate includes a bead, a chip, a capillary, a plate, a membrane, a wafer (e.g., silicon wafers), a comb, or a pin for example. In some embodiments a substrate includes a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In embodiments a substrate includes a magnetic material (e.g., iron, nickel, cobalt, platinum, aluminum, and the like). In embodiments a substrate includes a magnetic bead (e.g., DYNABEADS®, hematite, AMPure® XP). Magnets can be used to purify and/or capture nucleic acids bound to certain substrates (e.g., substrates including a metal or magnetic material). The flow cell is typically a glass slide containing small fluidic channels (e.g., a glass slide 75 mm×25 mm×1 mm having one or more channels), through which sequencing solutions (e.g., polymerases, nucleotides, and buffers) may traverse. Though typically glass, suitable flow cell materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, the material of the flow cell is selected due to the ability to conduct thermal energy. In embodiments, a flow cell includes inlet and outlet ports and a flow channel extending there between.

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "microplate", or "multiwell container" as used herein, refers to a substrate including a surface, the surface including a plurality of reaction chambers separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modern robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides in a cell.

The reaction chambers may be provided as wells of a multiwell container (alternatively referred to as reaction chambers), for example a microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 5-7 mm. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 6 mm.

The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate are available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells.

The discrete regions (i.e., features, wells) of the microplate may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a polymer or copolymer).

As used herein, the term "sequencing reaction mixture" is used in accordance with its plain and ordinary meaning and refers to an aqueous mixture that contains the reagents necessary to allow dNTP or dNTP analogue (e.g., a modified nucleotide) to add a nucleotide to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. In embodiments, one nucleotide (e.g., a modified nucleotide) is incorporated per sequencing cycle. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes, and other substances can be removed between steps by washing. Cycles may include repeating these steps, and the sequence of each cluster is read over the multiple repetitions.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence. In embodiments, a sequencing read includes reading a barcode and not a template nucleotide sequence. Reads of length 20-40 base pairs (bp) are referred to as ultra-short. Typical sequencers produce read lengths in the range of 100-500 bp. Read length is a factor which can affect the results of biological studies. For example, longer read lengths improve the resolution of de novo genome assembly and detection of structural variants. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read includes a computationally derived string corresponding to the detected label. In some embodiments, a sequencing read may include 300, 400, 500, 600, 700, 800, 900, 1,000, 1,100, 1,200, 1,300, 1,400, 1,500, or more nucleotide bases.

The term "multiplexing" as used herein refers to an analytical method in which the presence and/or amount of multiple targets, e.g., multiple nucleic acid target sequences, can be assayed simultaneously by using the methods and devices as described herein, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic. As used herein, the term "multiplex" is used to refer to an assay in which multiple (i.e. at least two) different biomolecules are assayed at the same time, and more particularly in the same aliquot of the sample, or in the same reaction mixture. In embodiments, more than two different biomolecules are assayed at the same time. In embodiments, at least 2, 4, 6, 8, 10, 20, 50, 100, 200, 300, 400, 500, 600, 700, 800, 900, 1000, 1100, 1200, 1300, 1400 or 1500 or more biomolecules are detected according to the present method.

Complementary single stranded nucleic acids and/or substantially complementary single stranded nucleic acids can hybridize to each other under hybridization conditions, thereby forming a nucleic acid that is partially or fully double stranded. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often include nucleic acid sequences that are substantially complementary to each other.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acids. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which includes a double stranded portion of nucleic acid.

As used herein, the term "adjacent," refers to two nucleotide sequences in a nucleic acid, can refer to nucleotide sequences separated by 0 to about 20 nucleotides, more specifically, in a range of about 1 to about 10 nucleotides, or to sequences that directly abut one another. As those of skill in the art appreciate, two nucleotide sequences that that are to ligated together will generally directly abut one another.

A nucleic acid can be amplified by a suitable method. The term "amplification," "amplified" or "amplifying" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof (which may be referred to herein as an "amplification product" or "amplification products"). In some embodiments an amplification reaction includes a suitable thermal stable polymerase. Thermal stable polymerases are known and are stable for prolonged periods of time, at temperature greater than 80° C. when compared to common polymerases found in most mammals. In certain embodiments the term "amplification," "amplified" or "amplifying" refers to a method that includes a polymerase chain reaction (PCR). Conditions conducive to amplification (i.e., amplification conditions) are known and often include at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, bridge-PCR (bPCR) amplification is a method for solid-phase amplification as exemplified by the disclosures of U.S. Pat. Nos. 5,641,658; 7,115,400; and U.S. Patent Publ. No. 2008/0009420, each of which is incorporated herein by reference in its entirety. Bridge-PCR involves repeated polymerase chain reaction cycles, cycling between denaturation, annealing, and extension conditions and enables controlled, spatially-localized, amplification, to generate amplification products (e.g., amplicons) immobilized on a solid support in order to form arrays including colonies (or "clusters") of immobilized nucleic acid molecule.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA (oligonucleotide ligation assay)/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8, Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification includes at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can include thermocycling or can be performed isothermally.

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers including tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification includes a nucleic acid amplification reaction including only one species of oligonucleotide primer immobilized to a surface or substrate. In certain embodiments solid phase amplification includes a plurality of different immobilized oligonucleotide primer species. In some embodiments solid phase amplification may include a nucleic acid amplification reaction including one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge PCR amplification, emulsion PCR, WildFire amplification (e.g., US patent publication US20130012399), the like or combinations thereof.

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/cm$^2$, at least about 1,000 features/cm$^2$, at least about 10,000 features/cm$^2$, at least about 100,000 features/cm$^2$, at least about 10,000,000 features/cm$^2$, at least about 100,000,000 features/cm$^2$, at least about 1,000,000,000 features/cm$^2$, at least about 2,000,000,000 features/cm$^2$ or higher. In embodiments, the arrays have features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by at least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can include nucleic acids obtained from one or more subjects. In some embodiments a sample includes nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation.

As used herein, the term "disease state" is used in accordance with its plain and ordinary meaning and refers to any abnormal biological or aberrant state of a cell. The presence of a disease state may be identified by the same collection of biological constituents used to determine the cell's biological state. In general, a disease state will be detrimental to a biological system. A disease state may be a consequence of, inter alia, an environmental pathogen, for example a viral infection (e.g., HIV/AIDS, hepatitis B, hepatitis C, influenza, measles, etc.), a bacterial infection, a parasitic infection, a fungal infection, or infection by some other organism. A disease state may also be the consequence of some other environmental agent, such as a chemical toxin or a chemical carcinogen. As used herein, a disease state further includes genetic disorders wherein one or more copies of a gene is altered or disrupted, thereby affecting its biological function. Exemplary genetic diseases include, but are not limited to polycystic kidney disease, familial multiple endocrine neoplasia type I, neurofibromatoses, Tay-Sachs disease, Huntington's disease, sickle cell anemia, thalassemia, and Down's syndrome, as well as others (see, e.g., The Metabolic and Molecular Bases of Inherited Diseases, 7th ed., McGraw-Hill Inc., New York). Other exemplary diseases include, but are not limited to, cancer, hypertension, Alzheimer's disease, neurodegenerative diseases, and neuropsychiatric disorders such as bipolar affective disorders or paranoid schizophrenic disorders. Disease states are monitored to determine the level or severity (e.g., the stage or progression) of one or more disease states of a subject and, more specifically, detect changes in the biological state of a subject which are correlated to one or more disease states (see, e.g., U.S. Pat. No. 6,218,122, which is incorporated by reference herein in its entirety). In embodiments, methods provided herein are also applicable to monitoring the disease state or states of a subject undergoing one or more therapies. Thus, the present disclosure also provides, in some embodiments, methods for determining or monitoring efficacy of a therapy or therapies (i.e., determining a level of therapeutic effect) upon a subject. In embodiments, methods of the present disclosure can be used to assess therapeutic efficacy in a clinical trial, e.g., as an early surrogate marker for success or failure in such a clinical trial. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result in compensatory changes in a wide number of other proteins. In particular, the partial disruption of even a single protein within a cell, such as by exposure to a drug or by a disease state which modulates the gene copy number (e.g., a genetic mutation), results in characteristic compensatory changes in the transcription of enough other genes that these changes in transcripts can be used to define a "signature" of particular transcript alterations which are related to the disruption of function, e.g., a particular disease state or therapy, even at a stage where changes in protein activity are undetectable.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A protein may refer to a protein expressed in a cell.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

The term "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes.

A "gene" refers to a polynucleotide that is capable of conferring biological function after being transcribed and/or translated. Functionally, a genome is subdivided into genes. Each gene is a nucleic acid sequence that encodes an RNA or polypeptide. A gene is transcribed from DNA into RNA, which can either be non-coding (ncRNA) with a direct function, or an intermediate messenger (mRNA) that is then translated into protein. Typically a gene includes multiple sequence elements, such as for example, a coding element (i.e., a sequence that encodes a functional protein), non-coding element, and regulatory element. Each element may be as short as a few bp to 5 kb. In embodiments, the gene is the protein coding sequence of RNA. Non-limiting examples of genes include developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABL1, BCL1, BCL2, BCL6, CBFA2, CBL, CSF1R, ERBA, ERBB, ERBB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3, and YES); tumor suppressor genes (e.g., APC, BRCA1, BRCA2, MADH4, MCC, NF1, NF2, RB1, TP53, and WT1); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases). In embodiments, a gene includes at least one mutation associated with a disease or condition mediated by a mutant form of the gene.

As used herein, the terms "biomolecule" or "analyte" refer to an agent (e.g., a compound, macromolecule, or small molecule), and the like derived from a biological system (e.g., an organism, a cell, or a tissue). The biomolecule may contain multiple individual components that collectively construct the biomolecule, for example, in embodiments, the biomolecule is a polynucleotide wherein the polynucleotide is composed of nucleotide monomers. The biomolecule may be or may include DNA, RNA, organelles, carbohydrates, lipids, proteins, or any combination thereof. These components may be extracellular. In some examples, the biomolecule may be referred to as a clump or aggregate of combinations of components. In some instances, the biomolecule may include one or more constituents of a cell but may not include other constituents of the cell. In embodiments, a biomolecule is a molecule produced by a biological system (e.g., an organism). The biomolecule may be any substance (e.g. molecule) or entity that is desired to be detected by the method of the invention. The biomolecule is the "target" of the assay method of the invention. The biomolecule may accordingly be any compound that may be desired to be detected, for example a peptide or protein, or nucleic acid molecule or a small molecule, including organic and inorganic molecules. The biomolecule may be a cell or a microorganism, including a virus, or a fragment or product thereof. Biomolecules of particular interest may thus include proteinaceous molecules such as peptides, polypeptides, proteins or prions or any molecule which includes a protein or polypeptide component, etc., or fragments thereof. The biomolecule may be a single molecule or a complex that contains two or more molecular subunits, which may or may not be covalently bound to one another, and which may be the same or different. Thus, in addition to cells or microorganisms, such a complex biomolecule may also be a protein complex. Such a complex may thus be a homo- or heteromultimer. Aggregates of molecules e.g., proteins may also be target analytes, for example aggregates of the same protein or different proteins. The biomolecule may also be a complex between proteins or peptides and nucleic acid molecules such as DNA or RNA. Of particular interest may be the interactions between proteins and nucleic acids, e.g., regulatory factors, such as transcription factors, and interactions between DNA or RNA molecules.

As used herein, "biomaterial" refers to any biological material produced by an organism. In some embodiments, biomaterial includes secretions, extracellular matrix, proteins, lipids, organelles, membranes, cells, portions thereof, and combinations thereof. In some embodiments, cellular material includes secretions, extracellular matrix, proteins, lipids, organelles, membranes, cells, portions thereof, and combinations thereof. In some embodiments, biomaterial includes viruses. In some embodiments, the biomaterial is a replicating virus and thus includes virus infected cells. In embodiments, a biological sample includes biomaterials.

In some embodiments, a sample includes one or more nucleic acids, or fragments thereof. A sample can include nucleic acids obtained from one or more subjects. In some embodiments a sample includes nucleic acid obtained from a single subject. In some embodiments, a sample includes a mixture of nucleic acids. A mixture of nucleic acids can include two or more nucleic acid species having different nucleotide sequences, different fragment lengths, different origins (e.g., genomic origins, cell or tissue origins, subject origins, the like or combinations thereof), or combinations thereof. A sample may include synthetic nucleic acid.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

The methods and kits of the present disclosure may be applied, mutatis mutandis, to the sequencing of RNA, or to determining the identity of a ribonucleotide.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits. Vessels may include any structure capable of supporting or containing a liquid or solid material and may include, tubes, vials, jars, containers, tips, etc. In embodiments, a wall of a vessel may permit the transmission of light through the wall. In embodiments, the vessel may be optically clear. The kit may include the enzyme and/or nucleotides in a buffer.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
| --- | --- | --- |
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

An "antibody" (Ab) is a protein that binds specifically to a particular substance, known as an "antigen" (Ag). An "antibody" or "antigen-binding fragment" is an immunoglobulin that binds a specific "epitope." The term encompasses polyclonal, monoclonal, and chimeric antibodies. In nature, antibodies are generally produced by lymphocytes in response to immune challenge, such as by infection or immunization. An "antigen" (Ag) is any substance that reacts specifically with antibodies or T lymphocytes (T cells). An antibody may include the entire antibody as well as any antibody fragments capable of binding the antigen or antigenic fragment of interest. Examples include complete antibody molecules, antibody fragments, such as Fab, F(ab')2, CDRs, VL, VH, and any other portion of an antibody which is capable of specifically binding to an antigen. Antibodies used herein are immunospecific for, and therefore specifically and selectively bind to, for example, proteins either detected (e.g., biological targets of interest) or used for detection (e.g., probes containing oligonucleotide barcodes) in the methods and devices as described herein.

The term "covalent linker" is used in accordance with its ordinary meaning and refers to a divalent moiety which connects at least two moieties to form a molecule.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

As used herein a "genetically modifying agent" is a substance that alters the genetic sequence of a cell following exposure to the cell, resulting in an agent-mediated nucleic acid sequence. In embodiments, the genetically modifying agent is a small molecule, protein, pathogen (e.g., virus or bacterium), toxin, oligonucleotide, or antigen. In embodiments, the genetically modifying agent is a virus (e.g., influenza) and the agent-mediated nucleic acid sequence is the nucleic acid sequence that develops within a T-cell upon cellular exposure and contact with the virus. In embodiments, the genetically modifying agent modulates the expression of a nucleic acid sequence in a cell relative to a control (e.g., the absence of the genetically modifying agent).

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

As used herein, the term "upstream" refers to a region in the nucleic acid sequence that is towards the 5' end of a particular reference point, and the term "downstream" refers to a region in the nucleic acid sequence that is toward the 3' end of the reference point.

As used herein, the terms "incubate," and "incubation" refer collectively to altering the temperature of an object in a controlled manner such that conditions are sufficient for conducting the desired reaction. Thus, it is envisioned that the terms encompass heating a receptacle (e.g., a microplate) to a desired temperature and maintaining such temperature for a fixed time interval. Also included in the terms is the act of subjecting a receptacle to one or more heating and cooling cycles (i.e., "temperature cycling" or "thermal cycling"). While temperature cycling typically occurs at relatively high rates of change in temperature, the term is not limited thereto, and may encompass any rate of change in temperature.

As used herein, "biological activity" may include the in vivo activities of a compound or physiological responses that result upon in vivo administration of a compound, composition or other mixture. Biological activity, thus, may encompass therapeutic effects and pharmaceutical activity of such compounds, compositions and mixtures. Biological activities may be observed in vitro systems designed to test or use such activities.

The term "isolated" means altered or removed from the natural state. For example, a nucleic acid or a polypeptide naturally present in a living animal is not isolated, but the same nucleic acid or polypeptide partially or completely separated from the coexisting materials of its natural state is isolated. An isolated nucleic acid or protein can exist in substantially purified form, or can exist in a non-native environment such as, for example, a host cell. In embodiments, "isolated" refers to a nucleic acid, polynucleotide, polypeptide, protein, or other component that is partially or completely separated from components with which it is normally associated (other proteins, nucleic acids, cells, etc.).

The term "synthetic target" as used herein refers to a modified protein or nucleic acid such as those constructed by synthetic methods. In embodiments, a synthetic target is artificial or engineered, or derived from or contains an artificial or engineered protein or nucleic acid (e.g., non-natural or not wild type). For example, a polynucleotide that is inserted or removed such that it is not associated with nucleotide sequences that normally flank the polynucleotide as it is found in nature is a synthetic target polynucleotide.

The term "nucleic acid sequencing device" and the like means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, for the purpose of determining the nucleic acid sequence of a template polynucleotide. Nucleic acid sequencing devices may further include valves, pumps, and specialized functional coatings on interior walls. Nucleic acid sequencing devices may include a receiving unit, or platen, that orients the flow cell such that a maximal surface area of the flow cell is available to be exposed to an optical lens. Other nucleic acid sequencing devices include those provided by Singular Genomics™ (e.g., the G4™ system), Illumina™ (e.g., HiSeq™, MiSeq™ NextSeq™, or NovaSeq™ systems), Life Technologies™ (e.g., ABI PRISM™, or SOLiD™ systems), Pacific Biosciences (e.g., systems using SMRT™ Technology such as the Sequel™ or RS II™ systems), or Qiagen (e.g., Genereader™ system). Nucleic acid sequencing devices may further include fluidic reservoirs (e.g., bottles), valves, pressure sources, pumps, sensors, control systems, valves, pumps, and specialized functional coatings on interior walls. In embodiments, the device includes a plurality of a sequencing reagent reservoirs and a plurality of clustering reagent reservoirs. In embodiments, the clustering reagent reservoir includes amplification reagents (e.g., an aqueous buffer containing enzymes, salts, and nucleotides, denaturants, crowding agents, etc.) In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of each of the reservoirs can vary. The fluid can be, for example, an aqueous solution which may contain buffers (e.g., saline-sodium citrate (SSC), ascorbic acid, tris(hydroxymethyl)aminomethane or "Tris"), aqueous salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes. In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). In embodiments, the nucleic acid sequencing device includes an imaging system (e.g., an imaging system as described herein). The imaging system capable of exciting one or more of the identifiable labels (e.g., a fluorescent label) linked to a nucleotide and thereafter obtain image data for the identifiable labels. The image data (e.g., detection data) may be analyzed by another component within the device. The imaging system may include a system described herein and may include a fluorescence spectrophotometer including an objective lens and/or a solid-state imaging device. The solid-state imaging device may include a charge coupled device (CCD) and/or a complementary metal oxide semiconductor (CMOS). The system may also include circuitry and processors, including systems using microcontrollers, reduced instruction set computers (RISC), application specific integrated circuits (ASICs), field programmable gate array (FPGAs), logic circuits, and any other circuit or processor capable of executing functions described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. In embodiments, the device includes a thermal control assembly useful to control the temperature of the reagents.

The term "image" is used according to its ordinary meaning and refers to a representation of all or part of an object. The representation may be an optically detected reproduction. For example, an image can be obtained from fluorescent, luminescent, scatter, or absorption signals. The part of the object that is present in an image can be the surface or other xy plane of the object. Typically, an image is a 2 dimensional representation of a 3 dimensional object. An image may include signals at differing intensities (i.e., signal levels). An image can be provided in a computer readable format or medium. An image is derived from the collection of focus points of light rays coming from an object (e.g., the sample), which may be detected by any image sensor.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2 dimensional area defined by straight line axes x and y. When used in reference to a detecting apparatus and an object observed by the detector, the xy plane may be specified as being orthogonal to the direction of observation between the detector and object being detected.

As used herein, the term "tissue section" refers to a piece of tissue that has been obtained from a subject, optionally fixed and attached to a surface, e.g., a microscope slide.

The term "clonotype" is used in accordance with its ordinary meaning in the art and refers to a recombined nucleic acid which encodes an immune receptor or a portion thereof. For example, a clonotype refers to a recombined nucleic acid, usually extracted from a T cell or B cell, but which may also be from a cell-free source, which encodes a T cell receptor (TCR) or B cell receptor (BCR), or a portion thereof. In embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCRγ, a VDJ rearrangement of TCR δ, a VD rearrangement of TCR δ, a Kde-V rearrangement, or the like. Clonotypes may also encode translocation breakpoint regions involving immune receptor genes, such as Bcl1-JH or Bcl2-JH. In one aspect, clonotypes have sequences that are sufficiently long to represent or reflect the diversity of the immune molecules that they are derived from consequently, clonotypes may vary widely in length. In some embodiments, clonotypes have lengths in the range of from 25 to 400 nucleotides; in other embodiments, clonotypes have lengths in the range of from 25 to 200 nucleotides.

A "immune repertoire" refers to the collection of T cell receptors and B cell receptors (e.g., immunoglobulin) that constitutes an organism's adaptive immune system.

A "locus" is used in accordance with its ordinary meaning and refers to a location of a gene or other DNA sequence on a chromosome. The Immunoglobulin Heavy (IGH) locus refers to a collection of located on chromosome 14 and is responsible for the production of heavy chain immunoglobulins, composed of several sub-loci, including V, D, J, C and S regions, which are involved in the process of antibody diversity. The IGH locus is responsible for the production of IgM, IgD, IgG, IgE, and IgA. The Immunoglobulin Kappa (IGK) locus refers to a collection of genes located on chromosome 2 and is responsible for the production of kappa light chain immunoglobulins, composed of V, J, and C regions, which are involved in the process of antibody diversity. The IGK locus is responsible for the production of IgM, IgD, IgG, IgE, and IgA. The Immunoglobulin Lambda (IGL) locus refers to a collection of genes located on chromosome 22 and is responsible for the production of lambda light chain immunoglobulins, composed of V, J, and C regions, which are involved in the process of antibody diversity.

By aqueous solution herein is meant a liquid including at least 20 vol % water. In embodiments, aqueous solution includes at least 50%, for example at least 75 vol %, at least 95 vol %, above 98 vol %, or 100 vol % of water as the continuous phase.

As used herein, the term "code," means a system of rules to convert information, such as signals obtained from a detection apparatus, into another form or representation, such as a base call or nucleic acid sequence. For example, signals that are produced by one or more incorporated nucleotides can be encoded by a digit. The digit can have several potential values, each value encoding a different signal state. For example, a binary digit will have a first value for a first signal state and a second value for a second signal state. A digit can have a higher radix including, for example, a ternary digit having three potential values, a quaternary digit having four potential values, etc. A series of digits can form a codeword. The length of the codeword is the same as the number of sequencing steps performed. Exemplary codes include, but are not limited to, a Hamming code. A Hamming code is used in accordance with its ordinary meaning in computer science, mathematics, telecommunication sciences and refers to a code that can be used to detect and correct the errors that can occur when the data is moved or stored. The Hamming distance refers to the difference in integer number between two codewords of equal length, and may be determined using known techniques in the art such as the Hamming distance test or the Hamming distance algorithm. For example, for two codewords (i.e., two sequenced barcodes that have been converted to a string of integers), a difference of 0 indicates that the codewords (i.e., the sequences) are identical. A difference of 1 in integer value indicates a Hamming distance of 1, thus 1 base difference between the oligos. Hamming distance is the number of positions for which the corresponding bit values in the two strings are different. In other words, the test measures the minimum number of substitutions that would be necessary to change one bit string into the other.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Methods

In an aspect is provided a method of profiling a sample (e.g., a cell or tissue). In embodiments, the method includes determining and/or obtaining information (e.g., gene and protein expression) about the transcriptome of an organism thus elucidating subcellular substances and processes while gaining valuable spatial localization information within a cell. In embodiments, the method includes simultaneously sequencing a plurality of nucleic acids, such as RNA transcripts, in situ within an optically resolved volume of a sample (e.g., a voxel). RNA transcripts are responsible for the process of converting DNA into an organism's phenotype, thus by determining the types and quantity of RNA present in a sample (e.g., a cell), it is possible to assign a phenotype to the cell. RNA transcripts include coding RNA and non-coding RNA molecules, such as messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA).

In an aspect is provided a method of forming a circular oligonucleotide, optionally in a cell or tissue (e.g., in situ). In embodiments, the method includes contacting a target polynucleotide complex (e.g., wherein the target polynucleotide complex is in a cell, on a cell, or in a tissue) with a probe oligonucleotide, thereby forming a probe polynucleotide complex, wherein the target polynucleotide complex includes a blocking oligonucleotide bound to a first sequence of a target polynucleotide, wherein the blocking oligonucleotide includes a probe hybridization sequence, and wherein the probe polynucleotide complex includes the probe oligonucleotide bound to a second sequence of the target polynucleotide and bound to the probe hybridization sequence, wherein the target sequence is between the first and second sequence; extending the probe oligonucleotide along the target sequence with a polymerase to generate an extension strand including a complementary sequence of the target sequence, and ligating the extension strand to the probe oligonucleotide hybridization sequence, thereby generating a circular oligonucleotide. In embodiments, the method includes amplifying and detecting the circular oligonucleotide. In embodiments, the method includes forming the circular oligonucleotide on a first device, isolating the circular oligonucleotide from the first device and sequencing the circular oligonucleotide (e.g., ex situ sequencing) on a different device. In embodiments, the target polynucleotide complex is in a cell. In embodiments, the target polynucleotide complex is on a cell. In embodiments, the target polynucleotide complex is in a tissue (e.g., kidney, lung, breast, colon, skin, or placenta tissue).

In another aspect is provided a method of amplifying a target sequence, the method including: contacting a target polynucleotide complex with a probe oligonucleotide, thereby forming a probe polynucleotide complex, wherein the target polynucleotide complex includes a blocking oligonucleotide bound to a first sequence of a target polynucleotide, wherein the blocking oligonucleotide includes a probe hybridization sequence, and wherein the probe polynucleotide complex includes the probe oligonucleotide bound to a second sequence of the target polynucleotide and bound to the probe hybridization sequence, wherein the target sequence is between the first and second sequence; extending the probe oligonucleotide along the target sequence with a polymerase to generate an extension strand including a complement of the target sequence, and ligating the extension strand to the probe oligonucleotide hybridization sequence, thereby generating a circular oligonucleotide; and amplifying the circular oligonucleotide by extending an amplification primer hybridized to the circular oligonucleotide with a strand-displacing polymerase, thereby generating an amplification product including multiple copies of the target sequence.

In yet another aspect is provided a method of detecting a nucleic acid molecule in or on a cell, the method including amplifying the target sequence of the nucleic acid molecule as described herein, and sequencing the target sequence in or on the cell, thereby detecting the nucleic acid molecule.

In embodiments, the target polynucleotide complex is formed by contacting the target polynucleotide (e.g., a target mRNA molecule or target nucleic acid bound to an antibody) with a blocking oligonucleotide including a first target hybridization sequence and a probe hybridization sequence, and hybridizing the first target hybridization sequence to the target polynucleotide.

In embodiments, the target polynucleotide complex is in a cell or tissue. In embodiments, the cell forms part of a tissue in situ. In embodiments, the cell is an isolated single cell. In embodiments, the cell is a prokaryotic cell. In embodiments, the cell is a eukaryotic cell. In embodiments, the cell is a bacterial cell (e.g., a bacterial cell or bacterial spore), a fungal cell (e.g., a fungal spore), a plant cell, or a mammalian cell. In embodiments, the cell is a stem cell. In embodiments, the stem cell is an embryonic stem cell, a tissue-specific stem cell, a mesenchymal stem cell, or an induced pluripotent stem cell. In embodiments, the cell is an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage. In embodiments, the cell is a stem cell, an immune cell, a cancer cell (e.g., a circulating tumor cell or cancer stem cell), a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the cell is a genetically modified cell. In embodiments, the cell is a circulating tumor cell or cancer stem cell.

In embodiments, the cell is a prokaryotic cell. In embodiments, the cell is a bacterial cell. In embodiments, the bacterial cell is a *Bacteroides, Clostridium, Faecalibacterium, Eubacterium*, Ruminococcus, Peptococcus, *Peptostreptococcus*, or *Bifidobacterium* cell. In embodiments, the bacterial cell is a *Bacteroides fragilis, Bacteroides melaninogenicus, Bacteroides oralis, Enterococcus faecalis, Escherichia coli, Enterobacter sp., Klebsiella sp., Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enterica, Faecalibacterium prausnitzii, Peptostreptococcus sp., or Peptococcus sp.* cell. In embodiments, the cell is a fungal cell. In embodiments, the fungal cell is a *Candida, Saccharomyces, Aspergillus, Penicillium, Rhodotorula, Trametes, Pleospora, Sclerotinia, Bullera*, or a *Galactomyces* cell.

In embodiments, the cell is a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a Hepadnaviridae, Adenoviridae, Herpesviridae, Poxviridae, Parvoviridae, Reoviridae, Coronaviridae, Retroviridae virus.

In embodiments, the cell is an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. In embodiments, the cell is a neuronal cell, an endothelial cell, epithelial cell, germ cell, plasma cell, a muscle cell, peripheral blood mononuclear cell (PBMC), a myocardial cell, or a retina cell. In embodiments, the cell is a suspension cell (e.g., a cell free-floating in the culture medium, such a lymphoblast or hepatocyte). In embodiments, the cell is a glial cell (e.g., astrocyte, radial glia), pericyte, or stem cell (e.g., a neural stem cell). In embodiments, the cell is a neuronal cell. In embodiments, the cell is an endothelial cell. In embodiments, the cell is an epithelial cell. In embodiments, the cell is a germ cell. In embodiments, the cell is a plasma cell. In embodiments, the cell is a muscle cell. In embodiments, the cell is a peripheral blood mononuclear cell (PBMC). In embodiments, the cell is a myocardial cell. In embodiments, the cell is a retina cell. In embodiments, the cell is a lymphoblast. In embodiments, the cell is a hepatocyte. In embodiments, the cell is a glial cell. In embodiments, the cell is an astrocyte. In embodiments, the cell is a radial glia. In embodiments, the cell is a pericyte. In embodiments, the cell is a stem cell. In embodiments, the cell is a neural stem cell.

In embodiments, the cell is bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the cell is an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the immune cell is a granulocyte. In embodiments, the immune cell is a mast cell. In embodiments, the immune cell is a monocyte. In embodiments, the immune cell is a neutrophil. In embodiments, the immune cell is a dendritic cell. In embodiments, the immune cell is a natural killer (NK) cell. In embodiments, the immune cell is a T cell. In embodiments, the immune cell is a B cell. In embodiments, the cell includes a T cell receptor gene sequence. In embodiments, the cell includes a B cell receptor gene sequence. In embodiments, the cell includes an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the cell is a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a HER2 gene. In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cell is permeabilized and immobilized to a solid support.

In embodiments, the blocking oligonucleotide is covalently bound to the target polynucleotide.

In embodiments, the blocking oligonucleotide includes a first target hybridization sequence and a probe hybridization sequence. In embodiments, the blocking oligonucleotide includes a first target hybridization sequence, a first curl sequence, a second curl sequence, and a probe hybridization sequence, wherein the first curl sequence is complementary to the second curl sequence. In embodiments, the blocking oligonucleotide further includes one or more spacer sequence (e.g., a synthetic sequence not complementary to the probe or the target polynucleotide. In embodiments, the blocking oligonucleotide includes, from 3' to 5', a sequence complementary to the target polynucleotide, a first curl sequence, a second curl sequence, a spacer sequence, and a probe hybridization sequence, wherein the first curl sequence is complementary to the second curl sequence. In embodiments, the first curl sequence is complementary to a sequence of the target polynucleotide. In embodiments, the spacer sequence includes about 5 to about 20 nucleotides. In embodiments, the spacer sequence includes about 5, 10, 15, or 20 nucleotides. In embodiments, each nucleotide of the spacer sequence is the same (e.g., all the nucleotides of the spacer sequence consist of adenine, thymine, cytosine, or guanine).

In embodiments, the blocking oligonucleotide includes a first target hybridization sequence including 5 to 100 nucleotides and a probe hybridization sequence including 5 to 100 nucleotides. In embodiments, the blocking oligonucleotide is about 50 to about 500 nucleotides in length. In embodiments, the blocking oligonucleotide is about 50 to about 300 nucleotides in length. In embodiments, the blocking oligonucleotide is about 80 to about 300 nucleotides in length. In embodiments, the blocking oligonucleotide is about 50 to about 150 nucleotides in length. In embodiments, the blocking oligonucleotide is about or more than about 40, 50, 75, 100, 125, 150, 175, 200, 250, 300, 350, 400, or 500 nucleotides in length. In embodiments, the blocking oligonucleotide is less than about 50, 75, 100, 125, 150, 175, 200, 250, 300, 350, 400, or 500 nucleotides in length.

In embodiments, the probe oligonucleotide includes a second target hybridization sequence and a blocking hybridization sequence. In embodiments, the probe oligonucleotide includes a second target hybridization sequence including 5 to 100 nucleotides and a blocking hybridization sequence including 5 to 100 nucleotides. In embodiments, the probe oligonucleotide is about 50 to about 500 nucleotides in length. In embodiments, the probe oligonucleotide is about 50 to about 300 nucleotides in length. In embodiments, the probe oligonucleotide is about 80 to about 300 nucleotides in length. In embodiments, the probe oligonucleotide is about 50 to about 150 nucleotides in length. In embodiments, the probe oligonucleotide is about or more than about 40, 50, 75, 100, 125, 150, 175, 200, 250, 300, 350, 400, or 500 nucleotides in length. In embodiments, the probe oligonucleotide is less than about 50, 75, 100, 125, 150, 175, 200, 250, 300, 350, 400, or 500 nucleotides in length.

In embodiments, the second target hybridization sequence is a random sequence. As used herein, the term "random" in the context of a synthetic nucleic acid sequence refers to a sequence where one or more nucleotides has an equal probability of being present upon synthesis. In embodiments, one or more nucleotides is selected at random from a set of two or more different nucleotides at one or more positions, with each of the different nucleotides selected at one or more positions represented in a pool of oligonucleotides including the random sequence. For example, a random sequence may be represented by a sequence composed of N's, where N can be any nucleotide (e.g., A, T, C, or G). For example, a four base random sequence may have the sequence NNNN, where the Ns can independently be any nucleotide (e.g., AATC or GTCA). In embodiments, a pool of barcodes may be represented by a fully random sequence, with the caveat that certain sequences have been excluded (e.g., runs of three or more nucleotides of the same type, such as "AAA" or "GGG"). In embodiments, nucleotide positions that are allowed to vary (e.g., by two, three, or four nucleotides) may be separated by one or more fixed positions (e.g., as in "NGN"). In embodiments, the second target hybridization sequence is a random sequence including 4 to 30 nucleotides. In embodiments, the second target hybridization sequence is a random sequence including about 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In embodiments, the probe hybridization sequence includes 5 to 25 nucleotides. In embodiments, the probe hybridization sequence is about 5 to about 35 nucleotides in length. In embodiments, the probe hybridization sequence is about 12 to 15 nucleotides in length. In embodiments, the probe hybridization sequence is about 15 to 30 nucleotides in length. In embodiments, the probe hybridization sequence is about 5, 6, 7, 8, 9, 10, 11, 12, 13, 14, 15, 16, 17, 18, 19, 20, 21, 22, 23, 24, 25, 26, 27, 28, 29, or 30 nucleotides in length.

In embodiments, the target hybridization sequence (e.g., the first and/or second target hybridization sequence) is greater than 30 nucleotides. In embodiments, the target hybridization sequence is about 5 to about 35 nucleotides in length. In embodiments, the target hybridization sequence is about 12 to 15 nucleotides in length. In embodiments, the target hybridization sequence is about 35 to 40 nucleotides in length to maximize specificity. In embodiments, the target hybridization sequence is greater than 12 nucleotides in length. In embodiments, the target hybridization sequence is about 5, about 10, about 15, about 20, about 25, about 30, or about 35 nucleotides in length. In embodiments, the target hybridization sequence is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In embodiments, the target hybridization sequence of each oligonucleotide primer is a single stranded polynucleotide that is at least 50% complementary, at least 75% complementary, at least 85% complementary, at least 90% complementary, at least 95% complementary, at least 98%, at least 99% complementary, or 100% complementary to a portion of a target polynucleotide.

In embodiments, the first target hybridization sequence (alternatively referred to as flanking-target-region) of the oligonucleotide primer or the second target hybridization sequence (alternatively referred to as flanking-target-region) of the oligonucleotide primer includes about 5 to about 15 nucleotides. In embodiments, the first target hybridization sequence (alternatively referred to as flanking-target-region) of the oligonucleotide primer or the second target hybridization sequence (alternatively referred to as flanking-target-region) of the oligonucleotide primer includes about 10 to about 25 nucleotides. In embodiments, the first target hybridization sequence (alternatively referred to as flanking-target-region) of the oligonucleotide primer or the second target hybridization sequence (alternatively referred to as flanking-target-region) of the oligonucleotide primer includes about 10 to about 20 nucleotides. In embodiments, the first target hybridization sequence (alternatively referred to as flanking-target-region) of the oligonucleotide primer or the second target hybridization sequence (alternatively referred to as flanking-target-region) of the oligonucleotide primer includes about 15 to about 25 nucleotides. In embodiments, the first target hybridization sequence of the oligonucleotide primer or the second target hybridization sequence of the oligonucleotide primer includes about 3 to about 5 nucleotides. In embodiments, the first target hybridization sequence of the oligonucleotide primer includes about 3 to about 5 nucleotides and second target hybridization sequence of the oligonucleotide primer includes about 6 to about 10 nucleotides. In embodiments, the first target hybridization sequence of the oligonucleotide primer includes about 10 to about 15 nucleotides and the second target hybridization sequence of the oligonucleotide primer includes about 15 to about 30 nucleotides. In embodiments, the first target hybridization sequence includes at least one target-specific region. In embodiments, the second target hybridization sequence includes at least one target-specific region. A target-specific region is a single stranded polynucleotide that is at least 50% complementary, at least 75% complementary, at least 85% complementary, at least 90% complementary, at least 95% complementary, at least 98%, at least 99% complementary, or 100% complementary to a portion of a nucleic acid molecule that includes a target sequence (e.g., a gene of interest). In embodiments, the target-specific region is capable of hybridizing to at least a portion of the target sequence. In embodiments, the target-specific region is substantially non-complementary to other target sequences present in the sample. In embodiments, the length of the first target hybridization sequence and second target hybridization sequence are the same length (e.g., both the first and the second target hybridization sequences are each about 15 nucleotides). In embodiments, the length of the first target hybridization sequence and second target hybridization sequence are different lengths (e.g., the first target hybridization sequence is about 10 nucleotides and the second target hybridization sequence is about 20 nucleotides). In embodiments, an asymmetric oligonucleotide primer (i.e., an oligonucleotide primer having a first target hybridization sequence and second target hybridization sequence that are different lengths) may be advantageous in preventing non-specific hybridization. In embodiments, the total length of the first target hybridization sequence and second target hybridization sequence combined is about 25, 30, 35, or 40 nucleotides. In embodiments, the total length of the first domain and second domain is combined about 30 to 40 nucleotides.

In embodiments, the target hybridization sequence of each probe (e.g., each probe of a plurality of probes) is complementary to different portions of the same target polynucleotide. In embodiments, the target hybridization sequence of each probe (e.g., each probe of a plurality of probes) is complementary to different portions of different target polynucleotides. In embodiments, the target hybridization sequence of each probe is complementary to portions of the same target polynucleotide that are separated by about 10 to about 500 nucleotides. In embodiments, the target hybridization sequence of each probe are complementary to portions of the same target polynucleotide that are separated by about 10, about 15, about 20, about 25, about 30, about 35, about 40, about 45, about 50, about 75, about 100, about 125, about 150, about 175, about 200, about 225, about 250, about 275, about 300, about 325, about 350, about 375, about 400, about 425, about 450, about 475, or about 500 nucleotides. In embodiments, the target hybridization sequence of each probe is complementary to portions of the same target polynucleotide that are separated by about or more than about 10, 15, 20, 25, 30, 35, 40, 45, 50, 75, 100, 125, 150, 175, 200, 225, 250, 275, 300, 325, 350, 375, 400, 425, 450, 475, or 500 nucleotides.

In embodiments, the probe hybridization sequence is greater than 30 nucleotides. In embodiments, the probe hybridization sequence is about 5 to about 35 nucleotides in length. In embodiments, the probe hybridization sequence is about 12 to 15 nucleotides in length. In embodiments, the probe hybridization sequence is about 35 to 40 nucleotides in length. In embodiments, the probe hybridization sequence is about 40 to 50 nucleotides in length. In embodiments, the probe hybridization sequence is greater than 50 nucleotides in length. In embodiments, the probe hybridization sequence is about 5, about 10, about 15, about 20, about 25, about 30, about 35, about 40, about 45, or about 50 nucleotides in length.

In embodiments, the first curl sequence is about 4 to 15 nucleotides. In embodiments, the first curl sequence is about 5 to about 35 nucleotides in length. In embodiments, the first curl sequence is about 12 to 15 nucleotides in length. In embodiments, the first curl sequence is about 15 to 30 nucleotides in length. In embodiments, the second curl sequence is about 4 to 15 nucleotides. In embodiments, the second curl sequence is about 5 to about 35 nucleotides in length. In embodiments, the second curl sequence is about 12 to 15 nucleotides in length. In embodiments, the second curl sequence is about 15 to 30 nucleotides in length. In embodiments, the first curl sequence is about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length. In embodiments, the second curl sequence is about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length.

In embodiments, the blocking oligonucleotide includes one or more modified nucleotide(s). In embodiments, the modified nucleotide includes a retarding moiety covalently bound to the modified nucleotide. In embodiments, the first target hybridization sequence and/or the second target hybridization sequence includes one or more modified nucleotide(s). In embodiments, the modified nucleotide includes one or more locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), phosphorothioate nucleic acids, Zip nucleic acids (ZNAs), or combinations thereof. In embodiments, the first target hybridization sequence includes one or more locked nucleic acids (LNAs), Zip nucleic acids (ZNAs), 2-amino-deoxyadenosine (2-amino-dA), trimethoxystilbene-functionalized oligonucleotides (TFOs), Pyrene-functionalized oligonucleotides (PFOs), peptide nucleic acids (PNAs), or aminoethyl-phenoxazine-dC (AP-dC) nucleic acids.

In embodiments, the first target hybridization sequence and/or the second target hybridization sequence includes one or more locked nucleic acid (LNA) nucleotides. In embodiments, the first target hybridization sequence and the second target hybridization sequence includes one or more LNA nucleotides. In embodiments, the first target hybridization sequence includes one or more locked nucleic acid (LNA) nucleotides. In embodiments, the second target hybridization sequence includes one or more locked nucleic acid (LNA) nucleotides. In embodiments, the first target hybridization sequence includes one locked nucleic acid (LNA) nucleotide. In embodiments, the second target hybridization sequence includes one locked nucleic acid (LNA) nucleotide.

In embodiments, the first target hybridization sequence and/or the second target hybridization sequence includes a plurality of LNAs interspersed throughout the target hybridization sequence. In embodiments, the first target hybridization sequence includes a plurality of LNAs interspersed throughout the target hybridization sequence. In embodiments, the second target hybridization sequence includes a plurality of LNAs interspersed throughout the target hybridization sequence. In embodiments, the plurality of LNAs includes consecutive (i.e., adjacent) LNA nucleotides.

In embodiments, the first target hybridization sequence and/or the second target hybridization sequence includes Bis-locked nucleic acids (bisLNAs). In embodiments, the first target hybridization sequence includes Bis-locked nucleic acids (bisLNAs). In embodiments, the second target hybridization sequence includes Bis-locked nucleic acids (bisLNAs). In embodiments, the first target hybridization sequence and/or the second target hybridization sequence includes twisted intercalating nucleic acids (TINAs). In embodiments, the first target hybridization sequence includes twisted intercalating nucleic acids (TINAs). In embodiments, the second target hybridization sequence includes twisted intercalating nucleic acids (TINAs). In embodiments, the first target hybridization sequence and/or the second target hybridization sequence includes bridged nucleic acids (BNAs). In embodiments, the first target hybridization sequence includes bridged nucleic acids (BNAs). In embodiments, the second target hybridization sequence includes bridged nucleic acids (BNAs). In embodiments, the first target hybridization sequence and/or the second target hybridization sequence includes 2'-O-methyl RNA:DNA chimeric nucleic acids. In embodiments, the first target hybridization sequence includes 2'-O-methyl RNA:DNA chimeric nucleic acids. In embodiments, the second target hybridization sequence includes 2'-O-methyl RNA:DNA chimeric nucleic acids. In embodiments, the first target hybridization sequence and/or the second target hybridization sequence includes minor groove binder (MGB) nucleic acids. In embodiments, the first target hybridization sequence includes minor groove binder (MGB) nucleic acids. In embodiments, the second target hybridization sequence includes minor groove binder (MGB) nucleic acids. In embodiments, the first target hybridization sequence and/or the second target hybridization sequence includes morpholino nucleic acids. In embodiments, the first target hybridization sequence includes morpholino nucleic acids. In embodiments, the second target hybridization sequence includes morpholino nucleic acids. Morpholino nucleic acids are synthetic nucleotides that have standard nucleic acid bases (e.g., adenine, guanine, cytosine, and thymine) wherein those bases are bound to methylenemorpholine rings linked through phosphorodiamidate groups instead of phosphates. Morpholino nucleic acids may be referred to as phosphorodiamidate morpholino oligomers (PMOs). In embodiments, the first target hybridization sequence and/or the second target hybridization sequence includes C5-modified pyrimidine nucleic acids. In embodiments, the first target hybridization sequence includes C5-modified pyrimidine nucleic acids. In embodiments, the second target hybridization sequence includes C5-modified pyrimidine nucleic acids. In embodiments, the first target hybridization sequence and/or the second target hybridization sequence includes peptide nucleic acids (PNAs). In embodiments, the first target hybridization sequence includes peptide nucleic acids (PNAs). In embodiments, the second target hybridization sequence includes peptide nucleic acids (PNAs). In embodiments, the first target hybridization sequence and/or the second target hybridization sequence includes from 5' to 3' a plurality of synthetic nucleotides (e.g., LNAs) followed by a plurality (e.g., 2 to 5) canonical or native nucleotides (e.g., dNTPs). In embodiments, the first target hybridization sequence includes from 5' to 3' a plurality of synthetic nucleotides (e.g., LNAs) followed by a plurality (e.g., 2 to 5) canonical or native nucleotides (e.g., dNTPs). In embodiments, the second target hybridization sequence includes from 5' to 3' a plurality of synthetic nucleotides (e.g., LNAs) followed by a plurality (e.g., 2 to 5) canonical or native nucleotides (e.g., dNTPs). In embodiments, the first target hybridization sequence and/or the second target hybridization sequence includes one or more (e.g., 2 to 5) deoxyuracil nucleobases (dU). In embodiments, the first target hybridization sequence includes one or more (e.g., 2 to 5) deoxyuracil nucleobases (dU). In embodiments, the second target hybridization sequence includes one or more (e.g., 2 to 5) deoxyuracil nucleobases (dU). In embodiments, the one or more dU nucleobases are at or near the 3' end of the target hybridization sequence and/or probe sequence (e.g., within 5 nucleotides of the 3' end). In embodiments, the one or more dU nucleobases are at or near the 3' end of the target hybridization sequence. In embodiments, the one or more dU nucleobases are at or near the 3' end of the probe sequence (e.g., within 5 nucleotides of the 3' end). In embodiments, the first target hybridization sequence and/or the second target hybridization sequence includes from 5' to 3' a plurality (e.g., 2 to 5) of phosphorothioate nucleic acids, followed by a plurality of synthetic nucleotides (e.g., LNAs), and subsequently followed by a plurality (e.g., 2 to 5) of canonical nucleobases. In embodiments, the first target hybridization sequence includes from 5' to 3' a plurality (e.g., 2 to 5) of phosphorothioate nucleic acids, followed by a plurality of synthetic nucleotides (e.g., LNAs), and subsequently followed by a plurality (e.g., 2 to 5) of canonical nucleobases. In embodiments, the second target hybridization sequence includes from 5' to 3' a plurality (e.g., 2 to 5) of phosphorothioate nucleic acids, followed by a plurality of synthetic nucleotides (e.g., LNAs), and subsequently followed by a plurality (e.g., 2 to 5) of canonical nucleobases. In some embodiments, the target hybridization sequence and/or probe sequence includes a plurality of canonical nucleobases, wherein the canonical nucleobases terminate (i.e., at the 3' end) with a deoxyuracil nucleobase (dU). In some embodiments, the target hybridization sequence includes a plurality of canonical nucleobases, wherein the canonical nucleobases terminate (i.e., at the 3' end) with a deoxyuracil nucleobase (dU). In some embodiments, the probe sequence includes a plurality of canonical nucleobases, wherein the canonical nucleobases terminate (i.e., at the 3' end) with a deoxyuracil nucleobase (dU).

In embodiments, the first target hybridization sequence and/or the second target hybridization sequence includes a plurality of LNAs interspersed throughout the polynucleotide. In embodiments, the first target hybridization sequence and/or the second target hybridization sequence includes a plurality of consecutive LNAs (e.g., 2 to 5 LNAs, 5 to 7 LNAs, or 7 to 10 LNAs) throughout the target hybridization sequence and/or probe sequence. In embodiments, the entire composition of the first target hybridization sequence and/or the second target hybridization sequence includes less than 70%, less than 60%, less than 50%, less than 40%, less than 30%, less than 20%, less than 10%, or less than 5% of LNAs. In embodiments, the entire composition of the first target hybridization sequence and/or the second target hybridization sequence includes up to about 70%, up to about 60%, up to about 50%, up to about 40%, up to about 30%, up to about 20%, up to about 10%, or up to about 5% of LNAs. In embodiments, the entire composition of the first target hybridization sequence and/or the second target hybridization sequence includes more than 60%, more than 50%, more than 40%, more than 30%, more than 20%, more than 10%, or more than 5% of LNAs. In embodiments, the entire composition of the first target hybridization sequence and/or the second target hybridization sequence includes about 5% to about 10%, about 10% to about 20%, about 20% to about 30%, about 30% to about 40%, about 40% to about 50%, about 50% to about 60%, or about 60% to about 70% of LNAs. In embodiments, the entire composition of the first target hybridization sequence includes about 5% to about 10%, about 10% to about 20%, about 20% to about 30%, about 30% to about 40%, about 40% to about 50%, about 50% to about 60%, or about 60% to about 70% of LNAs. In embodiments, the entire composition of the second target hybridization sequence includes about 5% to about 10%, about 10% to about 20%, about 20% to about 30%, about 30% to about 40%, about 40% to about 50%, about 50% to about 60%, or about 60% to about 70% of LNAs. In embodiments, the entire composition of the first target hybridization sequence and/or the second target hybridization sequence includes about 5%, about 10%, about 15%, about 20%, about 25%, about 30%, about 35%, about 40%, about 45%, about 50%, about 55%, about 60%, about 65%, or about 70% of LNAs. In embodiments, the entire composition of the first target hybridization sequence includes about 5%, about 10%, about 15%, about 20%, about 25%, about 30%, about 35%, about 40%, about 45%, about 50%, about 55%, about 60%, about 65%, or about 70% of LNAs. In embodiments, the entire composition of the second target hybridization sequence includes about 5%, about 10%, about 15%, about 20%, about 25%, about 30%, about 35%, about 40%, about 45%, about 50%, about 55%, about 60%, about 65%, or about 70% of LNAs. In embodiments, the entire composition of the first target hybridization sequence and/or the second target hybridization sequence includes about 30%, about 35%, about 40%, about 45%, about 50%, about 55%, about 60%, about 65%, about 70%, about 75%, about 80%, about 85%, about 90%, or about 95% of canonical dNTPs. In embodiments, the entire composition of the first target hybridization sequence includes about 30%, about 35%, about 40%, about 45%, about 50%, about 55%, about 60%, about 65%, about 70%, about 75%, about 80%, about 85%, about 90%, or about 95% of canonical dNTPs. In embodiments, the entire composition of the second target hybridization sequence includes about 30%, about 35%, about 40%, about 45%, about 50%, about 55%, about 60%, about 65%, about 70%, about 75%, about 80%, about 85%, about 90%, or about 95% of canonical dNTPs. In embodiments, the entire composition of the first target hybridization sequence and/or the second target hybridization sequence includes less than 95%, less than 90%, less than 80%, less than 70%, less than 60%, less than 50%, less than 40%, or less than 30% of canonical dNTPs. In embodiments, the entire composition of the first target hybridization sequence and/or the second target hybridization sequence includes up to about 95%, up to about 90%, up to about 80%, up to about 70%, up to about 60%, up to about 50%, up to about 40%, or up to about 30% of canonical dNTPs. In embodiments, the entire composition of the first target hybridization sequence and/or the second target hybridization sequence includes more than 90%, more than 80%, more than 70%, more than 60%, more than 50%, more than 40%, or more than 30% of canonical dNTPs.

In embodiments, the entire composition of the first target hybridization sequence and/or the second target hybridization sequence includes about 70% of LNAs and about 30% of canonical dNTPs. In embodiments, the entire composition of the first target hybridization sequence includes about 70% of LNAs and about 30% of canonical dNTPs. In embodiments, the entire composition of the second target hybridization sequence includes about 70% of LNAs and about 30% of canonical dNTPs. In embodiments, the entire composition of the first target hybridization sequence and/or the second target hybridization sequence includes about 65% of LNAs and about 35% of canonical dNTPs. In embodiments, the entire composition of the first target hybridization sequence includes about 65% of LNAs and about 35% of canonical dNTPs. In embodiments, the entire composition of the second target hybridization sequence includes about 65% of LNAs and about 35% of canonical dNTPs. In embodiments, the entire composition of the first target hybridization sequence and/or the second target hybridization sequence includes about 60% of LNAs and about 40% of canonical dNTPs. In embodiments, the entire composition of the first target hybridization sequence includes about 60% of LNAs and about 40% of canonical dNTPs. In embodiments, the entire composition of the second target hybridization sequence includes about 60% of LNAs and about 40% of canonical dNTPs. In embodiments, the entire composition of the first target hybridization sequence and/or the second target hybridization sequence includes about 55% of LNAs and about 45% of canonical dNTPs. In embodiments, the entire composition of the first target hybridization sequence includes about 55% of LNAs and about 45% of canonical dNTPs. In embodiments, the entire composition of the second target hybridization sequence includes about 55% of LNAs and about 45% of canonical dNTPs. In embodiments, the entire composition of the first target hybridization sequence and/or the second target hybridization sequence includes about 50% of LNAs and about 50% of canonical dNTPs. In embodiments, the entire composition of the first target hybridization sequence includes about 50% of LNAs and about 50% of canonical dNTPs. In embodiments, the entire composition of the second target hybridization sequence includes about 50% of LNAs and about 50% of canonical dNTPs. In embodiments, the entire composition of the first target hybridization sequence and/or the second target hybridization sequence includes about 45% of LNAs and about 55% of canonical dNTPs. In embodiments, the entire composition of the first target hybridization sequence includes about 45% of LNAs and about 55% of canonical dNTPs. In embodiments, the entire composition of the second target hybridization sequence includes about 45% of LNAs and about 55% of canonical dNTPs. In embodiments, the entire composition of the first target hybridization sequence and/or the second target hybridization sequence includes about 40% of LNAs and about 60% of canonical dNTPs. In embodiments, the entire composition of the first target hybridization sequence includes about 40% of LNAs and about 60% of canonical dNTPs. In embodiments, the entire composition of the second target hybridization sequence includes about 40% of LNAs and about 60% of canonical dNTPs. In embodiments, the entire composition of the first target hybridization sequence and/or the second target hybridization sequence includes about 35% of LNAs and about 65% of canonical dNTPs. In embodiments, the entire composition of the first target hybridization sequence includes about 35% of LNAs and about 65% of canonical dNTPs. In embodiments, the entire composition of the second target hybridization sequence includes about 35% of LNAs and about 65% of canonical dNTPs. In embodiments, the entire composition of the first target hybridization sequence and/or the second target hybridization sequence includes about 30% of LNAs and about 70% of canonical dNTPs. In embodiments, the entire composition of the first target hybridization sequence includes about 30% of LNAs and about 70% of canonical dNTPs. In embodiments, the entire composition of the second target hybridization sequence includes about 30% of LNAs and about 70% of canonical dNTPs. In embodiments, the entire composition of the first target hybridization sequence and/or the second target hybridization sequence includes about 25% of LNAs and about 75% of canonical dNTPs. In embodiments, the entire composition of the first target hybridization sequence includes about 25% of LNAs and about 75% of canonical dNTPs. In embodiments, the entire composition of the second target hybridization sequence includes about 25% of LNAs and about 75% of canonical dNTPs. In embodiments, the entire composition of the first target hybridization sequence and/or the second target hybridization sequence includes about 20% of LNAs and about 80% of canonical dNTPs. In embodiments, the entire composition of the first target hybridization sequence includes about 20% of LNAs and about 80% of canonical dNTPs. In embodiments, the entire composition of the second target hybridization sequence includes about 20% of LNAs and about 80% of canonical dNTPs. In embodiments, the entire composition of the first target hybridization sequence and/or the second target hybridization sequence includes about 15% of LNAs and about 85% of canonical dNTPs. In embodiments, the entire composition of the first target hybridization sequence includes about 15% of LNAs and about 85% of canonical dNTPs. In embodiments, the entire composition of the second target hybridization sequence includes about 15% of LNAs and about 85% of canonical dNTPs. In embodiments, the entire composition of the first target hybridization sequence and/or the second target hybridization sequence includes about 10% of LNAs and about 90% of canonical dNTPs. In embodiments, the entire composition of the first target hybridization sequence includes about 10% of LNAs and about 90% of canonical dNTPs. In embodiments, the entire composition of the second target hybridization sequence includes about 10% of LNAs and about 90% of canonical dNTPs. In embodiments, the entire composition of the first target hybridization sequence and/or the second target hybridization sequence includes about 5% of LNAs and about 95% of canonical dNTPs. In embodiments, the entire composition of the first target hybridization sequence includes about 5% of LNAs and about 95% of canonical dNTPs. In embodiments, the entire composition of the second target hybridization sequence includes about 5% of LNAs and about 95% of canonical dNTPs.

In embodiments, the first target hybridization sequence of the blocking oligonucleotide includes one or more (e.g., 3, 4, 5, 6, 7, 8 or more) photocrosslinkable nucleotide(s). In embodiments, the photocrosslinkable nucleotide includes a carbazole moiety. In embodiments, the photocrosslinkable nucleotide is 3-cyanovinylcarbazole phosphoramidite. In embodiments, prior to forming the probe polynucleotide complex, the method includes exposing the target polynucleotide complex to UV light thereby covalently binding the blocking oligonucleotide to the target polynucleotide. In embodiments, prior to forming the probe polynucleotide complex, the method includes exposing the target polynucleotide complex to wavelengths between about 365 nm to about 405 nm thereby covalently binding the blocking oligonucleotide to the target polynucleotide. In embodiments, prior to forming the probe polynucleotide complex, the method includes exposing the target polynucleotide complex to a wavelength of about 365 nm thereby covalently binding the blocking oligonucleotide to the target polynucleotide. In embodiments, prior to forming the probe polynucleotide complex, the method includes exposing the target polynucleotide complex to a wavelength of about 405 nm thereby covalently binding the blocking oligonucleotide to the target polynucleotide. In embodiments, prior to forming the probe polynucleotide complex, the method includes exposing the target polynucleotide complex to a wavelength of about 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, 400 nm, 401 nm, 402 nm, 403 nm, 404 nm, or 405 nm, thereby covalently binding the blocking oligonucleotide to the target polynucleotide. For example, 5-azido-2'-deoxyuridine triphosphate (5-azido-dUTP) is a commonly used photoreactive nucleotide. Benzophenone moieties can be attached to nucleotides and are activated by UV light (typically around 365 nm). Upon activation, they form a diradical that can react with C—H bonds, forming stable covalent bonds. An example is benzophenone-4'-carbonyl-2'-deoxyuridine triphosphate. Diazirines are small, photoactivatable groups that generate reactive carbenes upon exposure to UV light (usually around 350-370 nm). These carbenes can insert into C—H, N—H, and O—H bonds to form stable covalent bonds. An example of such a nucleotide is 3-trifluoromethyl-3-phenyldiazirine-derivatized deoxyuridine triphosphate.

In embodiments, the probe oligonucleotide is approximately 50 to 200 nucleotides. In embodiments, the probe oligonucleotide has a first domain that is capable of hybridizing to a first target sequence domain, and a second domain, capable of hybridizing to a target nucleic acid sequence-adjacent second sequence domain. In embodiments, following hybridization there is a gap between the first target sequence domain, and the second domain, wherein the gap spans the length of the target nucleic acid sequence. In embodiments, the probe oligonucleotide has a first domain that is capable of hybridizing to a first target sequence domain, and a second domain capable of hybridizing to a second target sequence domain. In embodiments, the length of the first domain and second domain are the same length (e.g., both the first and the second domains are about 15 nucleotides). In embodiments, the length of the first domain and second domain are different lengths (e.g., the first domain is about 10 nucleotides and the second domain is about 20 nucleotides). In embodiments, an asymmetric probe oligonucleotide (i.e., a probe oligonucleotide having a first domain and second domain that are different sequence lengths) may be advantageous in preventing non-specific hybridization. In embodiments, the total length of the first domain and second domain is about 25, 30, 35, or 40 nucleotides. In embodiments, the total length of the first domain and second domain is about 30 nucleotides. In embodiments, the total length of the first domain and second domain is about 15 to 25 nucleotides. In embodiments, the total length of the first domain is about 15 to 25 nucleotides and the total length of the second domain is about 20 to 25 nucleotides.

In embodiments, the probe oligonucleotide further includes a barcode sequence. In embodiments, the second target hybridization sequence may be used as a barcode sequence (e.g., sequencing all or a portion of the second target hybridization sequence) to identify the circular oligonucleotide. In embodiments, the method includes sequencing the probe hybridization sequence, or a complement thereof. In embodiments, the method includes sequencing the first curl sequence, or a complement thereof, or the second curl sequence, or a complement thereof. In embodiments, the barcode (i.e., the barcode sequence) is at least 5, 6, 7, 8, 9, 10, 11, 12, 13, 14, or 15 nucleotides in length. In embodiments, the barcode is 5, 6, 7, 8, 9, 10, 11, 12, 13, 14, or 15 nucleotides in length. In embodiments, the barcode is 10 to 15 nucleotides in length. In embodiments, the barcode is at least about 1, 2, 3, 4, 5, 6, 7, 8, 9, 10, 15, 20, 25, 30, 35, 40, 45, 50 or more nucleotides in length. In embodiments, the barcode can be at most about 300, 200, 100, 90, 80, 70, 60, 50, 40, 30, 20, 15, 12, 10, 9, 8, 7, 6, 5, 4 or fewer or more nucleotides in length. In embodiments, the barcode includes between about 5 to about 8, about 5 to about 10, about 5 to about 15, about 5 to about 20, about 10 to about 150 nucleotides. In embodiments, the barcode includes between 5 to 8, 5 to 10, 5 to 15, 5 to 20, 10 to 150 nucleotides. In embodiments, the barcode is 10 nucleotides.

In embodiments, the barcode may include a unique sequence (e.g., a barcode sequence) that gives the barcode its identifying functionality. The unique sequence may be random or non-random. In embodiments, the barcode is known (i.e., the nucleic sequence is known before sequencing) and is sorted into a basis-set according to their Hamming distance. Oligonucleotide barcodes (e.g., barcode sequences included in an oligonucleotide) can be associated with a target of interest by knowing, a priori, the target of interest, such as a gene or protein. In embodiments, the barcodes further include one or more sequences capable of specifically binding a gene or nucleic acid sequence of interest. For example, in embodiments, the barcode includes a sequence capable of hybridizing to mRNA, e.g., one containing a poly-T sequence (e.g., having several T's in a row, e.g., 4, 5, 6, 7, 8, or more T's).

In embodiments, the barcode is included as part of an oligonucleotide of longer sequence length, such as a primer or a random sequence (e.g., a random N-mer). In embodiments, the barcode contains random sequences to increase the mass or size of the oligonucleotide tag. The random sequence can be of any suitable length, and there may be one or more than one present. As non-limiting examples, the random sequence may have a length of 10 to 40, 10 to 30, 10 to 20, 25 to 50, 15 to 40, 15 to 30, 20 to 50, 20 to 40, or 20 to 30 nucleotides. In embodiments, each barcode sequence is selected from a known set of barcode sequences. In embodiments, each of the known set of barcode sequences is associated with a target hybridization sequence from a known set of target hybridization sequences. In embodiments, a first barcode sequence is associated with a first target hybridization sequence, and wherein a second barcode sequence is associated with a second target hybridization sequence (e.g., wherein the second target hybridization sequence is included in an oligonucleotide targeting a different target nucleic acid than the first target hybridization sequence). In embodiments, the same barcode sequence is associated with a plurality of oligonucleotides targeting different sequences of the same target nucleic acid (e.g., the same target polynucleotide).

In embodiments, ligating includes chemical ligation (e.g., enzyme-free, click-mediated ligation). In embodiments, the oligonucleotide primer includes a first bioconjugate reactive moiety capable of bonding upon contact with a second (complementary) bioconjugate reactive moiety. In embodiments, the oligonucleotide primer includes an alkynyl moiety at the 3' and an azide moiety at the 5' end that, upon hybridization to the target nucleic acid react to form a triazole linkage during suitable reaction conditions. Reaction conditions and protocols for chemical ligation techniques that are compatible with nucleic acid amplification methods are known in the art, for example El-Sagheer, A. H., & Brown, T. (2012). *Accounts of chemical research*, 45(8), 1258-1267; Manuguerra I. et al. *Chem Commun* (Camb). 2018; 54(36):4529-4532; and Odeh, F., et al. (2019). *Molecules* (Basel, Switzerland), 25(1), 3, each of which is incorporated herein by reference in their entirety.

In embodiments, ligating includes covalently binding adjacent sequences with a ligase. In embodiments, the ligase is a pre-adenylated ligase. In embodiments, the ligase is a PBCV-1 DNA Ligase. In embodiments, the ligase is a TS2126 RNA ligase. In embodiments, ligating includes enzymatic ligation including a ligation enzyme (e.g., Circligase™ enzyme, Taq DNA Ligase, HiFi Taq DNA Ligase, T4 ligase, PBCV-1 DNA Ligase (also known as SplintR® ligase) or Ampligase® DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, PBCV-1 DNA Ligase (also known as SplintR® ligase) or a Taq DNA Ligase. In embodiments, the ligase enzyme includes a T4 DNA ligase, T4 RNA ligase 1, T4 RNA ligase 2, T3 DNA ligase or T7 DNA ligase. In embodiments, the enzymatic ligation is performed by a mixture of ligases. In embodiments, the ligation enzyme is selected from the group consisting of T4 DNA ligase, T4 RNA ligase 1, T4 RNA ligase 2, RtcB ligase, T3 DNA ligase, T7 DNA ligase, Taq DNA ligase, PBCV-1 DNA Ligase, a thermostable DNA ligase (e.g., 5'AppDNA/RNA ligase), an ATP dependent DNA ligase, an RNA-dependent DNA ligase (e.g., SplintR® ligase), and combinations thereof. In embodiments, enzymatic ligation includes two different ligation enzymes (e.g., SplintR® ligation and T4 DNA ligase, or SplintR® ligase and Taq DNA ligase). In embodiments, enzymatic ligation includes more than two different ligation enzymes.

In embodiments, the probe oligonucleotide includes an amplification primer binding sequence, a sequencing primer binding sequence, or both an amplification primer binding sequence and a sequencing primer binding sequence. In embodiments, the probe oligonucleotide includes an amplification primer binding sequence. In embodiments, the probe oligonucleotide includes a sequencing primer binding sequence. In embodiments, the probe oligonucleotide includes both an amplification primer binding sequence and a sequencing primer binding sequence. In embodiments, the probe oligonucleotide includes at least two primer binding sequences. In embodiments, the probe oligonucleotide includes an amplification primer binding sequence. In embodiments, the probe oligonucleotide includes a sequencing primer binding sequence. The amplification primer binding sequence refers to a nucleotide sequence that is complementary to a primer useful in initiating amplification (i.e., an amplification primer). Likewise, a sequencing primer binding sequence is a nucleotide sequence that is complementary to a primer useful in initiating sequencing (i.e., a sequencing primer). Primer binding sequences usually have a length in the range of between 3 to 36 nucleotides, also 5 to 24 nucleotides, also from 14 to 36 nucleotides. In embodiments, an amplification primer and a sequencing primer are complementary to the same primer binding sequence, or overlapping primer binding sequences. In embodiments, an amplification primer and a sequencing primer are complementary to different primer binding sequences.

In embodiments, the probe oligonucleotide includes a primer binding sequence from a known set of primer binding sequences. In embodiments, the probe oligonucleotide includes at least two primer binding sequences from a known set of primer binding sequences. In embodiments, the probe oligonucleotide includes two or more primer binding sequences from a known set of primer binding sequences. In embodiments, the probe oligonucleotide includes up to 50 different primer binding sequences from a known set of primer binding sequences. In embodiments, the probe oligonucleotide includes up to 10 different primer binding sequences from a known set of primer binding sequences. In embodiments, the probe oligonucleotide includes up to 5 different primer binding sequences from a known set of primer binding sequences. In embodiments, the probe oligonucleotide includes two or more sequencing primer binding sequences from a known set of sequencing primer binding sequences. In embodiments, the probe oligonucleotide includes 1, 2, 3, 4, 5, 6, 7, 8, 9, or 10 primer binding sequences from a known set of primer binding sequences. In embodiments, the probe oligonucleotide includes two or more different primer binding sequences from a known set of primer binding sequences. In embodiments, the probe oligonucleotide includes 1, 2, 3, 4, 5, 6, 7, 8, 9, or 10 different primer binding sequences from a known set of primer binding sequences. In embodiments, the probe oligonucleotide includes 2 to 5 primer binding sequences from a known set of primer binding sequences. In embodiments, the probe oligonucleotide includes 2 to 5 different primer binding sequences from a known set of primer binding sequences. In embodiments, the probe oligonucleotide includes 2 to 5 sequencing primer binding sequences from a known set of sequencing primer binding sequences. In embodiments, the probe oligonucleotide includes 2 to 5 different sequencing primer binding sequences from a known set of sequencing primer binding sequences. In embodiments, the probe oligonucleotide includes at least two different primer binding sequences. In embodiments, the plurality of probe oligonucleotides includes at least two different primer binding sequences (e.g., a first probe oligonucleotide includes a first primer binding sequence and a second probe oligonucleotide includes a second primer binding sequence). In embodiments, the probe oligonucleotide includes two different sequencing primer binding sequences.

In embodiments, the known set of primer binding sequences includes at least 2 different primer binding sequences. In embodiments, the known set of primer binding sequences includes two or more different primer binding sequences. In embodiments, the known set of primer binding sequences includes at least 3 different primer binding sequences. In embodiments, the known set of primer binding sequences includes three or more different primer binding sequences. In embodiments, the known set of primer binding sequences includes at least 2 different sequencing primer binding sequences. In embodiments, the known set of primer binding sequences includes two or more different sequencing primer binding sequences. In embodiments, the known set of primer binding sequences includes 2 to 10 different sequencing primer binding sequences. In embodiments, the known set of primer binding sequences includes 2 to 6 different sequencing primer binding sequences. In embodiments, the known set of primer binding sequences includes 3 to 8 different sequencing primer binding sequences.

In embodiments, extending includes incubating the circular oligonucleotide with a strand-displacing polymerase for about 15 minutes to about 2 hours. In embodiments, extending includes incubating the circular oligonucleotide with a strand-displacing polymerase for about 30 minutes to about 60 minutes. In embodiments, extending includes incubating the circular oligonucleotide with a strand-displacing polymerase for about 15, 20, 25, 30, 35, 40, 45, 50, 55, or 60 minutes. In embodiments, extending includes incubating the circular oligonucleotide with a strand-displacing polymerase for about 15 minutes, 30 minutes, 45 minutes, 60 minutes, 90 minutes, 2 hours, 3 hours, or 4 hours. In embodiments, extending includes incubating the circular oligonucleotide with a strand-displacing polymerase for about 1, 2, 3, 4, 5, 6, 7, 8, 9, 10, 11, 12, or more hours. In embodiments, extending further includes incubating with a plurality of deoxyribonucleotides (dNTPs), optionally modified dNTPs.

In embodiments, amplifying the circular oligonucleotide includes incubating the circular oligonucleotide with the strand-displacing polymerase at a temperature of about 20° C. to about 50° C. In embodiments, incubation with the strand-displacing polymerase is at a temperature of about 20° C., about 25° C., about 30° C., about 35° C., about 40° C., about 45° C., or about 50° C. In embodiments, incubation with the strand-displacing polymerase is at a temperature of about 35° C. to 42° C. In embodiments, incubation with the strand-displacing polymerase is at a temperature of about 30° C. to 35° C. In embodiments, incubation with the strand-displacing polymerase is at a temperature of about 25° C. to 35° C. In embodiments, incubation with the strand-displacing polymerase is at a temperature of about 35° C., about 36° C., about 37° C., about 38° C., about 39° C., about 40° C., about 41° C., or about 42° C. In embodiments, the strand-displacing polymerase is a phi29 polymerase, a SD polymerase, a Bst large fragment polymerase, phi29 mutant polymerase, a *Thermus aquaticus* polymerase, or a thermostable phi29 mutant polymerase.

In embodiments, amplifying includes rolling circle amplification (RCA) or rolling circle transcription (RCT) (see, e.g., Lizardi et al., Nat. Genet. 19:225-232 (1998), which is incorporated herein by reference in its entirety). Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, amplifying includes exponential RCA (eRCA). A common type of eRCA is hyperbranched rolling circle amplification (see, e.g., Mohsen et al. Acc Chem Res. 2016 Nov. 15; 49(11): 2540-2550, which is incorporated herein by reference in its entirety). In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer. In embodiments, the polymerase is T4, T7, Sequenase™, Taq, Klenow, Pol I DNA polymerases, SD polymerase, Bst large fragment polymerase, or a phi29 polymerase or mutant thereof. In embodiments, the strand-displacing enzyme is an SD polymerase, Bst large fragment polymerase, or a phi29 polymerase or mutant thereof. In embodiments, the strand-displacing polymerase is Bst DNA Polymerase Large Fragment, *Thermus aquaticus* (Taq) polymerase, or a mutant thereof. In embodiments, the strand-displacing polymerase is a phi29 polymerase, a phi29 mutant polymerase or a thermostable phi29 mutant polymerase. A "phi polymerase" (or "Φ29 polymerase") is a DNA polymerase from the Φ29 phage or from one of the related phages that, like Φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase photo-tolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase including at least one mutation selected from the group consisting of M8R, V51A, M97T, L123S, G197D, K209E, E221K, E239G, Q497P, K512E, E515A, and F526 (relative to wild type phi29 polymerase). In embodiments, the polymerase is a phage or bacterial RNA polymerases (RNAPs). In embodiments, the polymerase is a T7 RNA polymerase. In embodiments, the polymerase is an RNA polymerase. Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

In embodiments, the amplification method includes a standard dNTP mixture including dATP, dCTP, dGTP and dTTP (for DNA) or dATP, dCTP, dGTP and dUTP (for RNA). In embodiments, the amplification method includes a mixture of standard dNTPs and modified nucleotides that contain functional moieties (e.g., bioconjugate reactive groups) that serve as attachment points to the cell or the matrix in which the cell is embedded (e.g. a hydrogel polymer matrix). In embodiments, the amplification method includes a mixture of standard dNTPs and modified nucleotides that contain functional moieties (e.g., bioconjugate reactive groups) that participate in the formation of a bioconjugate linker. The modified nucleotides may react and link the amplification product to the surrounding cell scaffold. For example, amplifying may include an extension reaction wherein the polymerase incorporates a modified nucleotide into the amplification product, wherein the modified nucleotide includes a bioconjugate reactive moiety (e.g., an alkynyl moiety) attached to the nucleobase. The bioconjugate reactive moiety of the modified nucleotide participates in the formation of a bioconjugate linker by reacting with a complementary bioconjugate reactive moiety present in the cell (e.g., a crosslinking agent, such as NHS-PEG-azide, or an amine moiety) thereby attaching the amplification product to the internal scaffold of the cell. In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (e.g., DCC or EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PEGylated bis(sulfosuccinimidyl)suberate) (BS(PEG)$_9$)). In embodiments, amplifying includes RCA or eRCA.

In embodiments, the method includes amplifying the circular oligonucleotide by extending an amplification primer with a polymerase (e.g., a strand-displacing polymerase), wherein the primer extension generates an extension product including multiple complements of the circular oligonucleotide, referred to as an amplicon. An amplicon typically contains multiple, tandem copies of the circularized nucleic acid molecule of the corresponding sample nucleic acid. The number of copies can be varied by appropriate modification of the reaction conditions, such as varying the number of amplification cycles, using polymerases of varying processivity in the amplification reaction, or varying the length of time that the amplification reaction is run. In embodiments, the circular polynucleotide is copied about 5-50 times (i.e., the extension product includes about 5 to 50 complements of the circular polynucleotide). In embodiments, the circular polynucleotide is copied about 100-300 times (i.e., the extension product includes about 100 to 300 complements of the circular polynucleotide).

In embodiments, the method includes subjecting (e.g., contacting) the cell to a polymer including a plurality of immobilized oligonucleotide primers (e.g., primers covalently attached to components within the matrix forming polymer). In embodiments, the method includes contacting the cell with a plurality of oligonucleotide primers that are capable of forming a covalent attachment to one or more cellular components; when the oligonucleotide primers form a covalent attachment to a cellular component, they may be referred to as immobilized oligonucleotide primers. In embodiments, the covalent attachment of the oligonucleotide primers to one or more cellular components does not require cross-linking. In embodiments, the attachment of the oligonucleotide primers to one or more cellular components includes hybridization of modified oligonucleotides (e.g., LNA-containing oligonucleotides that provide increased thermal hybridization stability). Non-limiting examples of covalent attachment include amine-modified polynucleotides within the primer reacting with epoxy or isothiocyanate groups within the matrix, succinylated polynucleotides within the primer reacting with aminophenyl or aminopropyl functional groups within the matrix, dibenzocyclooctyne-modified polynucleotides within the primer reacting with azide functional groups within the matrix (or vice versa), trans-cyclooctyne-modified polynucleotides within the primer reacting with tetrazine or methyl tetrazine groups within the matrix (or vice versa), disulfide modified polynucleotides within the primer reacting with mercapto-functional groups within the matrix, amine-functionalized polynucleotides within the primer reacting with carboxylic acid groups within the matrix or cellular component via 1-ethyl-3-(3-dimethylaminopropyl)-carbodiimide hydrochloride (EDC) chemistry, thiol-modified polynucleotides within the primer attaching to the matrix or cellular component via a disulfide bond or maleimide linkage, alkyne-modified polynucleotides within the primer attaching to a matrix via copper-catalyzed click reactions to azide functional groups within the matrix, azide-modified polynucleotides within the primer attaching to the matrix via copper-catalyzed click reactions to alkyne functional groups within the matrix, and acrydite-modified polynucleotides within the primer polymerizing with free acrylic acid monomers within the matrix to form polyacrylamide. In embodiments, the primer is attached to the matrix through electrostatic binding. For example, the negatively charged phosphate backbone of the primer may be bound electrostatically to positively charged monomers in the matrix.

In embodiments, the method includes contacting the cell with a plurality of specific binding reagents, wherein the specific binding reagent includes an oligonucleotide primer. In embodiments, the oligonucleotide primer may be used to aid in tethering the extension product to a confined area and may not be extended. In embodiments, the oligonucleotide primer includes a blocking group at the 3' end that prevents polymerase extension. In embodiments, the method includes extending the one or more oligonucleotide primers hybridized to an extension product with a polymerase. For example, the one or more oligonucleotide primers attached to the specific binding reagent (e.g., an antibody) may be used to aid in tethering the extension product to a localized area and may be extended in an exponential RCA amplification reaction. In embodiments, the 5' end of the primer is attached to the specific binding reagent. In embodiments, the specific binding reagent includes an antibody, single-chain Fv fragment (scFv), antibody fragment-antigen binding (Fab), or an aptamer. For example, the matrix or cellular component (e.g., a protein) may contain a complementary specific binding reagent to the primer containing a specific binding reagent.

In embodiments, the plurality of oligonucleotide primers form covalent attachments (i.e., bioconjugate linkers) to one or more cellular components through bioconjugate reactive moieties. In embodiments, the 5' end of the primer contains a functional group that is capable of reacting with a complementary group so the primer may be tethered to a cellular component (e.g., a protein). In embodiments, the primers may be used to aid in tethering the extension product to a confined area and may not be extended. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the method includes extending the one or more immobilized oligonucleotides hybridized to an extension product with a polymerase. For example, the one or more immobilized oligonucleotides may be used to aid in tethering the extension product to a localized area and may be extended in an exponential RCA amplification reaction. In embodiments, the 5' end of the primer is covalently attached to a cellular component. In embodiments, the 5' end of the primer is covalently attached to the matrix. In embodiments, the 3' end of the primer is covalently attached to a cellular component. In embodiments, the 3' end of the primer is covalently attached to the matrix. The primers can include one or more reactive moieties. As used herein, the term reactive moiety includes any group capable of reacting with another molecule, e.g., a nucleic acid or polypeptide through covalent, non-covalent or other interactions. By way of example, the primer can include an amino acid reactive moiety that reacts with an amino acid on a protein or polypeptide through a covalent, non-covalent or other interaction.

In embodiments, the amplification primer is attached to a solid surface. In embodiments, the amplification primer is attached to a cellular component. In embodiments, the amplification primer is in solution. In embodiments, the amplification primer includes one or more phosphorothioate nucleotides. In embodiments, the amplification primer includes a plurality of phosphorothioate nucleotides. In embodiments, about or at least about 20%, 30%, 40%, 50%, 60%, 70%, 80%, 90%, or about 100% of the nucleotides in the amplification primer are phosphorothioate nucleotides. In embodiments, most of the nucleotides in the amplification primer are phosphorothioate nucleotides. In embodiments, all of the nucleotides in the amplification primer are phosphorothioate nucleotides.

In embodiments, the blocking oligonucleotide is the amplification primer, and amplifying includes extending the probe hybridization sequence.

In embodiments, the amplification primer and the sequencing primer includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers (e.g., amplification primer or sequencing primer) include nucleotides ranging from 17 to 30 nucleotides. In embodiments, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

In embodiments, the target polynucleotide is the amplification primer. In embodiments, amplifying the circular oligonucleotide includes hybridizing a primer to the circular oligonucleotide and extending the primer with a strand-displacing polymerase. In embodiments, amplifying the circular oligonucleotide includes contacting the complex with an exonuclease enzyme and generating a 3' end, wherein the exonuclease enzyme removes a sequence of the target polynucleotide, and extending the 3' end with a strand-displacing polymerase.

In embodiments, the method further includes removing the target polynucleotide. In embodiments, removing the target polynucleotide includes contacting the target polynucleotide with a ribonuclease. In embodiments, the ribonuclease is RNAse H.

In embodiments, a padlock probe oligonucleotide binds to the target polynucleotide and is detected prior to contacting the target polynucleotide complex. In embodiments, the padlock probe oligonucleotide includes a barcode sequence. In embodiments, the padlock probe oligonucleotide and the amplification product are detected in the cell or tissue. In embodiments, the padlock probe oligonucleotide is detected in the cell or tissue and the amplification product is detected outside the cell or tissue (e.g., in a different device, such as the Singular Genomics G4™ Sequencing Platform). In embodiments, the padlock probe oligonucleotide is detected in the cell or tissue and the amplification product is detected in the cell or tissue (e.g., using the same device, such as the Singular Genomics G4X™ Platform).

Padlock probes are specialized ligation probes, examples of which are known in the art, see for example Nilsson M, et al. *Science*. 1994; 265(5181):2085-2088), and has been applied to detect transcribed RNA in cells, see for example Christian A T, et al. Proc Natl Acad Sci USA. 2001; 98(25):14238-14243, both of which are incorporated herein by reference in their entireties. In embodiments, the padlock probe is approximately 50 to 200 nucleotides. In embodiments, a padlock probe has a first domain that is capable of hybridizing to a first target sequence domain, and a second domain, capable of hybridizing to an adjacent second sequence domain. The configuration of the padlock probe is such that upon ligation of the first and second ligation domains of the padlock probe, the probe forms a circular polynucleotide, and forms a complex with the sequence (i.e., the sequence it hybridized to, the target sequence) wherein the target sequence is "inserted" into the loop of the circle. Padlock probes are useful for the methods provided herein and include, for example, padlock probes for genomic analyses, as exemplified by Gore, A. et al. Nature 471, 63-67 (2011); Porreca, G. J. et al. Nat Methods 4, 931-936 (2007); Li, J. B. et al. Genome Res 19, 1606-1615 (2009), Zhang, K. et al. Nat Methods 6, 613-618 (2009); Noggle, S. et al. Nature 478, 70-75 (2011); and Li, J. B. et al. Science 324, 1210-1213 (2009), the content of each of which is incorporated by reference in its entirety.

In embodiments, the circular oligonucleotide and/or the amplification product is detected. In embodiments, the circular oligonucleotide is detected. In embodiments, the amplification product is detected. In embodiments, detecting includes hybridizing a detection probe including a detectable label to the amplification product and detecting the detectable label. In embodiments, the circular oligonucleotide includes a binding sequence that is complementary to a fluorescent in situ hybridization (FISH) probe. FISH probes may be custom designed using known techniques in the art, see for example Gelali, E., Girelli, G., Matsumoto, M. et al. Nat Commun 10, 1636 (2019).

In embodiments, detecting includes detecting a light emission with a wavelength of 400-800 nm. In embodiments, detecting includes detecting a light emission with a wavelength of 443 nm, 506 nm, 512 nm, 514 nm, 517 nm, 518 nm, 519 nm, 520 nm, 521 nm, 523 nm, 526 nm, 527 nm, 533 nm, 537 nm, 540 nm, 548 nm, 550 nm, 554 nm, 555 nm, 556 nm, 565 nm, 568 nm, 572 nm, 573 nm, 574 nm, 575 nm, 578 nm, 580 nm, 590 nm, 591 nm, 595 nm, 596 nm, 603 nm, 605 nm, 615 nm, 617 nm, 618 nm, 619 nm, 630 nm, 647 nm, 650 nm, 665 nm, 670 nm, 690 nm, 694 nm, 702 nm, 723 nm, or 775 nm. In embodiments, detecting includes detecting a light emission in the near-infrared spectrum. In embodiments, detecting includes detecting a light emission with a wavelength from 600 nm-900 nm. In embodiments, detecting includes detecting a light emission with a wavelength from 600 nm-1450 nm. In embodiments, detecting includes detecting a light emission with a wavelength from 1000 nm-1700 nm. In embodiments, detecting includes detecting a light emission in the "imaging window," which refers to a range of wavelengths where tissue autofluorescence is minimal and the absorption and emission of light in tissue results in minimal light scattering (see, e.g., Pansare et al. Chem Mater. 2012 Mar. 13; 24(5): 812-827 and Wang et al. ACS Cent Sci. 2020 Aug. 26; 6(8): 1302-1316).

In embodiments, detecting includes sequencing. In embodiments, detecting the amplification product includes hybridizing an oligonucleotide associated with a detectable label to the amplification product and identifying the detectable label. In embodiments, detecting includes two-dimensional (2D) or three-dimensional (3D) fluorescent microscopy. Suitable imaging technologies are known in the art, as exemplified by Larsson et al., Nat. Methods (2010) 7:395-397 and associated supplemental materials, the entire content of which is incorporated by reference herein in its entirety. In embodiments of the methods provided herein, the imaging is accomplished by confocal microscopy. Confocal fluorescence microscopy involves scanning a focused laser beam across the sample, and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed to reconstruct the final image. See York, Andrew G., et al. "Instant super-resolution imaging in live cells and embryos via analog image processing." *Nature methods* 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, or multi-photon microscopy. Implementations of oblique plane microscopy are known, for example in Sapznik et al. eLife 2020; 9:e57681. Implementations of oblique plane microscopy are known, for example as described in Heintzmann and Huser, Chem. Rev. 2017, 117, 23, 13890-13908.

In embodiments, sequencing includes encoding the sequencing read into a codeword. Useful encoding schemes include those developed for telecommunications, coding theory and information theory such as those set forth in Hamming, *Coding and Information Theory*, $2^{nd}$ Ed. Prentice Hall, Englewood Cliffs, N.J. (1986) and Moon T K. Error Correction Coding: Mathematical Methods and Algorithms. ed. 1st Wiley: 2005., each of which are incorporated herein by reference. A useful encoding scheme uses a Hamming code. A Hamming code can provide for signal (and therefore sequencing and barcode) distinction. In this scheme, signal states detected from a series of nucleotide incorporation and detection events (i.e., while sequencing the oligonucleotide barcode) can be represented as a series of the digits to form a codeword, the codeword having a length equivalent to the number incorporation/detection events. The digits can be binary (e.g. having a value of 1 for presence of signal and a value of 0 for absence of the signal) or digits can have a higher radix (e.g., a ternary digit having a value of 1 for fluorescence at a first wavelength, a value of 2 for fluorescence at a second wavelength, and a value of 0 for no fluorescence at those wavelengths, etc.). Sequence discrimination capabilities are provided when codewords can be quantified via Hamming distances between two codewords (i.e., barcode 1 having codeword 1, and barcode 2 having codeword 2, etc.)

In embodiments, the method further includes sequencing the amplification product. In embodiments, sequencing includes sequencing by synthesis, sequencing by binding, sequencing by ligation, or pyrosequencing. In embodiments, sequencing includes extending a sequencing primer by incorporating a labeled nucleotide or labeled nucleotide analogue, and detecting the label to generate a signal for each incorporated nucleotide or nucleotide analogue, wherein the sequencing primer is hybridized to the extension product. In embodiments, the sequencing primer includes a sequence of the subject sequence.

In embodiments, the method includes sequencing the amplification products. A variety of sequencing methodologies can be used such as sequencing-by synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. *Science* 281(5375), 363 (1998); U.S. Pat. Nos. 6,210, 891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. In embodiments, sequencing includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product produced by the amplification methods described herein). In embodiments, sequencing may be accomplished by a sequencing-by-synthesis (SBS) process. In embodiments, sequencing includes a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. By ordering the products derived using these modified nucleotides it is possible to deduce the DNA sequence of the oligonucleotide target nucleic acid sequence.

In embodiments, the methods of sequencing a nucleic acid include a extending a polynucleotide by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol µ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Terminator™ γ, 9° N polymerase (exo-), Terminator™ II, Terminator™ III, or Terminator™ IX). In embodiments, the DNA polymerase is a thermophilic nucleic acid polymerase. In embodiments, the DNA polymerase is a modified archaeal DNA polymerase. In embodiments, the polymerase is a mutant $P.$ $abyssi$ polymerase (e.g., such as a mutant $P.$ $abyssi$ polymerase described in WO 2018/148723 or WO 2020/056044, each of which is incorporated herein by reference for all purposes). In embodiments, the polymerase is a bacterial DNA polymerase, eukaryotic DNA polymerase, archaeal DNA polymerase, viral DNA polymerase, or phage DNA polymerases. Bacterial DNA polymerases include $E.$ $coli$ DNA polymerases I, II and III, IV and V, the Klenow fragment of $E.$ $coli$ DNA polymerase, $Clostridium$ $stercorarium$ (Cst) DNA polymerase, $Clostridium$ $thermocellum$ (Cth) DNA polymerase and $Sulfolobus$ $solfataricus$ (Sso) DNA polymerase. Eukaryotic DNA polymerases include DNA polymerases α, β, γ, δ, ε, η, ζ, λ, σ, µ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as $Thermus$ $aquaticus$ (Taq) DNA polymerase, $Thermus$ $filiformis$ (Tfi) DNA polymerase, $Thermococcus$ $zilligi$ (Tzi) DNA polymerase, $Thermus$ $thermophilus$ (Tth) DNA polymerase, $Thermus$ $flavusu$ (Tfl) DNA polymerase, $Pyrococcus$ $woesei$ (Pwo) DNA polymerase, $Pyrococcus$ $furiosus$ (Pfu) DNA polymerase and Turbo Pfu DNA polymerase, $Thermococcus$ $litoralis$ (Tli) DNA polymerase, $Pyrococcus$ sp. GB-D polymerase, $Thermotoga$ $maritima$ (Tma) DNA polymerase, $Bacillus$ $stearothermophilus$ (Bst) DNA polymerase, $Pyrococcus$ $Kodakaraensis$ (KOD) DNA polymerase, Pfx DNA polymerase, $Thermococcus$ sp. JDF-3 (JDF-3) DNA polymerase, $Thermococcus$ $gorgonarius$ (Tgo) DNA polymerase, $Thermococcus$ $acidophilium$ DNA polymerase; $Sulfolobus$ $acidocaldarius$ DNA polymerase; $Thermococcus$ sp. go N-7 DNA polymerase; $Pyrodictium$ $occultum$ DNA polymerase; $Methanococcus$ $voltae$ DNA polymerase; $Methanococcus$ $thermoautotrophicum$ DNA polymerase; $Methanococcus$ $jannaschii$ DNA polymerase; $Desulfurococcus$ strain TOK DNA polymerase (D. Tok Pol); $Pyrococcus$ $abyssi$ DNA polymerase; $Pyrococcus$ $horikoshii$ DNA polymerase; $Pyrococcus$ $islandicum$ DNA polymerase; $Thermococcus$ $fumicolans$ DNA polymerase; $Aeropyrum$ $pernix$ DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase.

In embodiments, sequencing includes a plurality of sequencing cycles. In embodiments, sequencing includes 20 to 100 sequencing cycles. In embodiments, sequencing includes 50 to 100 sequencing cycles. In embodiments, sequencing includes 50 to 300 sequencing cycles. In embodiments, sequencing includes 50 to 150 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a)

extending a sequencing primer by incorporating a labeled nucleotide, or labeled nucleotide analogue and (b) detecting the label to generate a signal for each incorporated nucleotide or nucleotide analogue.

In embodiments, sequencing includes sequentially extending a plurality of sequencing primers (e.g., sequencing a first region of a target nucleic acid followed by sequencing a second region of a target nucleic acid, followed by sequencing N regions, where N is the number of sequencing primers in the known sequencing primer set). In embodiments, sequencing includes generating a plurality of sequencing reads. In embodiments, sequencing includes sequentially sequencing a plurality of different targets by initiating sequencing with different sequencing primers. For example, a first circularizable probe includes a first primer binding site (a nucleic acid sequence complementary to a first sequencing primer) and optionally a first barcode sequence or barcode nucleotide. In a similar manner, a second and third padlock probe include a second primer binding site (a nucleic acid sequence complementary to a second, different, sequencing primer) and a third primer binding site (a nucleic acid sequence complementary to a third, different from both Primer 1 and Primer 2, sequencing primer), respectively. During the first round of sequencing (following probe circularization and amplification according to the methods described herein), using primer 1, the probe hybridized to the first nucleic acid molecule is detected. In the second round of sequencing, primer 2 can hybridize and sequence an identifying sequence of the probe (e.g., a barcode sequence or nucleotide) hybridized to a second nucleic acid molecule. Similarly, in the third round of sequencing, primer 3 can hybridize and sequence the probe hybridized to the third nucleic acid molecule.

In embodiments, sequencing includes sequencing by synthesis, sequencing by binding, sequencing by ligation, or pyrosequencing. In embodiments, sequencing includes hybridizing a sequencing primer to the amplification product, (a) extending the sequencing primer by incorporating a labeled nucleotide or labeled nucleotide analogue and (b) detecting the label for each incorporated nucleotide or nucleotide analogue. In embodiments, the method further includes measuring an amount of one or more of the targets by counting the one or more associated barcodes. In embodiments, the method further includes counting the one or more associated barcodes in an optically resolved volume.

In embodiments, sequencing includes extending a sequencing primer to generate a sequencing read. In embodiments, sequencing includes extending a sequencing primer by incorporating a labeled nucleotide, or labeled nucleotide analogue and detecting the label to generate a signal for each incorporated nucleotide or nucleotide analogue. In embodiments, the labeled nucleotide or labeled nucleotide analogue further includes a reversible terminator moiety. In embodiments, the labeled nucleotide or labeled nucleotide analogue further includes a reversible terminator moiety. In embodiments, the reversible terminator moiety is attached to the 3' oxygen of the nucleotide and is independently

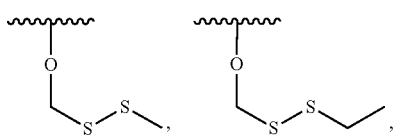

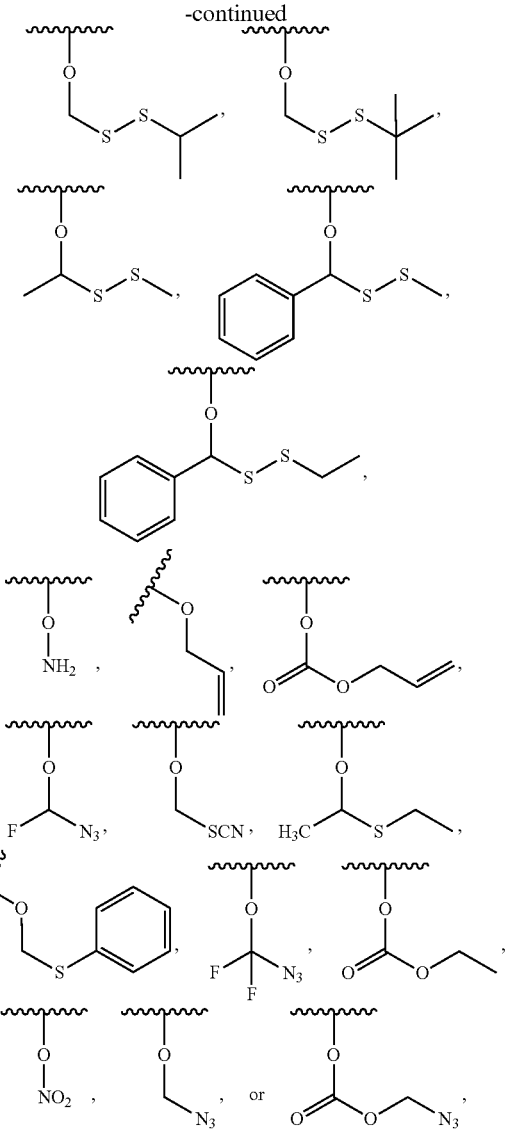

wherein the 3' oxygen is explicitly depicted in the above formulae. Additional examples of reversible terminators may be found in U.S. Pat. No. 6,664,079, Ju J. et al. (2006) *Proc Natl Acad Sci USA* 103(52):19635-19640.; Ruparel H. et al. (2005) *Proc Natl Acad Sci USA* 102(17):5932-5937.; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol moiety.

In embodiments, the method includes sequencing a plurality of target polynucleotides of a cell in situ within an optically resolved volume. In embodiments, the number of unique targets detected within an optically resolved volume of a sample is about 3, 10, 30, 50, or 100. In embodiments, the number of unique targets detected within an optically resolved volume of a sample is about 1 to 10. In embodiments, the number of unique targets detected within an optically resolved volume of a sample is about 5 to 10. In embodiments, the number of unique targets detected within an optically resolved volume of a sample is about 1 to 5. In embodiments, the number of unique targets detected within an optically resolved volume of a sample is at least 3, 10, 30, 50, or 100. In embodiments, the number of unique targets detected within an optically resolved volume of a sample is less than 3, 10, 30, 50, or 100. In embodiments, the number of unique targets detected within an optically resolved volume of a sample is about 1, 2, 3, 4, 5, 6, 7, 8, 9, 10, 20, 50, 100, 500, 1,000, 5,000, 10,000, or 200,000. In embodiments, the methods allow for detection of a single target of interest. In embodiments, the methods allow for multiplex detection of a plurality of targets of interest (i.e., generating a multiplexed signal).

In embodiments, demultiplexing the multiplexed signal includes a linear decomposition of the multiplexed signal. Any of a variety of techniques may be employed for decomposition of the multiplexed signal. Examples include, but are not limited to, Zimmerman et al. Chapter 5: Clearing Up the Signal: Spectral Imaging and Linear Unmixing in Fluorescence Microscopy; Confocal Microscopy: Methods and Protocols, Methods in Molecular Biology, vol. 1075 (2014); Shirawaka H. et al.; Biophysical Journal Volume 86, Issue 3, March 2004, Pages 1739-1752; and S. Schlachter, et al, Opt. Express 17, 22747-22760 (2009); the content of each of which is incorporated herein by reference in its entirety. In embodiments, multiplexed signal includes overlap of a first signal and a second signal and is computationally resolved, for example, by imaging software.

In embodiments, the optically resolved volume has an axial resolution (i.e., depth, or z) that is greater than the lateral resolution (i.e., xy plane). In embodiments, the optically resolved volume has an axial resolution that is greater than twice the lateral resolution. In embodiments, the dimensions (i.e., the x, y, and z dimensions) of the optically resolved volume are about 0.5 μm×0.5 μm×0.5 μm; 1 μm×1 μm×1 μm; 2 μm×2 μm×2 μm; 0.5 μm×0.5 μm×1 μm; 0.5 μm×0.5 μm×2 μm; 2 μm×2 μm×1 μm; or 1 μm×1 μm×2 μm. In embodiments, the dimensions (i.e., the x, y, and z dimensions) of the optically resolved volume are about 1 μm×1 μm×2 μm; 1 μm×1 μm×3 μm; 1 μm×1 μm×4 μm; or about 1 μm×1 μm×5 μm. See FIG. 5, for example. In embodiments, the dimensions (i.e., the x, y, and z dimensions) of the optically resolved volume are about 1 μm×1 μm×5 μm. In embodiments, the dimensions (i.e., the x, y, and z dimensions) of the optically resolved volume are about 1 μm×1 μm×6 μm. In embodiments, the dimensions (i.e., the x, y, and z dimensions) of the optically resolved volume are about 1 μm×1 μm×7 μm. In embodiments, the optically resolved volume is a cubic micron. In embodiments, the optically resolved volume has a lateral resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 1 to 2 μm, from 2 to 3 μm, from 3 to 4 μm, from 4 to 5 μm, from 5 to 6 μm, or from 6 to 10 μm.

In embodiments, the method further includes an additional imaging modality, immunofluorescence (IF), or immunohistochemistry modality (e.g., immunostaining). In embodiments, the method includes ER staining (e.g., contacting the cell with a cell-permeable dye which localizes to the endoplasmic reticula), Golgi staining (e.g., contacting the cell with a cell-permeable dye which localizes to the Golgi), F-actin staining (e.g., contacting the cell with a phalloidin-conjugated dye that binds to actin filaments), lysosomal staining (e.g., contacting the cell with a cell-permeable dye that accumulates in the lysosome via the lysosome pH gradient), mitochondrial staining (e.g., contacting the cell with a cell-permeable dye which localizes to the mitochondria), nucleolar staining, or plasma membrane staining. For example, the method includes live cell imaging (e.g., obtaining images of the cell) prior to or during fixing, immobilizing, and permeabilizing the cell. Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). *Methods in molecular biology* (Clifton, N.J.), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology (e.g., the cell boundary or cell shape) using known methods in the art. For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)).

In embodiments, the methods and compositions described herein are utilized to analyze the various sequences of TCRs and BCRs from immune cells, for example various clonotypes. In embodiments, the target nucleic acid includes a nucleic acid sequence encoding a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In embodiments, the target nucleic acid includes a nucleic acid sequence encoding a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof). In embodiments, the target nucleic acid includes a CDR3 nucleic acid sequence. In embodiments, the target nucleic acid includes a TCRA gene sequence or a TCRB gene sequence. In embodiments, the target nucleic acid includes a TCRA gene sequence and a TCRB gene sequence. In embodiments, the target nucleic acid includes sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), or T cell receptor delta constant genes (TRDC genes).

In embodiments, the target nucleic acid molecule includes a gene sequence, or a fragment thereof. In embodiments, a portion of the entire gene sequence is targeted with one or more of the probes described herein. In embodiments, the target nucleic acid molecule includes a sequence capable of encoding a protein (e.g., a protein imbued with biological function after transcribing and/or translating the nucleic acid sequence).

In embodiments, the target nucleic acid molecule includes an ALCAM, B3GAT1, BACH2, BCL11B, CCL5, CCR5, CCR7, CD14, CD160, CD163, CD19, CD2, CD226, CD24, CD27, CD274, CD276, CD28, CD33, CD34, CD38, CD3D, CD3E, CD4, CD40, CD40LG, CD44, CD52, CD6, CD69, CD74, CD8A, CD8B, CDCP1, CIITA, CR2, CTLA4, CX3CR1, CXCL8, CXCL9, CXCL13, CXCR6, DERL3, ENG, ENTPD1, EOMES, FAS, FASLG, FCER1G, FCGR3A, FCN1, FOXP3, GBP5, GNLY, GPR171, GYPA, GZMA, GZMB, GZMH, GZMK, GZMM, H1-10, HAVCR2, HLA-A, HLA-B, HLA-C, HLA-DPA1, HLA-DPB1, HLA-DRA, HLA-DRB1, HLA-DRB5, HLA-E, HLA-F, HOPX, ICOS, IFNG, IFNGR1, IGHD, IGHM, IL2RA, IL2RB, IL4R, IL7R, IRF1, ITGAE, ITGAL, ITGAM, ITGAX, ITGB1, ITK, JCHAIN, KIR2DL1, KIR2DL4, KIR3DL1, KIR3DL2, KIT, KLRB1, KLRC1, KLRC2, KLRC3, KLRD1, KLRG1, LAG3, LAMP1, LEF1, LTB, LYZ, MKI67, MME, MPL, MPO, MS4A1, MT1E, MT1F, MT1X, MT2A, NCAM1, NECTIN2, NECTIN4, NKG7, NT5E, PAX5, PDCD1, PECAMI, PLPP5, PRF1, PSMB10, PTPRC, PVR, PYHIN1, S100A12, S100A8, S100A9, SELL, STAT1, TBX21, TCF7, TCL1A, THY1, TIGIT, TNF, TNFRSF4, TNFRSF9, TOX, TRAT1, TRBC1, TRGV9, TRH, VCAN, XBP1, XCL1, XCL2, ZNF683, or EPCAM gene.

In embodiments, the target polynucleotide includes a fusion gene sequence. In embodiments, the gene fusion results from a structural rearrangement of a chromosome including the target polynucleotide. In embodiments, the fusion gene sequence results from an intrachromosomal gene fusion. In embodiments, the fusion gene sequence results from an interchromosomal gene fusion. In embodiments, the fusion gene sequence results from an insertion of a gene region from another chromosome. In embodiments, the fusion gene sequence results from a deletion of a gene region in a chromosome. In embodiments, the fusion gene sequence results from an inversion of a gene region with another chromosome. In embodiments, the fusion gene sequence results from a duplication (also referred to as a "tandem duplication") of a gene region from another chromosome. In embodiments, the gene fusion results from non-structural rearrangement mechanisms. In embodiments, the gene fusion results from transcription read-through of the target polynucleotide and an adjacent gene, wherein transcription read-through results in a fusion of the mRNA transcripts of the target polynucleotide and the adjacent gene. See, e.g., Latysheva et al. Nucleic Acids Res. 2016 Jun. 2; 44(10): 4487-4503 and Kumar-Sinha et al. Genome Med 7, 129 (2015), each of which are incorporated herein by reference in their entirety.

In embodiments, the fusion gene sequence includes a fusion of a rearranged B cell antigen receptor or fragment thereof, an IGHV gene or fragment thereof, an IGHD gene or fragment thereof, or an IGHJ gene or fragment thereof, IGHJC gene or fragment thereof, an IGKV gene or fragment thereof, an IGKJ gene or fragment thereof, an IGKC gene or fragment thereof, an IGLV gene or portion thereof, an IGLJ gene or portion thereof, an IGLC gene or fragment thereof, an IGK kappa deletion element or portion thereof, a IGK intronic enhancer element or portion thereof. In embodiments, the polynucleotide fusion includes a fusion of an ALK gene or portion thereof, a BRAF gene or portion thereof, an EGFR gene or portion thereof, an ERBB2 gene or portion thereof, a KRAS gene or portion thereof, a MET gene or portion thereof, an NRG1 gene or portion thereof, an FGFR1 gene or portion thereof, an FGFR2 gene or portion thereof, an FGFR3 gene or portion thereof, an NTRK1 gene or portion thereof, an NTRK2 gene or portion thereof, an NTRK3 gene or portion thereof, a RET gene or portion thereof, or a ROS1 gene or portion thereof.

In embodiments, the fusion gene sequence includes a RBPSM-MET, BCAN-NTRK1, TRIM22-BRAF, KIAA1549-BRAF, FGFR1-TACC1, EWSR1-FLI1, PAX3-FOXO1, ZFTA-RELA, COL3A1-PLAG1, FGFR3-TACC3, or NPM1-ALK fusion gene sequence.

In embodiments, the target polynucleotide can include any polynucleotide of interest. The polynucleotide can include DNA, RNA, peptide nucleic acid, morpholino nucleic acid, locked nucleic acid, glycol nucleic acid, threose nucleic acid, mixtures thereof, and hybrids thereof. In embodiments, the polynucleotide is obtained from one or more source organisms. In some embodiments, the polynucleotide can include a selected sequence or a portion of a larger sequence. In embodiments, sequencing a portion of a polynucleotide or a fragment thereof can be used to identify the source of the polynucleotide. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides, at least 100 consecutive nucleotides, or at least 150 consecutive nucleotides.

In embodiments, the entire sequence of the target polynucleotide is about 1 to 3 kb, and only a portion of that target (e.g., 50 to 100 nucleotides) is sequenced. In embodiments, the target polynucleotide is about 1 to 3 kb. In embodiments, the target polynucleotide is about 1 to 2 kb. In embodiments, the target polynucleotide is about 1 kb. In embodiments, the target polynucleotide is about 2 kb. In embodiments, the target polynucleotide is less than 1 kb. In embodiments, the target polynucleotide is about 500 nucleotides. In embodiments, the target polynucleotide is about 200 nucleotides. In embodiments, the target polynucleotide is about 100 nucleotides. In embodiments, the target polynucleotide is less than 100 nucleotides. In embodiments, the target polynucleotide is about 5 to 50 nucleotides.

In embodiments, the circular oligonucleotide is about 100 to about 1000 nucleotides in length. In embodiments, the circular oligonucleotide is about 100, about 200, about 300, about 400, about 500, about 600, about 700, about 800, about 900, or about 1000 nucleotides in length. In embodiments, the circular oligonucleotide is greater than 1000 nucleotides in length. In embodiments, the circular oligonucleotide is about or more than about 100, 150, 200, 250, 300, 350, 400, 500, 750, 1000, or more nucleotides in length. In embodiments, the circular oligonucleotide includes a plurality of sequencing primer binding sequences. In embodiments, the circular oligonucleotide includes a plurality of different sequencing primer binding sequences.

In embodiments, the target polynucleotide is an RNA nucleic acid sequence or DNA nucleic acid sequence. In embodiments, the target polynucleotide is an RNA nucleic acid sequence or DNA nucleic acid sequence from the same cell. In embodiments, the target polynucleotide is an RNA nucleic acid sequence. In embodiments, the RNA nucleic acid sequence is stabilized using known techniques in the art. For example, RNA degradation by RNase should be minimized using commercially available solutions, e.g., RNA Later®, RNA Lysis Buffer, or Keratinocyte serum-free medium). In embodiments, the target polynucleotide is messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target polynucleotide is pre-mRNA. In embodiments, the target polynucleotide is heterogeneous nuclear RNA (hnRNA). In embodiments, the target polynucleotide is mRNA, tRNA (transfer RNA), rRNA (ribosomal RNA), or noncoding RNA (such as lncRNA (long noncoding RNA)). In embodiments, the target polynucleotides are on different regions of the same RNA nucleic acid sequence. RNA, including mRNA, is highly susceptible to degradation upon exposure to one or more RNAses. RNAses are present in a wide range of locations, including water, many reagents, laboratory equipment and surfaces, skin, and mucous membranes. Working with RNA often requires preparing an RNAse-free environment and materials, as well as taking precautions to avoid introducing RNAses into an RNAse-free environment. These precautions include, but are not limited to, cleaning surfaces with an RNAse cleaning product (e.g., RNASEZAP™ and other commercially available products or 0.5% sodium dodecyl sulfate (SDS) followed by 3% $H_2O_2$); using a designated workspace, materials, and equipment (e.g., pipets, pipet tips); using barrier tips; baking designated glassware (e.g., 300° C. for 2 hours) prior to use; treating enzymes, reagents, and other solutions (e.g., with diethyl pyrocarbonate (DEPC) or dimethyl pyrocarbonate (DMPC)) or using commercially available, certified RNAse-free water or solutions, or ultrafiltered water (e.g., for Tris-based solutions); including an RNAse inhibitor while avoiding temperatures or denaturing conditions that could deactivate the inhibitor); and wearing clean gloves (while avoiding contaminated surfaces) and a clean lab coat.

In embodiments, the target polynucleotide includes RNA nucleic acid sequences. In embodiments the target polynucleotide is an RNA transcript. In embodiments the target polynucleotide is a single stranded RNA nucleic acid sequence. In embodiments, the target polynucleotide is an RNA nucleic acid sequence or a DNA nucleic acid sequence (e.g., cDNA). In embodiments, the target polynucleotide is a cDNA target polynucleotide nucleic acid sequence and before step a), the RNA nucleic acid sequence is reverse transcribed to generate the cDNA target polynucleotide nucleic acid sequence. In embodiments, reverse transcription of the RNA nucleic acid is performed with a reverse transcriptase, for example, Tth DNA polymerase or mutants thereof. In embodiments, the target polynucleotide is genomic DNA (gDNA), mitochondrial DNA, chloroplast DNA, episomal DNA, viral DNA, or copy DNA (cDNA). In embodiments, the target polynucleotide is coding RNA such as messenger RNA (mRNA), and non-coding RNA (ncRNA) such as transfer RNA (tRNA), microRNA (miRNA), small nuclear RNA (snRNA), or ribosomal RNA (rRNA). In embodiments, the target polynucleotide is a cancer-associated gene. In embodiments, to minimize amplification errors or bias, the target polynucleotide is not reverse transcribed to generate cDNA, i.e., the probe oligonucleotide is hybridized directly to the target nucleic acid. In embodiments, the target polynucleotide includes RNA or cDNA.

In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase. In embodiments, the polymerase is a *Thermus thermophilus* (Tth) DNA polymerase or mutant thereof. In embodiments, the polymerase is a Reverse Transcription Xenopolymerase (RTX). In embodiments, the polymerase is a mutant M-MLV reverse transcriptase from the Moloney murine leukemia virus.

In embodiments, the target nucleic acid (i.e., the target polynucleotide) includes a nucleic acid sequence encoding a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In embodiments, the target nucleic acid includes a nucleic acid sequence encoding a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof). In embodiments, the target nucleic acid includes a CDR3 nucleic acid sequence. In embodiments, the target nucleic acid includes a TCRA gene sequence or a TCRB gene sequence. In embodiments, the target nucleic acid includes a TCRA gene sequence and a TCRB gene sequence. In embodiments, the target nucleic acid includes sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), or T cell receptor delta constant genes (TRDC genes).

In embodiments, the target polynucleotide includes a cancer-associated gene nucleic acid sequence, a viral nucleic acid sequence, a bacterial nucleic acid sequence, or a fungal nucleic acid sequence. In embodiments, the cancer-associated gene is a nucleic acid sequence identified within The Cancer Genome Atlas Program.

In embodiments, the cancer-associated biomarker is MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene. In embodiments, the cell is a cell (e.g., a T cell) within a tumor. In embodiments, the cell is a non-allogenic cell (i.e., native cell to the subject) within a tumor. In embodiments, the cell is a tumor infiltrating lymphocyte (TIL). In embodiments, the cell is an allogenic cell. In embodiments, the cell is a circulating tumor cell.

In embodiments, the target polynucleotide includes a CD4, CD68, CD20, CD11c, CD8, HLA-DR, Ki67, CD45RO, PanCK, CD3e, CD44, CD45, HLA-A, CD14, CD56, CD57, CD19, CD2, CD1a, CD107a, CD21, Pax5, FOXP3, Granzyme B, CD38, CD39, CD79a, TIGIT, TOX, TP63, S100A4, TFAM, GP100, LaminBi, CK19, CK17, GATA3, SOX2, Bcl2, EpCAM, Caveolin, CD163, CD11b, MPO, CD141, iNOS, PD-1, PD-L1, ICOS, TIM3, LAG3, IDO1, CD40, HLA-E, IFNG, CD69, E-cadherin, CD31, Histone H3, Beta-actin, Podoplanin, SMA, Vimentin, Collagen IV, CD34, Beta-catenin, MMP-9, ZEB1, ASCT2, Na/K ATPase, HK1, LDHA, G6PD, IDH2, GLUT1, pNRF2, ATPA5, SDHA, Citrate Synthase, CPT1A, PARP, BAK, BCL-XL, BAX, BAD, Cytochrome c, LC3B, Beclin-1, H2AX, pRPS6, PCNA, Cyclin D1, HLA-DPB1, LEF1, GAL9, CD138, MC Tryptase, OX40, ZAP70, CD7, CiQa, CCR6, CD15, AXL, and/or CD227 nucleic acid sequence.

In embodiments, the target polynucleotide includes an IGH locus or a BCL-1, BCL-2, BCL-3, or BCL6 locus. In embodiments, the target polynucleotide includes a sequence encoding for a complementarity-determining region (CDR) of a T cell receptor or a B cell receptor. In embodiments, the target polynucleotide includes a sequence encoding for the CDR3 region of a T cell receptor or a B cell receptor. In embodiments, the target polynucleotide includes a sequence encoding for a V region or a complement thereof and a J region or a complement thereof.

In embodiments, the cell in situ is obtained from a subject (e.g., human or animal tissue). Once obtained, the cell is placed in an artificial environment in plastic or glass containers supported with specialized medium containing essential nutrients and growth factors to support proliferation. In embodiments, the cell is permeabilized and immobilized to a solid support surface. In embodiments, the cell is permeabilized and immobilized to an array (i.e., to discrete locations arranged in an array). In embodiments, the cell is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 µm. In embodiments, a plurality of cells are each immobilized on a patterned surface that have a mean or median separation from one another of about 10-20; 10-50; or 100 µm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the solid support includes a glass substrate. In embodiments, the glass substrate is a borosilicate glass substrate with a composition including $SiO_2$, $Al_2O_3$, $B_2O_3$, $Li_2O$, $Na_2O$, $K_2O$, MgO, CaO, SrO, BaO, ZnO, $TiO_2$, $ZrO_2$, $P_2O_5$, or a combination thereof (see e.g., U.S. Pat. No. 10,974,990). In embodiments, the glass substrate is an alkaline earth boro-aluminosilicate glass substrate. In embodiments, the solid support includes a channel bored into the solid support. In embodiments, the solid support includes a plurality of channels bored into the solid support. In embodiments, the solid support includes 2 channels bored into the solid support. In embodiments, the solid support includes 3 channels bored into the solid support. In embodiments, the solid support includes 4 channels bored into the solid support. In embodiments, the width of the channel is about 1 to 5 mm. In embodiments, the width of the channel is about 5 to 10 mm. In embodiments, the width of the channel is about 10 to 15 mm. In embodiments, the width of the channel is about 5 mm. In embodiments, the width of the channel is about 11 mm.

In embodiments, the solid support includes a polymer layer. In embodiments, the polymer layer includes polymerized units of alkoxysilyl methacrylate, alkoxysilyl acrylate, alkoxysilyl methylacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methylacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

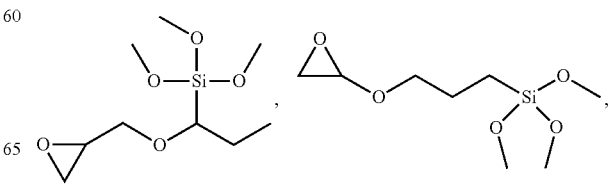

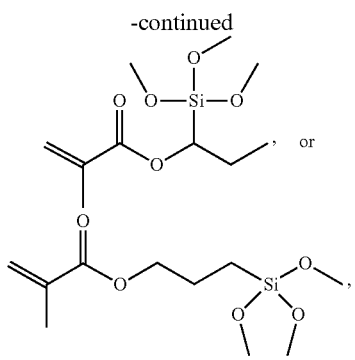

or a copolymer thereof. In embodiments, the polymer layer is an organically-modified ceramic polymer. In embodiments, the polymer includes polymerized monomers of alkoxysilyl polymers, such as

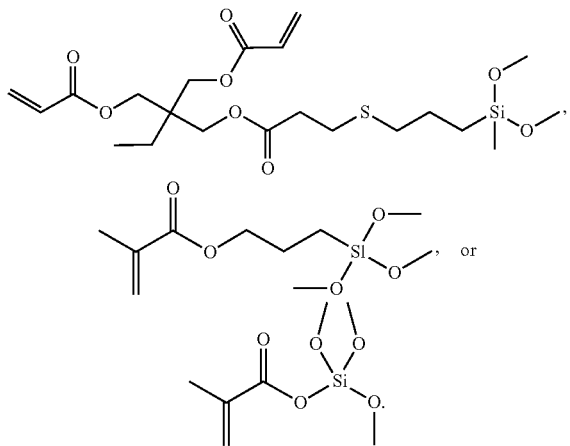

In embodiments, the solid support includes polymerized units of

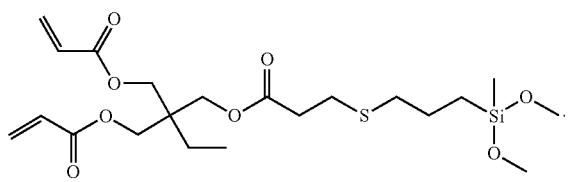 [SMILES: C=CC(=O)OCC(CC)(COC(=O)C=C)COC(=O)CCSCCC[Si](C)(OC)OC]

In embodiments, the solid support includes polymerized units of

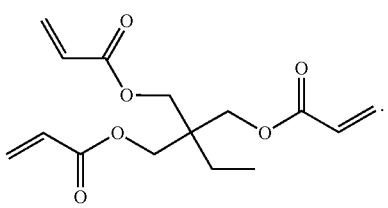 [SMILES: C=CC(=O)OCC(CC)(COC(=O)C=C)COC(=O)C=C]

In embodiments, the solid support includes polymerized units of

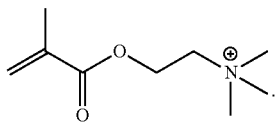

In embodiments, the polymer layer includes one or more ceramic particles, (e.g., silicates, aluminates, and titanates). In embodiments, the polymer layer includes titanium dioxide, zinc oxide, and/or iron oxide.

In embodiments, the cell is attached to the substrate via a bioconjugate reactive linker. In embodiments, the cell is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells. For example, a substrate containing a plurality of bioconjugate reactive moieties or a plurality of specific binding reagents, optionally in an ordered pattern, contacts a plurality of cells. Only cells containing complementary bioconjugate reactive moieties or complementary specific binding reagents are capable of reacting, and thus adhering, to the substrate.

In embodiments, the methods are performed in situ on isolated cells or in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or proteins and lipids.

In embodiments, the cell is permeabilized. In embodiments, the methods are performed in situ on isolated cells or in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or proteins and lipids. In embodiments, the method includes digesting the cell by contacting the cell with an endopeptidase.

In embodiments, the cell is immobilized to a substrate. The cell may have been cultured on the surface, or the cell may have been initially cultured in suspension and then fixed to the surface. Substrates can be two- or three-dimensional and can include a planar surface (e.g., a glass slide). A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites. In embodiments, the substrate includes a polymeric coating, optionally containing bioconjugate reactive moieties capable of affixing the sample. Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a sample. In embodiments, the substrate is not a flow cell. In embodiments, the substrate is a flow cell. In embodiments, the substrate includes a polymer matrix material (e.g., polyacrylamide, cellulose, alginate, polyamide, cross-linked agarose, cross-linked dextran or cross-linked polyethylene glycol), which may be referred to herein as a "matrix", "synthetic matrix", "exogenous polymer" or "exogenous hydrogel". In embodiments, a matrix may refer to the various components and organelles of a cell, for example, the cytoskeleton (e.g., actin and tubulin), endoplasmic reticulum, Golgi apparatus, vesicles, etc. In embodiments, the matrix is endogenous to a cell. In embodiments, the matrix is exogenous to a cell. In embodiments, the matrix includes both the intracellular and extracellular components of a cell. In embodiments, polynucleotide primers may be immobilized on a matrix including the various components and organelles of a cell. Immobilization of polynucleotide primers on a matrix of cellular components and organelles of a cell is accomplished as described herein, for example, through the interaction/reaction of complementary bioconjugate reactive moieties. In embodiments, the exogenous polymer may be a matrix or a network of extracellular components that act as a point of attachment (e.g., act as an anchor) for the cell to a substrate.

In embodiments, the cell is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissue include those from skin tissue, muscle tissue, bone tissue, organ tissue and the like. In embodiments, the method includes immobilizing the cell in situ to a substrate and permeabilized for delivering probes, enzymes, nucleotides and other components required in the reactions. In embodiments, the cell includes many cells from a tissue section in which the original spatial relationships of the cells are retained. In embodiments, the cell in situ is within a Formalin-Fixed Paraffin-Embedded (FFPE) sample. In embodiments, the cell is subjected to paraffin removal methods, such as methods involving incubation with a hydrocarbon solvent, such as xylene or hexane, followed by two or more washes with decreasing concentrations of an alcohol, such as ethanol. The cell may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the cell is fixed with a chemical fixing agent. In embodiments, the chemical fixing agent is formaldehyde or glutaraldehyde. In embodiments, the chemical fixing agent includes both formaldehyde and glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv®, FineFIX®, RCL2/KIN-Fix, UMFIX, Glyo-Fixx®, Histochoice®, or PAXgene®. In embodiments, the cell is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments the cell is lysed to release nucleic acid or other materials from the cells. For example, the cells may be lysed using reagents (e.g., a surfactant such as Triton™-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.). The cells may release, for instance, DNA, RNA, mRNA, proteins, or enzymes. The cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include dissociating the cell from the tissue or the cellular microenvironment. In embodiments, the method does not include lysing the cell.

In embodiments, the method further includes subjecting the cell to expansion microscopy methods and techniques. Expansion allows individual targets (e.g., mRNA or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety.

In embodiments, the method does not include subjecting the cell to expansion microscopy. Typically, expansion microscopy techniques utilize a swellable polymer or hydrogel (e.g., a synthetic matrix-forming material) which can significantly slow diffusion of enzymes and nucleotides. Matrix (e.g., synthetic matrix) forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art. Additionally, expansion microscopy techniques may render the temperature of the cell sample difficult to modulate in a uniform, controlled manner. Modulating temperature provides a useful parameter to optimize amplification and sequencing methods. In embodiments, the method does not include an exogenous matrix.

In embodiments, the oligonucleotide contains one or more functional moieties (e.g., bioconjugate reactive groups) that serve as attachment points to the cell (i.e., the internal cellular scaffold) or to the matrix in which the cell is embedded (e.g. a hydrogel). In embodiments, the circularizable oligonucleotide contains one or more functional moieties (e.g., bioconjugate reactive groups) that serve as attachment points to the cell (i.e., the internal cellular scaffold) or to the matrix in which the cell is embedded (e.g. a hydrogel). In embodiments, the bioconjugate reactive group is located at the 5' and/or 3' end of the oligonucleotide. In embodiments, the bioconjugate reactive group is located at an internal position of the oligonucleotide e.g., the oligonucleotide contains one or more modified nucleotides, such as aminoallyl deoxyuridine 5'-triphosphate (dUTP) nucleotide(s). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, the oligonucleotide primer contains a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, prior to amplification, the modified nucleotide-containing primer is attached to the cell protein matrix by using a cross-linking reagent (e.g., an amine-reactive crosslinking agent with PEG spacers, such as (PEGylated bis(sulfosuccinimidyl)suberate) ($BS(PEG)_9$)).

In embodiments, the method further includes detecting a protein. In embodiments, an oligonucleotide barcode is associated with one or more targets (e.g., proteins). In embodiments, associating an oligonucleotide barcode with each of the plurality of targets includes contacting each of the targets with a specific binding reagent, wherein the specific binding reagent includes an oligonucleotide barcode. In embodiments, the method further includes hybridizing a padlock probe to two adjacent nucleic acid sequences of the barcode, wherein the padlock probe is a single-stranded polynucleotide having a 5' and a 3' end, and the padlock probe includes at least one primer binding sequence. In embodiments, the method further includes ligating the 5' and 3' ends of the padlock probe to form a circular polynucleotide. In embodiments, the probe includes a primer binding sequence from a known set of primer binding sequences. In embodiments, the probe includes a sequencing primer binding sequence from a known set of sequencing primer binding sequences. In embodiments, associating an oligonucleotide barcode with each of the plurality of targets includes contacting each of the targets with a specific binding reagent, wherein the specific binding reagent includes a circular polynucleotide which includes the oligonucleotide barcode. For example, in embodiments the specific binding reagent is bound (e.g., covalently linked via a tethered capture oligonucleotide, wherein the capture oligonucleotide is hybridized to the circular polynucleotide) to a circular polynucleotide before contacting the target. In embodiments, the specific binding reagent includes an antibody, single-chain Fv fragment (scFv), antibody fragment-antigen binding (Fab), or an aptamer. In embodiments, the specific binding reagent is an antibody, single-chain Fv fragment (scFv), antibody fragment-antigen binding (Fab), or an aptamer. In embodiments, the circular polynucleotide includes a primer binding sequence from a known set of primer binding sequences.

In embodiments, the targets are proteins or carbohydrates. In embodiments, the targets are proteins. In embodiments, the targets are carbohydrates. In embodiments when the target are proteins and/or carbohydrates, the method includes contacting the proteins with a specific binding reagent, wherein the specific binding reagent includes an oligonucleotide barcode (e.g., the target polynucleotide is attached to the specific binding reagent). In embodiments, the specific binding reagent includes an antibody, single-chain Fv fragment (scFv), antibody fragment-antigen binding (Fab), or an aptamer. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. In embodiments, the specific binding reagent interacts (e.g., contacts, or binds) with one or more specific binding reagents on the cell surface. Carbohydrate-specific antibodies are known in the art, see for example Kappler, K., Hennet, T. Genes Immun 21, 224-239 (2020). In embodiments, the target polynucleotide is polynucleotide attached to a specific binding reagent. In embodiments, the specific binding reagent is an antibody, single-chain Fv fragment (scFv), antibody fragment-antigen binding (Fab), or an aptamer. In embodiments, the protein-specific binding agent is an antibody, single-chain Fv fragment (scFv), antibody fragment-antigen binding (Fab), affimer, or an aptamer. In embodiments, the protein-specific binding agent is an antibody. In embodiments, the specific binding reagent is a single-chain Fv fragment (scFv). In embodiments, the specific binding reagent is an antibody fragment-antigen binding (Fab). In embodiments, the specific binding reagent is an affimer. In embodiments, the specific binding reagent is an aptamer.

In embodiments, the oligonucleotide is covalently attached to a protein-specific binding agent, wherein the protein-specific binding agent is an antibody, single-chain Fv fragment (scFv), affimer, aptamer, single-domain antibody (sdAb), or antibody fragment-antigen binding (Fab). In embodiments, the oligonucleotide is covalently attached to an antibody or single-domain antibody (sdAb). In embodiments, the oligonucleotide is covalently attached to an antibody. In embodiments, the oligonucleotide is covalently attached to a single-chain Fv fragment (scFv). In embodiments, the oligonucleotide is covalently attached to an affimer. In embodiments, the oligonucleotide is covalently attached to an aptamer. In embodiments, the oligonucleotide is covalently attached to a single-domain antibody (sdAb). In embodiments, the oligonucleotide is covalently attached to an antibody fragment-antigen binding (Fab). In embodiments, the oligonucleotide is covalently attached to an antibody or single-domain antibody (sdAb). The design and preparation of protein-specific binding agent oligonucleotide conjugates is known, for example various different binding moieties which may be used, the design of probe oligonucleotides, and the coupling of such oligonucleotides to the binding moieties to form the conjugates. The details and principles may be applied to the design of the probes for use in the methods described herein. For example, reference may be made to WO 2007/107743, U.S. Pat. Nos. 7,306,904 and 6,878,515 which are incorporated herein by reference.

In embodiments, the target polynucleotide is attached to a specific binding reagent (e.g., an antibody) via a linker (e.g., a bioconjugate linker). In embodiments, the target polynucleotide is attached to the specific binding reagent via a linker formed by reacting a first bioconjugate reactive moiety (e.g., the bioconjugate reactive moiety includes an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety) with a second bioconjugate reactive moiety). In embodiments, the target polynucleotide includes a barcode, wherein the barcode is a known sequence associated with the specific binding reagent. In embodiments, the barcode is at least 5, 6, 7, 8, 9, 10, 11, 12, 13, 14, or 15 nucleotides in length. In embodiments, the barcode is 5, 6, 7, 8, 9, 10, 11, 12, 13, 14, or 15 nucleotides in length.

Specific antibodies tagged with known oligonucleotide sequences can be synthesized by using bifunctional crosslinkers reactive towards thiol (via maleimide) and amine (via NHS) moieties. For example, a 5'-thiol-modified oligonucleotide could be conjugated to a crosslinker via maleimide chemistry and purified. The oligos with a 5'-NHS-ester would then be added to a solution of antibodies and reacted with amine residues on the antibodies surface to generate tagged antibodies capable of binding analytes with target epitopes. These tagged antibodies include oligonucleotide sequence(s). The one or more oligonucleotide sequences may include a barcode, binding sequences (e.g., primer binding sequence or sequences complementary to hybridization pads), and/or unique molecular identifier (UMI) sequences.

In embodiments, specific binding entails a binding affinity, expressed as a $K_D$ (such as a $K_D$ measured by surface plasmon resonance at an appropriate temperature, such as 37° C.). In embodiments, the $K_D$ of a specific binding interaction is less than about 100 nM, 50 nM, 10 nM, 1 nM, 0.05 nM, or lower. In embodiments, the $K_D$ of a specific binding interaction is about 0.01-100 nM, 0.1-50 nM, or 1-10 nM. In embodiments, the $K_D$ of a specific binding interaction is less than 10 nM. The binding affinity of an antibody can be readily determined by one of ordinary skill in the art (for example, by Scatchard analysis). A variety of immunoassay formats can be used to select antibodies specifically immunoreactive with a particular antigen. For example, solid-phase ELISA immunoassays are routinely used to select monoclonal antibodies specifically immunoreactive with an analyte. See Harlow and Lane, ANTIBODIES: A LABORATORY MANUAL, Cold Springs Harbor Publications, New York, (1988) for a description of immunoassay formats and conditions that can be used to determine specific immunoreactivity. Typically, a specific or selective reaction will be at least twice background signal to noise and more typically more than 10 to 100 times greater than background.

In another aspect is provided a method of sequencing an agent-mediated nucleic acid sequence of a cell, the method including administering a genetically modifying agent to the cell (e.g., administering a genetically modifying agent to a subject including the cell), and sequencing an agent-mediated nucleic acid sequence of the cell in situ as described herein.

In an aspect is provided a method of identifying a nucleic acid sequence as an agent-mediated nucleic acid sequence, the method including administering a genetically modifying agent to a cell, detecting whether an agent-mediated nucleic acid sequence is present in the cell by sequencing a plurality of target sequences according to the methods as described herein, and identifying the nucleic acid sequence as an agent-mediated nucleic acid sequence when the presence of the agent-mediated nucleic acid is detected in the cell. In embodiments, the method includes the following steps in situ for each of the plurality of target nucleic acids: (i) contacting a target polynucleotide complex in a cell or tissue with a probe oligonucleotide, thereby forming a probe polynucleotide complex, wherein the target polynucleotide complex includes a blocking oligonucleotide bound to a first sequence of a target polynucleotide, wherein the blocking oligonucleotide includes a probe hybridization sequence, and wherein the probe polynucleotide complex includes the probe oligonucleotide bound to a second sequence of the target polynucleotide and bound to the probe hybridization sequence, wherein the target sequence is between the first and second sequence; (ii) extending the probe oligonucleotide along the target sequence with a polymerase to generate an extension strand including a complement of the target sequence, and ligating the extension strand to the probe oligonucleotide hybridization sequence, thereby generating a circular oligonucleotide; (iii) amplifying the circular oligonucleotide by extending an amplification primer hybridized to the circular oligonucleotide with a strand-displacing polymerase, thereby generating an amplification product including multiple copies of the target sequence; and (iv) sequencing the amplification product detected in the cell or tissue from step (iii).

In an aspect is provided a method of identifying a cell that responds to a genetically modifying agent, the method including administering a genetically modifying agent to the cell, detecting whether an agent-mediated nucleic acid sequence is present in the cell by sequencing a plurality of target sequences according to the methods as described herein, and identifying a cell that responds to a genetically modifying agent when the presence of the agent-mediated nucleic acid is detected in the cell. In embodiments, the method includes the following steps in situ for each of the plurality of target nucleic acids: (i) contacting a target polynucleotide complex in a cell or tissue with a probe oligonucleotide, thereby forming a probe polynucleotide complex, wherein the target polynucleotide complex includes a blocking oligonucleotide bound to a first sequence of a target polynucleotide, wherein the blocking oligonucleotide includes a probe hybridization sequence, and wherein the probe polynucleotide complex includes the probe oligonucleotide bound to a second sequence of the target polynucleotide and bound to the probe hybridization sequence, wherein the target sequence is between the first and second sequence; (ii) extending the probe oligonucleotide along the target sequence with a polymerase to generate an extension strand including a complement of the target sequence, and ligating the extension strand to the probe oligonucleotide hybridization sequence, thereby generating a circular oligonucleotide; (iii) amplifying the circular oligonucleotide by extending an amplification primer hybridized to the circular oligonucleotide with a strand-displacing polymerase, thereby generating an amplification product including multiple copies of the target sequence; and (iv) sequencing the amplification product detected in the cell or tissue from step (iii).

In an aspect is provided a method of identifying an agent as a genetically modifying agent, the method including administering an agent to a cell, detecting whether an agent-mediated nucleic acid sequence is present in the cell by sequencing a plurality of target sequences according to any of the methods as described herein, and identifying the genetically modifying agent when the presence of the agent-mediated nucleic acid is detected in the cell. In embodiments, the method includes the following steps in situ for each of the plurality of target nucleic acids: (i) contacting a target polynucleotide complex in a cell or tissue with a probe oligonucleotide, thereby forming a probe polynucleotide complex, wherein the target polynucleotide complex includes a blocking oligonucleotide bound to a first sequence of a target polynucleotide, wherein the blocking oligonucleotide includes a probe hybridization sequence, and wherein the probe polynucleotide complex includes the probe oligonucleotide bound to a second sequence of the target polynucleotide and bound to the probe hybridization sequence, wherein the target sequence is between the first and second sequence; (ii) extending the probe oligonucleotide along the target sequence with a polymerase to generate an extension strand including a complement of the target sequence, and ligating the extension strand to the probe oligonucleotide hybridization sequence, thereby generating a circular oligonucleotide; (iii) amplifying the circular oligonucleotide by extending an amplification primer hybridized to the circular oligonucleotide with a strand-displacing polymerase, thereby generating an amplification product including multiple copies of the target sequence; and (iv) sequencing the amplification product detected in the cell or tissue from step (iii).

In embodiments, the genetically modifying agent is a pathogen. In embodiments, the genetically modifying agent is a virus. In embodiments, the genetically modifying agent is a DNA virus (e.g., pox virus, herpesvirus, adenovirus, parvovirus, or warts virus). In embodiments, the genetically modifying agent is an RNA virus (e.g., influenza virus, rotavirus, mumps virus, rabies virus, eastern equine encephalitis virus, corona virus, LCM virus, polio virus, or HIV virus). In embodiments, the genetically modifying agent is a toxin. In embodiments, the genetically modifying agent is a peptide. In embodiments, the genetically modifying agent is a prion. In embodiments, the genetically modifying agent is a small molecule (e.g., a pharmaceutical agent).

III. Compositions & Kits

In an aspect is provided a cell or tissue including a target polynucleotide complex as described herein. In embodiments, the target polynucleotide complex includes a first sequence of a blocking oligonucleotide bound to a first sequence of a target polynucleotide; a first sequence of a probe oligonucleotide bound to a second sequence of the target polynucleotide; wherein the first and second sequences of the target polynucleotide are separated by 1 or more nucleotides; and where a second sequence of the blocking oligonucleotide is bound to a second sequence of the probe oligonucleotide. In embodiments, the target polynucleotide complex is formed by: (i) contacting the target polynucleotide with a blocking oligonucleotide including a first target hybridization sequence and a probe hybridization sequence, and (ii) hybridizing the first target hybridization sequence to the target polynucleotide.

In embodiments, the cell is attached to a substrate. In embodiments, the cell is attached to the substrate via a bioconjugate reactive moiety. In embodiments, the cell is attached to a well of a microplate (e.g., a microplate including a plurality of wells, wherein one or more wells include a plurality of cells). In embodiments, each cell of the one or more wells includes the complex. In embodiments, each cell of the one or more wells includes a plurality of complexes. In embodiments, the complex in each well of the plurality of wells includes a different subject sequence. In embodiments, the complex in each cell of the plurality of wells includes the same subject sequence. In embodiments, the cells in each well include a plurality of different complexes (e.g., the plurality of cells in the well include one or more complexes including different subject sequences, or complements thereof). In embodiments, the complex is within a cell or tissue sample. In embodiments, the cell including the complex is within a tissue section.

In embodiments, the cell or tissue sample is cleared (e.g., digested) of proteins, lipids, or proteins and lipids. In embodiments, the cell or tissue sample is processed according to a known technique in the art, for example CLARITY (Chung K., et al. Nature 497, 332-337 (2013)), PACT-PARS (Yang B et al. Cell 158, 945-958 (2014).), CUBIC (Susaki E. A. et al. Cell 157, 726-739 (2014)., 18), ScaleS (Hama H., et al. Nat. Neurosci. 18, 1518-1529 (2015)), OPTIClear (Lai H. M., et al. Nat. Commun. 9, 1066 (2018)), Ce3D (Li W., et al. Proc. Natl. Acad. Sci. U.S.A. 114, E7321-E7330 (2017)), BABB (Dodt H. U. et al. Nat. Methods 4, 331-336 (2007)), iDISCO (Renier N., et al. Cell 159, 896-910 (2014)), uDISCO (Pan C., et al. Nat. Methods 13, 859-867 (2016)), FluoClearBABB (Schwarz M. K., et al. PLOS ONE 10, e0124650 (2015)), Ethanol-ECi (Klingberg A., et al. J. Am. Soc. Nephrol. 28, 452-459 (2017)), and PEGASOS (Jing D. et al. Cell Res. 28, 803-818 (2018)).

In an aspect is provided a kit useful for performing the methods as described herein. In embodiments, the kit includes a blocking oligonucleotide including a first target hybridization sequence, a first curl sequence and a second curl sequence, and a probe hybridization sequence, wherein the first curl sequence is complementary to the second curl sequence; and a probe oligonucleotide including a second target hybridization sequence and a blocking hybridization sequence. In embodiments, the kit includes a plurality of blocking oligonucleotide and a plurality of probe oligonucleotides.

In embodiments, each target hybridization sequence of the plurality of probe oligonucleotides is complementary to a different sequence of the target polynucleotide (e.g., is complementary to a different probe hybridization sequence in a target polynucleotide). In embodiments, each target hybridization sequence of the plurality of probe oligonucleotides is complementary to a different sequence of a different target polynucleotide (e.g., is complementary to a different probe hybridization sequence in different target polynucleotides). In embodiments, each target hybridization sequence of the plurality of probe oligonucleotides is complementary to a different sequence of the same target polynucleotide (e.g., is complementary to a different probe hybridization sequence in the same target polynucleotide). In embodiments, the target hybridization sequence of the probe oligonucleotide is greater than 30 nucleotides. In embodiments, the target hybridization sequence of the probe oligonucleotide is about 5 to about 35 nucleotides in length. In embodiments, the target hybridization sequence is about 12 to 15 nucleotides in length. In embodiments, the target hybridization sequence is about 35 to 40 nucleotides in length to maximize specificity. In embodiments, the target hybridization sequence is greater than 12 nucleotides in length. In embodiments, the target hybridization sequence is about 5, about 10, about 15, about 20, about 25, about 30, or about 35 nucleotides in length. In embodiments, the target hybridization sequence of each oligonucleotide primer is a single stranded polynucleotide that is at least 50% complementary, at least 75% complementary, at least 85% complementary, at least 90% complementary, at least 95% complementary, at least 98%, at least 99% complementary, or 100% complementary to a portion of a target polynucleotide. In embodiments, the target hybridization sequence of each probe oligonucleotide are complementary to portions of the same target polynucleotide that are separated by about 10, about 15, about 20, about 25, about 30, about 35, about 40, about 45, about 50, about 75, about 100, about 125, about 150, about 175, about 200, about 225, about 250, about 275, about 300, about 325, about 350, about 375, about 400, about 425, about 450, about 475, or about 500 nucleotides. In embodiments, the target hybridization sequence of each probe oligonucleotide is complementary to portions of the same target polynucleotide that are separated by about or more than about 10, 15, 20, 25, 30, 35, 40, 45, 50, 75, 100, 125, 150, 175, 200, 225, 250, 275, 300, 325, 350, 375, 400, 425, 450, 475, or 500 nucleotides.

In embodiments, the probe oligonucleotide is about 50 to about 500 nucleotides in length. In embodiments, the probe oligonucleotide is about 50 to about 300 nucleotides in length. In embodiments, the probe oligonucleotide is about 80 to about 300 nucleotides in length. In embodiments, the probe oligonucleotide is about 50 to about 150 nucleotides in length. In embodiments, the probe oligonucleotide is about or more than about 40, 50, 75, 100, 125, 150, 175, 200, 250, 300, 350, 400, or 500 nucleotides in length. In embodiments, the probe oligonucleotide is less than about 50, 75, 100, 125, 150, 175, 200, 250, 300, 350, 400, or 500 nucleotides in length.

In embodiments, each probe oligonucleotide (e.g., each probe oligonucleotide of a plurality of probe oligonucleotides) includes a primer binding sequence (i.e., a sequence complementary to a primer, such as an amplification or sequencing primer). In embodiments, the splint oligonucleotide includes a primer binding sequence. In embodiments, the sequencing primer binding sequence is common among the plurality of probe oligonucleotides. In embodiments, the sequencing primer binding sequence is different among the plurality of probe oligonucleotides (e.g., a first subset of probe oligonucleotides include a first sequencing primer binding sequence and a second subset of probe oligonucleotides includes a second sequencing primer binding sequence).

In embodiments, each probe oligonucleotide includes about 50 to about 150 nucleotides. In embodiments, the blocking oligonucleotide includes about 30 to about 150 nucleotides. In embodiments, each probe oligonucleotide includes about 50 to about 300 nucleotides. In embodiments, the blocking oligonucleotide includes about 30 to about 300 nucleotides. In embodiments, the blocking oligonucleotide includes about 50 to about 300 nucleotides. In embodiments, each probe oligonucleotide includes about or more than about 50, 75, 100, 125, 150, 175, 200, 250, 300, 350, 400, or 500 nucleotides. In embodiments, the blocking oligonucleotide includes about or more than about 30, 50, 75, 100, 125, 150, 175, 200, 250, 300, 350, 400, or 500 nucleotides. In embodiments, each probe oligonucleotide includes less than about 50, 75, 100, 125, 150, 175, 200, 250, 300, 350, 400, or 500 nucleotides. In embodiments, the blocking oligonucleotide includes less than about 30, 50, 75, 100, 125, 150, 175, 200, 250, 300, 350, 400, or 500 nucleotides.

In embodiments, a kit includes labeled nucleotides including differently labeled nucleotides, enzymes, buffers, oligonucleotides, and related solvents and solutions. In embodiments, the kit includes one or more oligonucleotide probes (e.g., an oligonucleotide probe as described herein). The kit may also include a template nucleic acid (DNA and/or RNA), one or more primer polynucleotides, nucleoside triphosphates (including, e.g., deoxyribonucleotides, dideoxynucleotides, ribonucleotides, labeled nucleotides, and/or modified nucleotides), buffers, salts, and/or labels (e.g., fluorophores). In embodiments, the kit includes components useful for circularizing template polynucleotides using a ligation enzyme (e.g., Circligase™ enzyme, Taq DNA Ligase, HiFi Taq DNA Ligase, T4 ligase, SplintR® ligase, or Ampligase® DNA Ligase). For example, such a kit further includes the following components: (a) reaction buffer for controlling pH and providing an optimized salt composition for a ligation enzyme (e.g., Circligase™ enzyme, Taq DNA Ligase, HiFi Taq DNA Ligase, T4 ligase, SplintR® ligase, or Ampligase® DNA Ligase), and (b) ligation enzyme cofactors. In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label. In embodiments, the kit includes a modified terminal deoxynucleotidyl transferase (TdT) enzyme.

In embodiments, the kit includes a microplate, and reagents for sample preparation and purification, amplification, and/or sequencing (e.g., one or more sequencing reaction mixtures). In embodiments, the kit includes a flow cell, and reagents for sample preparation and purification, amplification, and/or sequencing (e.g., one or more sequencing reaction mixtures). In embodiments, the kit includes reagents for protein detection includes a plurality of specific binding agents linked to an oligonucleotide (e.g., DNA-conjugated antibodies).

In embodiments, the kit further includes a ligase. In embodiments, the kit includes one or more ligases. In embodiments, the kit includes a plurality of ligases. In embodiments, the kit further includes a polymerase. In embodiments, the kit further includes one or more polymerases. In embodiments, the kit includes a plurality of polymerases. In embodiments, the kit includes a ligase and one or more polymerases. In embodiments, the one or more polymerases include a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase. In embodiments, the polymerase is a *Thermus thermophilus* (Tth) DNA polymerase or mutant thereof. In embodiments, the polymerase is a Reverse Transcription Xenopolymerase (RTX). In embodiments, the polymerase is a mutant M-MLV reverse transcriptase from the Moloney murine leukemia virus.

In embodiments, the kit further includes an exonuclease, wherein the exonuclease is capable of removing a single-stranded nucleic acid sequence. In embodiments, the exonuclease is Exonuclease I. In embodiments, the exonuclease is Exonuclease T. In embodiments, the kit further includes an exonuclease-compatible buffer (e.g., a buffer wherein the exonuclease retains catalytic activity).

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator™ γ, 9° N polymerase (exo-), Therminator™ II, Therminator™ III, or Therminator™ IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can include one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffered solution can contain one or more divalent cations at a concentration sufficient to permit hybridization of a nucleic acid. In embodiments, the buffered solution includes about 10 mM Tris, about 20 mM Tris, about 30 mM Tris, about 40 mM Tris, or about 50 mM Tris. In embodiments the buffered solution includes about 50 mM NaCl, about 75 mM NaCl, about 100 mM NaCl, about 125 mM NaCl, about 150 mM NaCl, about 200 mM NaCl, about 300 mM NaCl, about 400 mM NaCl, or about 500 mM NaCl. In embodiments, the buffered solution includes about 0.05 mM EDTA, about 0.1 mM EDTA, about 0.25 mM EDTA, about 0.5 mM EDTA, about 1.0 mM EDTA, about 1.5 mM EDTA or about 2.0 mM EDTA. In embodiments, the buffered solution includes about 0.01% Triton X-100, about 0.025% Triton X-100, about 0.05% Triton X-100, about 0.1% Triton X-100, or about 0.5% Triton X-100. In embodiments, the buffered solution includes 20 mM Tris pH 8.0, 100 mM NaCl, 0.1 mM EDTA, 0.025% Triton X-100. In embodiments, the buffered solution includes 20 mM Tris pH 8.0, 150 mM NaCl, 0.1 mM EDTA, 0.025% Triton X-100. In embodiments, the buffered solution includes 20 mM Tris pH 8.0, 300 mM NaCl, 0.1 mM EDTA, 0.025% Triton X-100. In embodiments, the buffered solution includes 20 mM Tris pH 8.0, 400 mM NaCl, 0.1 mM EDTA, 0.025% Triton X-100. In embodiments, the buffered solution includes 20 mM Tris pH 8.0, 500 mM NaCl, 0.1 mM EDTA, 0.025% Triton X-100. In embodiments, the buffered solution includes 50 mM Tris pH 8.0, 75 mM LiCl, 3 mM $MgCl_2$, 0.025% Triton™ X-100, 0.1 mM ATP, and 10 mM DTT. In embodiments, the buffered solution includes 500 mM Tris pH 7.5, 100 mM $MgCl_2$, 0.25% Triton™ X-100, 10 mM ATP, and 100 mM DTT.

In embodiments the buffered solution includes about 50 mM NaCl, about 75 mM NaCl, about 100 mM NaCl, about 125 mM NaCl, about 150 mM NaCl, about 200 mM NaCl, about 300 mM NaCl, about 400 mM NaCl, or about 500 mM NaCl. In embodiments, the buffered solution includes about 0.01% Triton™ X-100, about 0.025% Triton™ X-100, about 0.05% Triton™ X-100, about 0.1% Triton™ X-100, about 0.25% Triton™ X-100, or about 0.5% Triton™ X-100. In embodiments, the buffered solution includes 0.5% glycerol, 1% glycerol, 2.5% glycerol, 5% glycerol, 10% glycerol, 15 glycerol, 20% glycerol, 10% glycerol, 15% glycerol, 20% glycerol, 25% glycerol, 30% glycerol, 35% glycerol, 40% glycerol, 45% glycerol, or 50% glycerol. In embodiments, the buffered solution includes 0.1 mM DTT, 0.5 mM DTT, 1 mM DTT, 2 mM DTT, 3 mM DTT, 4 mM DTT, 5 mM DTT, 6 mM DTT, 7 mM DTT, 8 mM DTT, 9 mM DTT, 10 mM DTT, 11 mM DTT, 12 mM DTT, 13 mM DTT, 14 mM DTT, 15 mM DTT, 16 mM DTT, 17 mM DTT, 18 mM DTT, 19 mM DTT, or 20 mM DTT. Triton™ is a registered trademark of Dow Chemical Company. In embodiments, the buffered solution includes about 1 mM $MgCl_2$, about 2 mM $MgCl_2$, about 3 mM $MgCl_2$, about 4 mM $MgCl_2$, about 5 mM $MgCl_2$, about 6 mM $MgCl_2$, about 7 mM $MgCl_2$, about 8 mM $MgCl_2$, about 9 mM $MgCl_2$, about 10 mM $MgCl_2$, about 11 mM $MgCl_2$, about 12 mM $MgCl_2$, about 13 mM $MgCl_2$, about 14 mM $MgCl_2$, about 15 mM $MgCl_2$, about 16 mM $MgCl_2$, about 17 mM $MgCl_2$, about 18 mM $MgCl_2$, about 19 mM $MgCl_2$, or about 20 mM $MgCl_2$. In embodiments, the buffered solution includes about 0.01 mM ATP, about 0.05 mM ATP, about 0.1 mM ATP, about 0.25 mM ATP, about 0.5 mM ATP, about 0.75 mM ATP, about 1 mM ATP, about 2 mM ATP, about 3 mM ATP, about 4 mM ATP, about 5 mM ATP, about 6 mM ATP, about 7 mM ATP, about 8 mM ATP, about 9 mM ATP, or about 10 mM ATP. In embodiments, the buffered solution includes about 25 mM LiCl, about 50 mM LiCl, about 75 mM LiCl, about 100 mM LiCl, about 125 mM LiCl, about 150 mM LiCl, about 175 mM LiCl, about 200 mM LiCl, about 225 mM LiCl, about 250 mM LiCl, about 275 mM LiCl, about 300 mM LiCl, about 325 mM LiCl, about 350 mM LiCl, about 375 mM LiCl, about 400 mM LiCl, about 425 mM LiCl, about 450 mM LiCl, about 475 mM LiCl, or about 500 mM LiCl.

In embodiments, the kit includes one or more sequencing reaction mixtures. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, digital storage medium, etc., on which the information has been recorded. Yet another means that may be present is a website address which may be used via the Internet to access the information at a removed site. Any convenient means may be present in the kits.

Adapters and/or primers may be supplied in the kits ready for use, as concentrates-requiring dilution before use, or in a lyophilized or dried form requiring reconstitution prior to use. If required, the kits may further include a supply of a suitable diluent for dilution or reconstitution of the primers and/or adapters. Optionally, the kits may further include supplies of reagents, buffers, enzymes, and dNTPs for use in carrying out nucleic acid amplification and/or sequencing. Further components which may optionally be supplied in the kit include sequencing primers suitable for sequencing templates prepared using the methods described herein.

In embodiments, the kit can further include one or more biological stain(s) (e.g., any of the biological stains as described herein). For example, the kit can further include eosin and hematoxylin. In other examples, the kit can include a biological stain such as acridine orange, Bismarck brown, carmine, coomassie blue, crystal violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof. In embodiments, the kit is designed for staining tissue samples for imaging and detecting target molecules (e.g., proteins and/or nucleic acids) can be significantly expanded beyond the inclusion of fluorophores. For instance, the kit can include eosin and hematoxylin, which are classic histological stains. Eosin, a red dye, typically stains acidic components of the cell such as cytoplasmic proteins, while hematoxylin, a basic dye, binds to nucleic acids, coloring the cell nucleus blue. This combination is widely used in histopathology for detailed tissue structure visualization. Moreover, the kit can encompass stains such as acridine orange, a nucleic acid-selective fluorescent cationic dye, and Bismarck brown, which is often used for staining backgrounds in histological tissue sections. Carmine, another potential inclusion, is a natural red dye used for staining glycogen, while Coomassie blue is a popular choice for protein staining in gel electrophoresis. Crystal violet, a triarylmethane dye, can be included for staining cell walls and nuclei, and DAPI, a fluorescent stain that binds strongly to A-T rich regions in DNA, is useful in fluorescence microscopy. Ethidium bromide, a fluorescent intercalator, is also a valuable addition for its role in nucleic acid staining, especially in gel electrophoresis. Further, the kit can include acid fuchsine, used in Masson's trichrome stain; Hoechst stains, which are cell-permeable, DNA-specific blue fluorescent dyes; and iodine, commonly used in Gram staining and for staining starch in plant cells. Methyl green and methylene blue, both traditional histological stains, can be included for their affinity towards nucleic acids. Neutral red, a vital stain that accumulates in lysosomes, Nile blue and Nile red, both used for staining lipids, and osmium tetroxide, a heavy metal stain for lipid bilayers in electron microscopy, can be part of the kit. Propidium iodide, a popular red-fluorescent nuclear and chromosome counterstain, along with rhodamine, may be utilized. Safranin, commonly used in Gram staining, can be included for its ability to stain cell components like nuclei, cytoplasm, and cell walls in various colors, enhancing the contrast and detail in tissue imaging.

In an aspect is provided a solid support comprising one or more tissue sections, wherein the tissues include a plurality of compositions and/or complexes as described herein. In embodiments, the tissue includes liver tissue, kidney tissue, bone tissue, lung tissue, thymus tissue, adrenal tissue, skin tissue, bladder tissue, colon tissue, spleen tissue, or brain tissue.

EXAMPLES

Example 1. Sequencing Nucleic Acid Molecules in Cells and Tissues

A foundational aim of genetics is understanding the genetic causes of behavioral traits, with a particular focus on human diseases, plant science, agriculture, and microbiology. As of this publication, we are approaching three decades since the publication of the reference human genome, and with hundreds of thousands of sequenced genomes in the intervening time, the challenge has shifted from one of data generation to one of data interpretation. Providing a more complete picture, recent application of different individual -omic studies (e.g., gen-omics, epigen-omics, transcript-omics, prote-omics, metagen-omics) help to solve broader queries pertaining to basic and applied areas of science, providing greater insight into biological functions.

A wealth of information is reflected in the temporal and spatial variation of gene and protein expression among cells. Cellular macromolecules such as nucleic acids and proteins, occupy precise positions in cells and tissues, and a great deal of information is lost when these molecules are extracted. The methods available today for RNA sequence analysis (RNA-Seq) have the capacity to quantify the abundance of RNA molecules in a population of cells with great sensitivity. Current methods for single-cell RNA and protein analysis typically involve some method for "barcoding" the content of individual cells, followed by pooling the content and sequencing on a commercial DNA sequencing device (e.g., Singular Genomics G4™ Sequencer, Illumina NextSeq™ 500/550, MiSeq™, HiSeq™ 2500/3000/4000, or NovaSeq™). The barcoding can be done in individual wells on a microplate (e.g., a microplate with 96, 384, or 1536 wells), and more recently droplet-based methods are emerging as an essential tool for single-cell genomics research (see for example, Klein A. and Macosko E. Lab Chip. 2017; 17(15):2540-2541; and Zheng, G. X., et al. Nature communications, 2017; 8, 14049). Briefly, droplet-based methods begin with isolating a cell from a sample (e.g., a tissue) and encapsulating the cell in a droplet where unique identifying oligonucleotides (i.e., barcodes) are incorporated into the genomic sequence, often while converting RNAs to cDNAs during reverse transcription. These barcodes uniquely label the cDNA and identify the cellular origin. The cDNAs are then extracted and undergo standard library preparation for sequencing before being sequenced on a commercial sequencer. RNA expression is then quantified by counting the number of barcodes that mapped to each cell.

Existing methods have found wide application dissecting transcriptomic heterogeneity, and can handle upwards of 10,000 cells in an automated format, however they have several limitations and drawbacks. For example, if the cells of interest originate from a tissue sample, all information about the spatial distribution of the cells within the tissue is lost in the process of dissociating and isolating the cells prior to barcoding them. Often information about the intracellular distribution of analytes within the cellular microenvironment is also lost. This information can be vital to designing therapeutic approaches to cancers, for example, where the tumor microenvironment often creates spatial gradients of nutrients and metabolic byproducts. Droplet-based techniques are capable of barcoding and sequencing tens of thousands of cells (e.g., 10-50 thousand cells) in a single experiment but current approaches require generation of custom microfluidic devices, reagents, and sample preparation techniques (e.g., as found in the disclosures RE41,780 and US 2015/0225778). Additionally, due to the digital "counting" nature of the sequencing readout, hundreds of sequencing reads/cell are required to get information about the expression of less abundant genes. For example, if a particular abundant gene is transcribed into 500 copies of RNA, the abundant gene will dominate the sequencing run resulting in relatively inefficient use of sequencing capacity. However, cells can associate with multiple barcodes which significantly impacts single-cell analyses and rare cell events (Lareau, C. A., et al. (2020) *Nature communications,* 11(1), 866).

A different barcoding approach has been applied to spatial profiling of RNA & proteins in tissue. An example of this is the method developed by Spatial Transcriptomics, a Stockholm-based company purchased by 10× Genomics in 2018 and recently commercialized as "Visium Spatial" platform. This approach involves attaching a section of a frozen tissue of interest to patterned microarrays carrying spatially barcoded oligo-dT primers that capture the entire polyadenylated transcriptome contained in the tissue section. Each spot on the microarray contains a capture probe with a spatial barcode unique to that spot allowing the individual sequencing reads to be mapped to the originating spot. After cDNA synthesis on the surface via reverse transcription, the tissue is removed and the mRNA-cDNA hybrids are released from the array to be prepared for sequencing; see Vickovic, S., et al. Nat. Methods 16, 987-990 (2019) for greater detail on the approach. The current implementation of this technology includes a microarray with 100 μm spots spaced equidistant from each other, approximately 200 μm apart. The spatial resolution of this method is approximately 100 μm, which is sufficient for a coarse mapping of a pathology sample, but is insufficient to resolve individual cells, which are approximately 10-20 μm, or subcellular features (i.e., features less than 10 μm, such as the mitochondria). Wide adoption of this approach has been limited by the lack of scalability and accessible ways to automate and/or parallelize sequencing library preparation.

A number of new techniques have been described for reading out RNA transcription levels in tissue sections directly (i.e., in-situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization) and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation,* (2019) UC San Diego. ProQuest ID: Cai_ucsd_0033D_18822; and Sansone, A. Nat Methods 16, 458; 2019). In all of these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted. This increases the complexity and costs of detection, and can require laborious sample preparation and significant time consuming wash protocols. Additionally, highly multiplexed approaches cannot readily distinguish barcodes with a diversity in excess of $10^2$-$10^3$ (Chen K. et al. Science. 2015; 348:aaa6090)

Gap fill padlock probes (PLPs) are extremely useful when there is an unknown region on a target RNA or DNA molecule flanked by conserved and known sequences (e.g., a left flanking region and a right flanking region). Typically, gap fill PLPs include a first hybridization pad (i.e., a first hybridization domain complementary to a first target sequence) and a second hybridization pad (i.e., a second hybridization domain complementary to a second target sequence) which can each be directly targeted, for example, to the conserved and known sequences surrounding an unknown sequence. By polymerizing (e.g., with a DNA polymerase) the gap between the two hybridization pads, the reverse complement of the unknown sequence is incorporated into the PLP, which, upon ligation, becomes a circular template for rolling circle amplification (RCA), and may thus be detected (see for example the top of FIG. 1). Occasionally the target sequence of interest (e.g., the mRNA sequence) may fold into complex secondary and tertiary structures, resulting in the formation of hairpin loops, pseudoknots, and other structures that can retard or stall the progression of a polymerase. Yet, while a strand-displacing polymerase can copy the target sequence despite having secondary structure elements, it will also unproductively displace the 5' end of the circularizable oligonucleotide; see the bottom of FIG. 1. When the 5' hybridization sequence of the circularizable oligonucleotide is displaced, the two ends cannot be ligated to form a circular oligonucleotide and thus cannot be amplified via a rolling circle mechanism, and thus minimizes the ability to detect the target sequence. Described herein are methods for addressing these and other problems in the art.

The method utilizes two different oligonucleotides: a blocking oligonucleotide (FIG. 2A) and a probe oligonucleotide (FIG. 2B). The blocking oligonucleotide includes a first sequence, A', complementary to a first sequence of a target nucleic acid molecule. The blocking oligonucleotide also includes a second complementary sequence, B', wherein B' is complementary to a second sequence of the target nucleic acid molecule. It is understood that A' and B' may form part of the same sequence, wherein B' is the downstream region or portion of the sequence. The second sequence of the blocking oligonucleotide, B' is also complementary to a third sequence of the blocking oligonucleotide, referred to as B in FIG. 2A. Thus, in embodiments, the third sequence (i.e., the B sequence) is substantially homologous or substantially identical to a sequence of the target polynucleotide. The B' and B sequences may also be referred to herein as "curl sequences." Under suitable hybridization conditions, the second and third sequences of the blocking oligonucleotide may hybridize together, as illustrated in the bottom of FIG. 2A. The blocking oligonucleotide further includes a fourth sequence, C, which is complementary to a portion of the probe oligonucleotide. FIG. 2B provides an illustration of an embodiment of the probe oligonucleotide, wherein the probe oligonucleotide is a linear, single-stranded oligonucleotide that includes a first sequence, C', which is complementary to the fourth sequence of the blocking oligonucleotide (i.e., C of FIG. 2A), and a second sequence, D', complementary to a third sequence of the target nucleic acid molecule. Though not included in the illustration, the probe oligonucleotide may further include one or more primer binding sites (e.g., sequences complementary to an amplification and/or sequencing primer). The probe oligonucleotide may further include one or more barcode or identifying sequences.

The probe oligonucleotide and blocking oligonucleotide are incubated with the cell or tissue that includes the target nucleic acid molecule. The target nucleic acid molecule may be within a cell or tissue that is attached to a substrate surface, wherein the cell or tissue is fixed (e.g., using a fixing agent) and permeabilized according to known methods. The cell may have been cultured on the surface, or the cell may have been initially cultured in suspension and then fixed to the surface. FIGS. 3A-3C provides an illustration of the two oligonucleotides when bound to a target nucleic acid molecule (FIG. 3A), the intermediate complex (FIG. 3B), and the resultant circular oligonucleotide (FIG. 3C). The nucleic acid molecule (e.g., mRNA, oncogene, or other nucleic acid sequence of interest) may present within the cell, or within the extracellular matrix.

As described further herein, the first and second sequences of the blocking oligonucleotide (represented as A' and B') hybridize to the target nucleic acid molecule, wherein the A' and B' hybridize to complementary regions adjacent to a target sequence of interest. The first sequence of the probe oligonucleotide hybridizes to the fourth sequence of the blocking oligonucleotide. The second sequence of the probe oligonucleotide, D', also binds to a flanking sequence of the target nucleic acid molecule, and a polymerase (depicted as the cloud) extends the second sequence to generate a complement of the target sequence. Following extension the probe oligonucleotide may anneal to the target polynucleotide (top of FIG. 3B) or it may anneal to the complementary sequence of the template switching oligonucleotide (bottom of FIG. 3B). Both intermediates exist under thermal equilibrium. A ligase (not shown) covalently attaches the extended complement to the first sequence, C', of the probe oligonucleotide, thereby forming a circular oligonucleotide depicted in FIG. 3C.

The circular oligonucleotide may be amplified, for example via rolling circle amplification (RCA) or exponential rolling circle amplification (eRCA). For example, the circular oligonucleotide may be primed with an amplification primer and extended with a strand-displacing polymerase to generate a concatemer containing multiple copies of the target nucleic acid sequence. The initial target molecule may serve as an amplification primer, for example by adding an exonuclease enzyme or an enzyme having exonuclease activity (e.g., phi29) and digesting a single-stranded region not hybridized to the probe or the blocking oligonucleotide. The initial target molecule may then be extended with a polymerase using the circular oligonucleotide as a template. Alternatively, the blocking oligonucleotide may be used as the amplification primer. In embodiments, an amplification primer is a primer added to the cell or tissue after formation of the circular oligonucleotide. In embodiments, the amplification primer is a primer that has been immobilized to a cellular component or a polymer matrix within the cell or tissue. The target nucleic acid sequence may then be subjected to multiple rounds of in situ sequencing, generated one or more sequencing reads and identifying the target nucleotide sequence.

We proceeded to use the methods described herein to perform in situ spatial sequencing using gapped padlock probes targeting mRNA transcripts directly. All steps were performed in 96-well plate format. Cell suspensions were centrifuged for 5 min at 0.3 rcf and resuspended in 1×PBS prior to plating. Cells were plated at a density of 100,000 live cells/well and allowed to settle at the bottom of the plate for at least 30 min at 4° C. Cells were then fixed with 4% formaldehyde in 1×PBS for 15 min at room temperature (RT), and washed 3 times with 1×PBS to remove the formaldehyde. Cells were then permeabilized with 0.5% Triton X-100 in 1×PBS for 20 min at RT, then washed 1× with 1×PBS and 2× with hybridization buffer (20% formamide and 2×SSC in water). Alternative permeabilization methods may be used, such as with the use of other detergents such as NP-40, Dodecyl-β-D-maltoside, or saponin. In addition, the use of detergent-free freeze-thawing can help to permeabilize cell membranes. Finally, the cell wall may be breached using physical or ultrasonic disruption and heat shock.

Blocking oligonucleotides were added at a final concentration of 100 nM each in probe hybridization buffer. The plate was heated to 60° C. and incubated for 30 minutes, followed by cooling to 37° C. The wells were washed with probe hybridization buffer 3 times to remove residual unbound oligonucleotides, then 100 nM probe oligonucleotides in probe hybridization buffer was added and incubated at 37° C. The wells were washed with probe hybridization buffer. Next, a mutant reverse transcriptase, ligase, and dNTPs (0.3 mM each) in 1×PCR buffer was incubated added to the wells. The plate was incubated at 37° C. for 2 hours to complete extension and ligation. Cells were then washed 1× with 1×PBS and 2× with hybridization buffer.

Phosphorothioated amplification primer was added at a final concentration of 0.5 uM in hybridization buffer and incubated for 1 hr at 37° C. Cells were then washed 1× with hybridization buffer and 2× with 1×PBS. A mutant version of phi29 DNA polymerase was then added at a final concentration of 0.45 uM with 1 M betaine, dNTPs (0.5 mM each), 0.125 mM aminoallyl-dUTP, 0.2 mg/mL BSA, 4 mM DTT, and 0.2 U/uL SUPERase-In™ RNase inhibitor in DEPC-treated water and incubated for an RCA reaction for 1 hr at 37° C. Cells were then washed 3× with 1×PBS.

Optionally, the RCA reaction can be done with modified nucleotides that contain chemical groups that serve as attachment points to the cell or the matrix in which the cell is embedded (e.g. a hydrogel). The attachment of the amplified product to the matrix can help confine & fix the amplicon to a small volume. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PE-Gylated bis(sulfosuccinimidyl)suberate) (BS(PEG)9)).

Optionally, one or more nucleotides within the amplification primer sequence, the sequencing primer sequence, and/or the immobilized oligonucleotide primer contains one or more functional moieties (e.g., bioconjugate reactive groups) that serve as attachment points to the cell or the matrix in which the cell is embedded (e.g., a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification, wherein each of the primer oligonucleotides are attached to a specific binding reagent. In embodiments, a plurality of oligonucleotide primers are provided to the matrix in which the cell is embedded prior to amplification. In embodiments, a plurality of oligonucleotide primers is provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as amino-allyl deoxyuridine 5'-triphosphate (dUTP) nucleotide(s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

Figure 5:
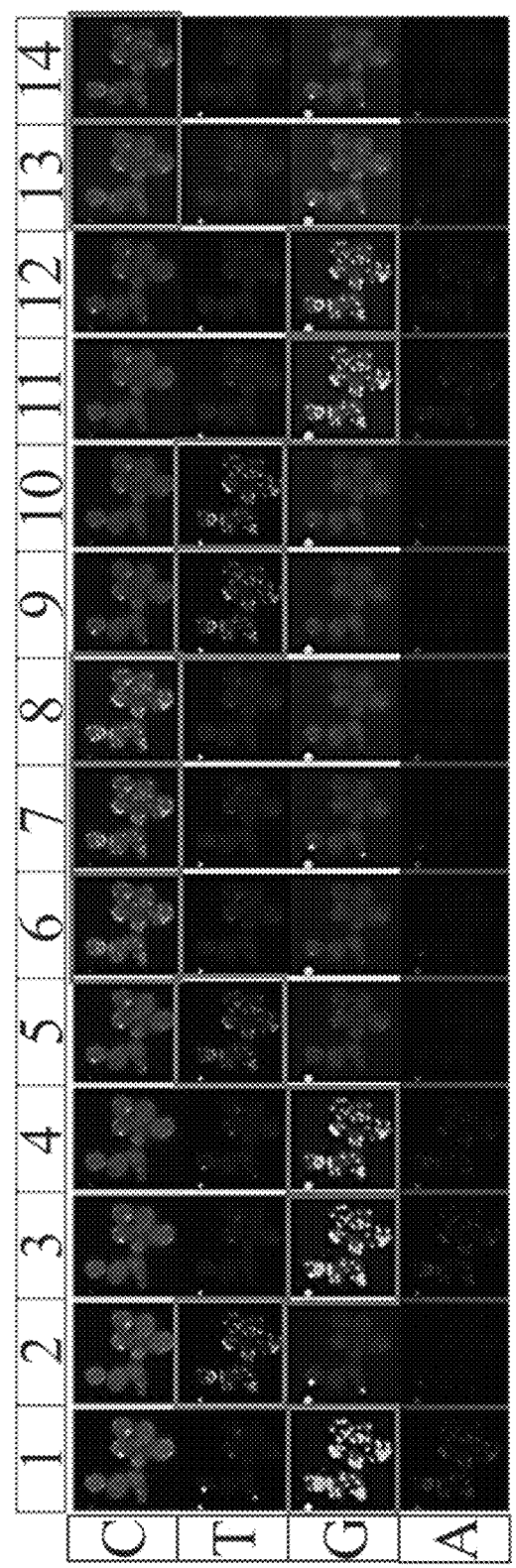
FIG. 5. presents a set of fluorescence microscopy images of in situ transcript sequencing through fourteen sequencing cycles performed in one well of a 96-well plate, wherein a circularizable probe and associated blocking oligonucleotide were targeted to an IgH transcript in Ramos Burkitt's lymphoma cells. The expected target sequence is 5'-GTGGTCCCTGGCC (SEQ ID NO:1), and the sequence retrieved is exactly that of the transcript.

TetraSpeck™ microspheres were added to cells at a final concentration of 0.1 nM in PBST (0.1% Tween-20 in 1×PBS) and allowed to settle for at least 30 min at RT, or centrifuged for 3 min at 2,000 RPM. Sequencing primer was then added at a final concentration of 0.5 uM in hybridization buffer and incubated for 30 min at 37° C. The cells were then washed 3× with flow cell wash buffer, and sequencing-by-synthesis with detectable nucleotides was performed. FIG. 5 presents a set of fluorescence microscopy images of in situ transcript sequencing through fourteen sequencing cycles performed in one well of a 96-well plate, wherein a circularizable probe and associated blocking oligonucleotide were targeted to an IgH transcript in Ramos Burkitt's lymphoma cells. The expected target sequence is 5'-GTGGTCCCTGGCC (SEQ ID NO:1), and the sequence retrieved is that of the transcript.

Figure 6:
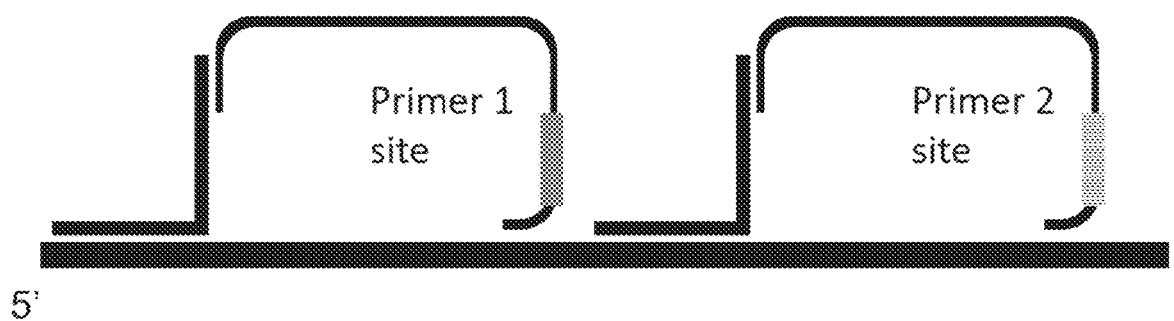
FIG. 6. A cartoon representation of a plurality of probe oligonucleotide hybridized to the same RNA molecule, albeit at different regions. The probe oligonucleotides include different sequencing primer binding sequences, labeled Primer site 1 and Primer site 2. A first sequencing primer may initiate a first sequencing read, followed by a second sequencing primer to initiate a second sequencing read. Applying the methods herein, such multiplexing of sequencing primers can be scaled to further reduce the effects of overlapping RNA density on resolving power. By such iterative means, two otherwise overlapping RNA transcripts are resolved. Alternatively, the oligonucleotide probes may be bound to different RNA molecules and include different sequencing primer binding sequences. Optionally, the sequencing cycle is terminated (e.g., incorporating dideoxynucleotides triphosphates (ddNTPs)). This process is repeated for the second and third barcodes, up to N number of primers in the set of primers.

In addition, the method described herein may be used with a plurality of probe oligonucleotides targeting the same RNA molecules. FIG. 6. A cartoon representation of a plurality of probe oligonucleotide hybridized to the same RNA molecule, albeit at different regions. The probe oligonucleotides include different sequencing primer binding sequences, labeled Primer site 1 and Primer site 2. A first sequencing primer may initiate a first sequencing read, followed by a second sequencing primer to initiate a second sequencing read. Applying the methods herein, such multiplexing of sequencing primers can be scaled to further reduce the effects of overlapping RNA density on resolving power. By such iterative means, two otherwise overlapping RNA transcripts are resolved. Alternatively, the oligonucleotide probes may be bound to different RNA molecules and include different sequencing primer binding sequences. Optionally, the sequencing cycle is terminated (e.g., incorporating dideoxynucleotides triphosphates (ddNTPs)). This process is repeated for the second and third barcodes, up to N number of primers in the set of primers.

Additional configurations for the substrate utilized with the method described herein are contemplated. In embodiments, the steps for performing in situ spatial sequencing in tissues using gapped padlock probes targeting mRNA transcripts may performed in a flow cell. Tissues may be prepared for deparaffinization and heat-induced antigen retrieval steps using methods known in the art (see, e.g., PCT Publication WO2023076832A1). Additionally, tissues may be further permeabilized using steps described supra. Blocking oligonucleotides including a first and second sequence complementary to the target mRNA transcript may be added to the flow cell, followed by heating and removal of unbound blocking oligonucleotides prior to the addition of probe oligonucleotides, wherein a probe oligonucleotide includes a first sequence complementary to the blocking oligonucleotide and a second sequence complementary to a third sequence of the target mRNA transcript described herein. Extension of the second sequence of the probe oligonucleotide described herein is accomplished in the presence of a reverse transcriptase and dNTPs. A ligase covalently attaches the extended complement of the target mRNA transcript to the first sequence of the probe oligonucleotide to generate a circular oligonucleotide as depicted in FIG. 3C. The circular oligonucleotide may be amplified to generate amplicons including the target mRNA sequence, and the amplicons and complements thereof are subjected to multiple rounds of in situ sequencing as described herein.

Example 2. In Situ Proteomics

The human genome contains on the order of 25,000 genes which work in concert to produce on the order of 1,000,000 distinct proteins. A single mass spectrometry experiment can identify about 2,000 proteins or 0.2% of the total (Mirza, S. P., & Olivier, M. (2008). Physiological genomics, 33(1), 3-11), highlighting the need for novel approaches to identify more proteins. Certainly, when one considers the levels of mRNA are not proportional to the expression level of the proteins they code for, it is beneficial to determine the proteome of a sample (e.g., a cell).

The methods described in Example 1, for spatial RNA transcriptomics can also be applied to spatial proteomics. For example, the proteins of interest are targeted by specific binding reagents, such as antibodies, fragments thereof (e.g., Fabs), aptamers, and the like, which carry a barcoded nucleic acid strand. That barcode oligonucleotide may serve as the target polynucleotide and detected, as described above. For example, the probe oligonucleotide and blocking oligonucleotide bind to the barcode oligonucleotide and a circular oligonucleotide is generated as described herein.

Methods for spatial proteomics described supra may also be applied to a tissue immobilized in a flow cell. Tissues may be prepared for deparaffinization and heat-induced antigen retrieval steps using methods known in the art (see, e.g., PCT Publication WO2023076832A1). Additionally, tissues may be further permeabilized using steps described supra. Blocking oligonucleotides including a first and second sequences complementary to the first and second sequence of the barcode oligonucleotide may be added to the flow cell, followed by heating and removal of unbound blocking oligonucleotides prior to the addition of probe oligonucleotides, wherein a probe oligonucleotide includes a first sequence complementary to the blocking oligonucleotide and a second sequence complementary to a third sequence of the barcode oligonucleotide described herein. Extension of the probe oligonucleotide described herein is accomplished in the presence of a reverse transcriptase and dNTPs. A ligase covalently attaches the extended complement of barcode oligonucleotide to the first sequence of the probe oligonucleotide to generate a circular oligonucleotide as depicted in FIG. 3C. The circular oligonucleotide may be amplified to generate amplicons including the barcode oligonucleotide sequence, and the amplicons and complements thereof are subjected to multiple rounds of in situ sequencing as described herein. The determination of the sequence of the barcode oligonucleotide and its association to the protein of interest is made a priori. Sequencing of the amplicons and complements thereof including the sequence of the barcode oligonucleotide is used to associate and identify the protein of interest in the tissue section following bioinformatic analyses.

If higher specificity is required, RCA-PLA (proximity ligation) methods can be used; see for example the methods, complexes, and kits described in US 2002/0064779, US 2005/0287526, and US 2014/0170654, each of which are incorporated herein by reference. With these methods, an amplified product is produced only if two specific antibodies bind to the same protein (or within ~5 nm distance). One antibody provides the DNA oligo that provides the target sequence for a probe oligonucleotide, while the other antibody carries the primer for RCA. Thus, RCA reaction only occurs if both antibodies bind to their respective epitopes on the target protein (or protein complex).

Example 3: T-Cell and B-Cell Receptor Repertoire Sequencing

The functions of immune cells such as B- and T-cells are predicated on the recognition through specialized receptors of specific targets (antigens) in pathogens. There are approximately $10^{10}$-$10^{11}$ B-cells and $10^{11}$ T-cells in a human adult (Ganusov V V, De Boer R J. Trends Immunol. 2007; 28(12):514-8; and Bains I, Antia R, Callard R, Yates A J. Blood. 2009; 113(22):5480-5487). Immune cells are critical components of adaptive immunity in humans. Immune cells (e.g., T cells, B cells, NK cells, neutrophils, and monocytes) directly bind to pathogens through antigen-binding regions present on the cells. Within lymphoid organs (e.g., bone marrow for B cells and the thymus for T cells) the gene segments variable (V), joining (J), and diversity (D) rearrange to produce a novel amino acid sequence in the antigen-binding regions of antibodies that allow for the recognition of antigens from a range of pathogens (e.g., bacteria, viruses, parasites, and worms) as well as antigens arising from cancer cells. The large number of possible V-D-J segments, combined with additional (junctional) diversity, lead to a theoretical diversity of $>10^{14}$, which is further increased during adaptive immune responses. Overall, the result is that each B- and T-cell expresses a practically unique receptor, whose sequence is the outcome of both germline and somatic diversity. These antibodies also contain a constant (C) region, which confers the isotype to the antibody. In most mammals, there are five antibody isotypes: IgA, IgD, IgE, IgG, and IgM. For example, each antibody in the IgA isotype shares the same constant region.

While parts of the B-cell immunoglobulin receptor (BCR) can be traced back to segments encoded in the germline (i.e., the V, D and J segments), the set of segments used by each receptor is something that needs to be determined as it is coded in a highly repetitive region of the genome (Yaari G, Kleinstein S H. Practical guidelines for B-cell receptor repertoire sequencing analysis. Genome Med. 2015; 7:121. (2015)). Additionally, there are no pre-existing full-length templates to align the sequencing reads. Thus, obtaining long-range sequence data is incredibly insightful to gain insights into the adaptive immune response in healthy individuals and in those with a wide range of diseases. Utilizing the methods described herein, comprehensive in situ snapshots of the repertoire diversity for each class of antibody may be realized by using targeted oligonucleotide probes to sequence the C—V-D-J segments in intact B cells.

In situ sequencing involves tissue and/or cellular extraction, combined with the fixation and permeabilization of cells, followed by amplification of the target nucleic acid fragments for sequencing. Briefly, cells and their surrounding milieu are attached to a substrate surface, fixed, and permeabilized. Targeted oligonucleotide probes designed for C—V-D-J sequencing are then annealed to complementary regions which flank the nucleic acid of interest or a portion thereof. As shown in FIG. 3A, the probe oligonucleotide and blocking oligonucleotide hybridize to regions which flank the target nucleic acid sequence or a portion thereof. In the presence of a polymerase, the complement to the target sequence is generated by extending from the first complementary region and is ligated to form a circularized oligonucleotide, as found in FIG. 3C. The resulting circularized oligonucleotide is primed with an amplification primer and extended with a strand-displacing polymerase to generate a concatemer containing multiple copies of the target nucleic acid sequence, as shown in FIG. 4. This extension product is then primed with a sequencing primer and subjected to sequencing processes as described herein.

Optionally, one or more nucleotides within the amplification primer sequence, the sequencing primer sequence, and/or the immobilized oligonucleotide primer contains one or more functional moieties (e.g., bioconjugate reactive groups) that serve as attachment points to the cell or the matrix in which the cell is embedded (e.g. a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

In embodiments, the methods described herein may be utilized for B cell heavy and light chain in situ sequencing by targeting the combination of variable and constant gene segments that make up a given heavy and light chain. These methods provide unique insight into the spatial localization and recombination efforts of a cell's heavy and light chain genes, see for example FIG. 4. Likewise, the methods can be applied for T-cell receptor (TCR) alpha and beta chain in situ sequencing. The genes encoding alpha (TCRA) and beta (TCRB) chains are composed of multiple non-contiguous gene segments which include V, D, and J segments for TCRB and V and J for TCRA. As with B cell receptor diversity, the enormous diversity of TCR repertoires is generated by random combinatorial gene events. The methods described here can be used to provide a comprehensive in situ view of TCR diversity in intact T cells.

Additional Embodiments

Embodiment 1. A method of forming a circular oligonucleotide in a cell or tissue, said method comprising: contacting a target polynucleotide complex in a cell or tissue with a probe oligonucleotide, thereby forming a probe polynucleotide complex, wherein the target polynucleotide complex comprises a blocking oligonucleotide bound to a first sequence of a target polynucleotide, wherein said blocking oligonucleotide comprises a probe hybridization sequence, and wherein said probe polynucleotide complex comprises the probe oligonucleotide bound to a second sequence of the target polynucleotide and bound to the probe hybridization sequence, wherein the target sequence is between said first and second sequence; extending the probe oligonucleotide along the target sequence with a polymerase to generate an extension strand comprising a complement of the target sequence, and ligating said extension strand to the probe oligonucleotide hybridization sequence, thereby generating a circular oligonucleotide.

Embodiment 2. A method of amplifying a target sequence, said method comprising: contacting a target polynucleotide complex with a probe oligonucleotide, thereby forming a probe polynucleotide complex, wherein the target polynucleotide complex comprises a blocking oligonucleotide bound to a first sequence of a target polynucleotide, wherein said blocking oligonucleotide comprises a probe hybridization sequence, and wherein said probe polynucleotide complex comprises the probe oligonucleotide bound to a second sequence of the target polynucleotide and bound to the probe hybridization sequence, wherein the target sequence is between said first and second sequence; extending the probe oligonucleotide along the target sequence with a polymerase to generate an extension strand comprising a complement of the target sequence, and ligating said extension strand to the probe oligonucleotide hybridization sequence, thereby generating a circular oligonucleotide; and amplifying the circular oligonucleotide by extending an amplification primer hybridized to the circular oligonucleotide with a strand-displacing polymerase, thereby generating an amplification product comprising multiple copies of the target sequence.

Embodiment 3. The method of Embodiment 2, wherein the target polynucleotide complex is in a cell or tissue.

Embodiment 4. The method of any one of Embodiments 1 to 3, wherein a padlock probe oligonucleotide binds to the target polynucleotide and is detected prior to contacting the target polynucleotide complex.

Embodiment 5. The method of any of Embodiments 1 to 4, further comprising detecting the amplification product.

Embodiment 6. The method of Embodiment 5, wherein both the padlock probe oligonucleotide and the amplification product are detected in the cell or tissue.

Embodiment 7. The method of Embodiment 5, wherein the padlock probe oligonucleotide is detected in the cell or tissue and the amplification product is detected outside the cell or tissue.

Embodiment 8. The method of any one of Embodiments 5 to 7, wherein detecting comprises hybridizing a detection probe comprising a detectable label to the amplification product and detecting the detectable label.

Embodiment 9. The method of any one of Embodiments 5 to 7, wherein detecting comprises sequencing.

Embodiment 10. The method of Embodiment 9, wherein sequencing comprises sequencing by synthesis, sequencing by binding, sequencing by ligation, or pyrosequencing.

Embodiment 11. The method of Embodiment 9, wherein sequencing comprises hybridizing a sequencing primer to said amplification product, (a) extending the sequencing primer by incorporating a labeled nucleotide or labeled nucleotide analogue and (b) detecting the label for each incorporated nucleotide or nucleotide analogue.

Embodiment 12. The method of Embodiment 5, wherein the padlock probe oligonucleotide is sequenced in the cell or tissue and the amplification product is sequenced outside the cell or tissue.

Embodiment 13. The method of any one of Embodiments 1 to 12, wherein the cell is permeabilized and immobilized to a solid support.

Embodiment 14. The method of any one of Embodiments 1 to 13, wherein the target polynucleotide complex is formed by: contacting the target polynucleotide with a blocking oligonucleotide comprising a first target hybridization sequence and a probe hybridization sequence, and hybridizing said first target hybridization sequence to the target polynucleotide.

Embodiment 15. The method of Embodiment 14, wherein the first target hybridization sequence comprises a photocrosslinkable nucleotide.

Embodiment 16. The method of Embodiment 15, wherein the photocrosslinkable nucleotide comprises a carbazole moiety.

Embodiment 17. The method of Embodiment 15, wherein the photocrosslinkable nucleotide is 3-cyanovinylcarbazole phosphoramidite.

Embodiment 18. The method of any one of Embodiments 15 to 17, wherein prior to forming the probe polynucleotide complex, exposing the target polynucleotide complex to UV light thereby covalently binding the blocking oligonucleotide to the target polynucleotide.

Embodiment 19. The method of any one of Embodiments 1 to 18, wherein the blocking oligonucleotide comprises a first target hybridization sequence and a probe hybridization sequence.

Embodiment 20. The method of any one of Embodiments 1 to 18, wherein the blocking oligonucleotide comprises a first target hybridization sequence, a first curl sequence, a second curl sequence, and a probe hybridization sequence, wherein said first curl sequence is complementary to said second curl sequence.

Embodiment 21. The method of any one of Embodiments 1 to 18, wherein said blocking oligonucleotide comprises, from 3' to 5', a sequence complementary to the target polynucleotide, a first curl sequence, a second curl sequence, a spacer sequence, and a probe hybridization sequence, wherein said first curl sequence is complementary to said second curl sequence.

Embodiment 22. The method of Embodiments 20 or 21, wherein the first curl sequence is complementary to a sequence of the target polynucleotide.

Embodiment 23. The method of Embodiments 20 or 21, wherein the first curl sequence is about 4 to 15 nucleotides.

Embodiment 24. The method of any one of Embodiments 1 to 23, wherein the blocking oligonucleotide comprises a modified nucleotide.

Embodiment 25. The method of Embodiment 24, wherein the modified nucleotide comprises a retarding moiety covalently bound to the modified nucleotide.

Embodiment 26. The method of any one of Embodiments 14 to 25, wherein the first target hybridization sequence comprises locked nucleic acids (LNAs), Bis-locked nucleic acids (bisLNAs), twisted intercalating nucleic acids (TINAs), bridged nucleic acids (BNAs), 2'-O-methyl RNA: DNA chimeric nucleic acids, minor groove binder (MGB) nucleic acids, morpholino nucleic acids, C5-modified pyrimidine nucleic acids, peptide nucleic acids (PNAs), phosphorothioate nucleic acids, Zip nucleic acids (ZNAs), or combinations thereof.

Embodiment 27. The method of any one of Embodiments 14 to 25, wherein the first target hybridization sequence comprises one or more locked nucleic acids (LNAs), Zip nucleic acids (ZNAs), 2-amino-deoxyadenosine (2-amino-dA), trimethoxystilbene-functionalized oligonucleotides (TFOs), Pyrene-functionalized oligonucleotides (PFOs), peptide nucleic acids (PNAs), or aminoethyl-phenoxazine-dC (AP-dC) nucleic acids.

Embodiment 28. The method of any one of Embodiments 2 to 27, wherein the blocking oligonucleotide is the amplification primer, and amplifying comprises extending the probe hybridization sequence.

Embodiment 29. The method of any one of Embodiments 2 to 27, wherein the target polynucleotide is the amplification primer.

Embodiment 30. The method of any one of Embodiments 1 to 29, wherein said blocking oligonucleotide is covalently bound to the target polynucleotide.

Embodiment 31. The method of any one of Embodiments 1 to 30, wherein the probe oligonucleotide comprises a second target hybridization sequence and a blocking hybridization sequence.

Embodiment 32. The method of Embodiment 31, wherein the second target hybridization sequence is a random sequence.

Embodiment 33. The method of Embodiment 31, wherein the second target hybridization sequence is a random sequence comprising 4 to 30 nucleotides.

Embodiment 34. The method of any one of Embodiments 1 to 33, wherein the probe hybridization sequence comprises 5 to 25 nucleotides.

Embodiment 35. The method of any one of Embodiments 1 to 34, wherein the probe oligonucleotide further comprises a barcode sequence.

Embodiment 36. The method of any one of Embodiments 1 to 35, wherein the probe oligonucleotide comprises an amplification primer binding sequence, a sequencing primer binding sequence, or both an amplification primer binding sequence and a sequencing primer binding sequence.

Embodiment 37. The method of any one of Embodiments 1 to 36, wherein the target polynucleotide comprises a fusion gene sequence.

Embodiment 38. The method of any one of Embodiments 1 to 36, wherein the target polynucleotide comprises RNA or cDNA.

Embodiment 39. The method of any one of Embodiments 1 to 36, wherein the target polynucleotide comprises an IGH locus or a BCL-1, BCL-2, BCL-3, or BCL6 locus.

Embodiment 40. The method of any one of Embodiments 1 to 36, wherein the target polynucleotide comprises a sequence encoding for a complementarity-determining region (CDR) of a T cell receptor or a B cell receptor.

Embodiment 41. The method of any one of Embodiments 1 to 36, wherein the target polynucleotide comprises a sequence encoding for the CDR3 region of a T cell receptor or a B cell receptor.

Embodiment 42. The method of any one of Embodiments 1 to 36, wherein the target polynucleotide comprises a sequence encoding for a V region or a complement thereof and a J region or a complement thereof.

Embodiment 43. The method of any one of Embodiments 1 to 42, wherein ligating comprises covalently binding adjacent sequences with a ligase.

Embodiment 44. The method of Embodiment 43, wherein the ligase is a pre-adenylated ligase.

Embodiment 45. The method of Embodiment 43, wherein the ligase is a PBCV-1 DNA Ligase.

Embodiment 46. The method of Embodiment 43, wherein the ligase is a TS2126 RNA ligase.

Embodiment 47. The method of any one of Embodiments 1 to 46, wherein amplifying comprises RCA or eRCA.

Embodiment 48. A method of detecting a nucleic acid molecule in a cell, said method comprising amplifying the target sequence of the nucleic acid molecule of Embodiments 1 to 47, sequencing the target sequence in said cell, thereby detecting the nucleic acid molecule.

Embodiment 49. The method of Embodiment 48, further comprising sequencing the probe hybridization sequence, or a complement thereof.

Embodiment 50. The method of Embodiment 48, further comprising sequencing the curl sequence, or a complement thereof.

Embodiment 51. A method of sequencing an agent-mediated nucleic acid sequence of a cell, said method comprising administering a genetically modifying agent to the cell, and sequencing an agent-mediated nucleic acid sequence of the cell in situ according to any one of Embodiments 1 to 47.

Embodiment 52. A cell or tissue comprising a target polynucleotide complex, wherein said target polynucleotide complex comprises: a first sequence of a blocking oligonucleotide bound to a first sequence of a target polynucleotide; a first sequence of a probe oligonucleotide bound to a second sequence of the target polynucleotide; wherein the first and second sequences of the target polynucleotide are separated by 1 or more nucleotides; and where a second sequence of said blocking oligonucleotide is bound to a second sequence of said probe oligonucleotide.

Embodiment 53. A kit comprising: a blocking oligonucleotide comprising a first target hybridization sequence, a first curl sequence and a second curl sequence, and a probe hybridization sequence, wherein said first curl sequence is complementary to said second curl sequence; and a probe oligonucleotide comprising a second target hybridization sequence and a blocking hybridization sequence.

extending an amplification primer bound to the circular oligonucleotide with a strand-displacing polymerase, thereby generating an amplification product comprising multiple copies of the target sequence; and sequencing the target sequence in said cell and sequencing the second curl sequence, or a complement thereof, thereby detecting the nucleic acid molecule.

2. The method of claim 1, wherein sequencing comprises sequencing by synthesis, sequencing by hybridization, sequencing by binding, or sequencing by ligation.

3. The method of claim 1, wherein sequencing comprises hybridizing a sequencing primer to said amplification product, (a) extending the sequencing primer by incorporating a labeled nucleotide or labeled nucleotide analogue and (b) detecting the label for each incorporated nucleotide or nucleotide analogue.

4. The method of claim 1, wherein the cell is permeabilized and immobilized to a solid support.

5. The method of claim 1, wherein the first curl sequence is complementary to a sequence of the target polynucleotide.

6. The method of claim 1, wherein the first curl sequence is about 4 to 15 nucleotides.

7. The method of claim 1, wherein the blocking oligonucleotide comprises a modified nucleotide.

8. The method of claim 7, wherein the modified nucleotide comprises a retarding moiety covalently bound to the modified nucleotide.

9. The method of claim 1, wherein the first target binding sequence comprises locked nucleic acids (LNAs), Bis-

What is claimed is:

1. A method of detecting a nucleic acid molecule in a cell, said method comprising amplifying a target sequence of the nucleic acid molecule, wherein amplifying comprises:

contacting a target polynucleotide complex in a cell with a probe oligonucleotide, thereby forming a probe polynucleotide complex;

wherein the target polynucleotide complex comprises a blocking oligonucleotide bound to a first sequence of a target polynucleotide, wherein the blocking oligonucleotide comprises a first target binding sequence, a first curl sequence, a second curl sequence, and a probe binding sequence, wherein said first curl sequence is complementary to said second curl sequence, wherein said probe polynucleotide complex comprises the probe oligonucleotide bound to a second sequence of the target polynucleotide and bound to the probe binding sequence, and wherein the target sequence is between said first and second sequence;

extending the probe oligonucleotide along the target sequence with a polymerase to generate an extended probe strand comprising a complement of the target sequence, and joining said extended probe strand to the probe oligonucleotide binding sequence, thereby generating a circular oligonucleotide;

locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), phosphorothioate nucleic acids, Zip nucleic acids (ZNAs), or combinations thereof.

10. The method of claim 1, wherein the first target binding sequence comprises one or more locked nucleic acids (LNAs), Zip nucleic acids (ZNAs), 2-amino-deoxyadenosine (2-amino-dA), trimethoxystilbene-functionalized oligonucleotides (TFOs), Pyrene-functionalized oligonucleotides (PFOs), peptide nucleic acids (PNAs), or aminoethyl-phenoxazine-dC (AP-dC) nucleic acids.

11. The method of claim 2, wherein the blocking oligonucleotide is the amplification primer, and amplifying comprises extending the probe binding sequence.

12. The method of claim 2, wherein the target polynucleotide is the amplification primer.

13. The method of claim 1, wherein the probe oligonucleotide further comprises a barcode sequence.

14. The method of claim 1, wherein the target polynucleotide comprises RNA or cDNA.

15. The method of claim 1, wherein the target polynucleotide comprises an IGH locus or a BCL-1, BCL-2, BCL-3, or BCL6 locus.

16. The method of claim 1, wherein the target polynucleotide comprises a sequence encoding for a V region or a complement thereof and a J region or a complement thereof.

17. The method of claim 1, wherein joining said extended probe strand to the probe oligonucleotide binding sequence comprises covalently binding adjacent sequences with a ligase.

18. The method of claim 17, wherein the ligase is a pre-adenylated ligase.

19. The method of claim 17, wherein the ligase is a PBCV-1 DNA Ligase.

20. The method of claim 17, wherein the ligase is a TS2126 RNA ligase.

* * * * *